US009101645B2

(12) United States Patent
Watts et al.

(10) Patent No.: US 9,101,645 B2
(45) Date of Patent: Aug. 11, 2015

(54) MODULATION OF AXON DEGENERATION

(75) Inventors: Ryan Watts, San Mateo, CA (US);
Mark Chen, Mountain View, CA (US);
Joseph Wesley Lewcock, Redwood City, CA (US); Christine Pozniak, San Francisco, CA (US); Arundhati Sengupta-Ghosh, Union City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/125,333

(22) PCT Filed: Oct. 22, 2009

(86) PCT No.: PCT/US2009/061733
§ 371 (c)(1),
(2), (4) Date: Jun. 22, 2011

(87) PCT Pub. No.: WO2010/048446
PCT Pub. Date: Apr. 29, 2010

(65) Prior Publication Data
US 2011/0256150 A1    Oct. 20, 2011

Related U.S. Application Data

(60) Provisional application No. 61/197,051, filed on Oct. 22, 2008.

(51) Int. Cl.
| | | |
|---|---|---|
| A61K 39/395 | (2006.01) | |
| A61K 33/14 | (2006.01) | |
| A61K 31/277 | (2006.01) | |
| A61K 38/12 | (2006.01) | |
| A61K 31/40 | (2006.01) | |
| A61K 38/06 | (2006.01) | |
| A61K 31/7105 | (2006.01) | |
| A61K 31/7088 | (2006.01) | |
| A61K 31/711 | (2006.01) | |
| C12N 15/113 | (2010.01) | |

(52) U.S. Cl.
CPC ......... *A61K 31/7105* (2013.01); *A61K 31/7088* (2013.01); *A61K 31/711* (2013.01); *C12N 15/113* (2013.01); *C12N 15/1137* (2013.01)

(58) Field of Classification Search
None
See application file for complete search history.

(56) References Cited

U.S. PATENT DOCUMENTS

| 8,754,060 B2 | 6/2014 | DiAntonio et al. |
|---|---|---|
| 2002/0058245 A1 | 5/2002 | Liu |

(Continued)

FOREIGN PATENT DOCUMENTS

| WO | WO 99/58982 A1 | 11/1999 |
|---|---|---|
| WO | WO 00/13015 A1 | 3/2000 |

(Continued)

OTHER PUBLICATIONS

Pratt et al. 2012 "amyotrophic lateral sclerosis: update and new developments" Degener Neurol Neuromuscul Dis 2:1-14.*

(Continued)

*Primary Examiner* — Gregory S Emch
*Assistant Examiner* — Adam M Weidner
(74) *Attorney, Agent, or Firm* — Clark & Elbing LLP; Susan M. Michaud

(57) ABSTRACT

The invention relates generally to treatment of neurological disorders and nervous system injuries. The invention specifically provides methods of using modulators of particular target proteins to modulate degeneration of neurons or portions thereof, such as axons.

9 Claims, 52 Drawing Sheets

(56) References Cited

U.S. PATENT DOCUMENTS

| | | | |
|---|---|---|---|
| 2004/0067953 | A1 | 4/2004 | Stein et al. |
| 2005/0043264 | A1 | 2/2005 | Juang et al. |
| 2005/0137245 | A1 | 6/2005 | Hudkins et al. |
| 2005/0143442 | A1 | 6/2005 | Hudkins et al. |
| 2005/0239896 | A1* | 10/2005 | Gwag et al. .............. 514/567 |
| 2007/0014792 | A1 | 1/2007 | He et al. |
| 2007/0087984 | A1* | 4/2007 | Hu et al. .............. 514/44 |
| 2008/0051319 | A1 | 2/2008 | He et al. |
| 2010/0056609 | A1 | 3/2010 | DiAntonio et al. |

FOREIGN PATENT DOCUMENTS

| | | |
|---|---|---|
| WO | WO 02/065979 A2 | 8/2002 |
| WO | WO 2005/000200 A2 | 1/2005 |
| WO | WO 2005/003762 A2 | 1/2005 |
| WO | WO-2005/063764 A2 | 7/2005 |
| WO | WO 2005/103291 A1 | 11/2005 |
| WO | WO 2007/090913 A1 | 8/2007 |
| WO | WO 2008/024776 A1 | 2/2008 |
| WO | WO 2009/143865 A1 | 12/2009 |
| WO | WO-2010/048446 A2 | 4/2010 |

OTHER PUBLICATIONS

Cao et al. 2007 "Study of 99mTc-annexin V uptake in apoptotic cell models of Parkinson's disease" Nucl Med Commun 28(12):895-901 (abstract only).*

Liu et al. 2007 "Modified Wendan decoction can attenuate neurotoxic action associated with alzheimer's disease" Evid based complement alternat med 6(3):325-30 (abstract only).*

Wang et al., "JNK Inhibitor Protects Dopaminergic Neurons by Reducing COX-2 Expression in the MPTP Mouse Model of Subacute Parkinson's Disease," J. Neurological Sci. 285:172-177, 2009.

International Preliminary Report on Patentability from International Patent Application No. PCT/US2010/053596, dated Apr. 24, 2012.

Singaporean Search Report and Written Opinion from Singaporean Patent Application No. 201102810-7, dated Oct. 8, 2012.

International Preliminary Report on Patentability from International Application No. PCT/US2009/061733, dated Apr. 26, 2011.

International Search Report from International Application No. PCT/US2009/061733, dated Jun. 28, 2010.

Prior Art Search Report, Korea Institute of Patent Information, dated Oct. 8, 2010.

Chen et al., "Antiapoptotic and Trophic Effects of Dominant-Negative Forms of Dual Leucine Zipper Kinase in Dopamine Neurons of the Substantia Nigra in Vivo," J. Neurosci. 28:672-680, 2008.

Miller et al., "A DLK-Dependent Axon Self-Destruction Program Promotes Wallerian Degeneration," Nat. Neurosci. 12:387-389 (and 5 pages of figures), 2009.

Extended European Search Report from European Patent Application No. 09822734.1, dated Mar. 2, 2012 (date of mailing of report) and Feb. 22, 2012 (date of completion of search).

Martin and Liu, "Adult olfactory bulb neural precursor cell grafts provide temporary protection from motor neuron degeneration, improve motor function, and extend survival in amyotrophic lateral sclerosis mice," J. Neuropathol Exp. Neurol. 66(11): 1002-1018 (2007).

Office Action for United States Appl. No. 13/503,101, dated Feb. 12, 2013.

First Office Action for Chinese Patent Application No. 201080047538.8, dated Mar. 15, 2013.

Xu et al., "The MLK family mediates c-JUN N-terminal kinase activation in neuronal apoptosis," Mol Cell Biol. 21(14):4713-4724 (2001).

Extended European Search Report for European Patent Application No. 10825693.4, dated Aug. 28, 2013 (18 pages).

Chin et al., "K252a induces cell cycle arrest and apoptosis by inhibiting Cdc2 and Cdc25c," Cancer Invest. 17(6):391-5 (1999).

Hirai et al., "The c-Jun N-terminal kinase activator dual leucine zipper kinase regulates axon growth and neuronal migration in the developing cerebral cortex," J Neurosci. 26(46):11992-2002 (2006).

Kase et al., "K-252 compounds, novel and potent inhibitors of protein kinase C and cyclic nucleotide-dependent protein kinases," Biochem Biophys Res Commun. 142(2):436-40 (1987).

Knüsel et al., "K-252 compounds: modulators of neurotrophin signal transduction," J Neurochem. 59(6):1987-96 (1992).

Koizumi et al., "K-252a: a specific inhibitor of the action of nerve growth factor on PC 12 cells," J Neurosci. 8(2):715-21 (1988).

Philpott et al., "MAP kinase pathways in neuronal cell death," CNS Neurol Disord Drug Targets. 7(1):83-97 (2008).

"K252a from *Nonomuraea longicatena*," Sigma-Aldrich Product Information Sheet for K252a, Catalog No. K1639, accessed Jul. 14, 2014 (1 page).

Examination Report for Singaporean Patent Application No. 2012-02864-3, mailed Feb. 14, 2014 (11 pages).

Notice of Reasons for Rejection for Japanese Patent Application No. 2011-533352, dated Jan. 21, 2014 (6 pages).

Patent Examination Report No. 1 for Australian Patent Application No. 2009308293, dated Jan. 17, 2014 (4 pages).

Patent Examination Report No. 1 for Australian Patent Application No. 2010310589, dated Jun. 13, 2014 (4 pages).

Second Office Action for Chinese Patent Application No. 201080047538.8, dated Jan. 30, 2014 (7 pages).

* cited by examiner

Figure 5
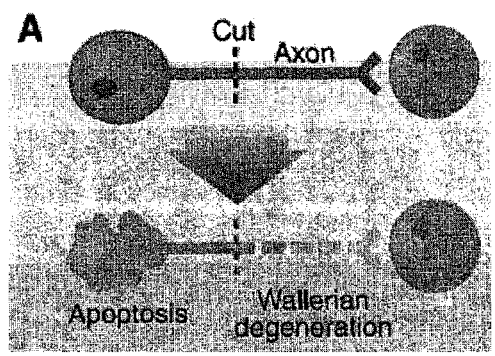
- Axon degeneration after lesion is significantly delayed
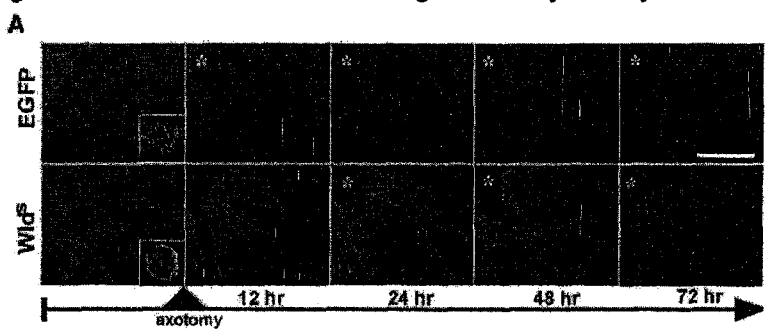

FIGURE 39
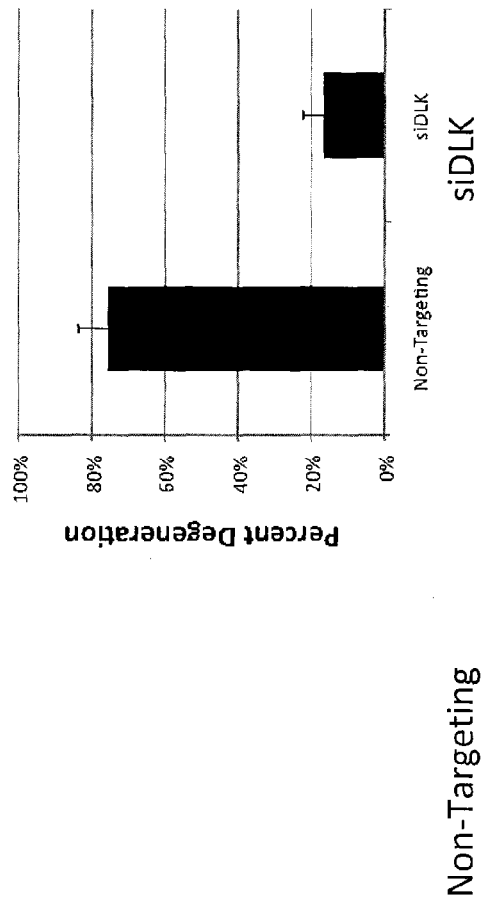
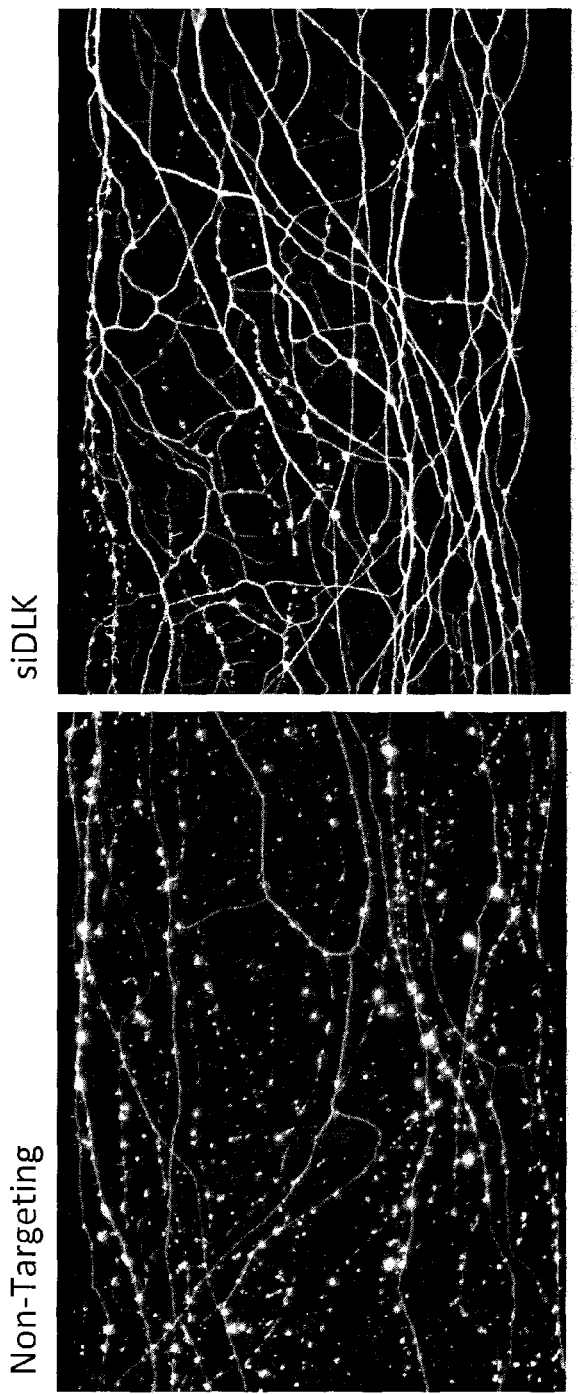

MODULATION OF AXON DEGENERATION

CROSS-REFERENCE TO RELATED APPLICATIONS

This application is the U.S. national stage filing under 35 U.S.C. §371 of international application PCT/US2009/061733, filed Oct. 22, 2009, which claims benefit of U.S. Provisional Application 61/197,051, filed Oct. 22, 2008.

FIELD OF THE INVENTION

This invention relates generally to treatment of neurological disorders and nervous system injuries. The invention specifically concerns the use of modulators of particular target proteins and processes in methods to inhibit neuron and axon degeneration.

BACKGROUND OF THE INVENTION

Neuron or axon degeneration plays a central role in the proper development of the nervous system and is a hallmark of many neurodegenerative diseases including, for example, amyotrophic lateral sclerosis (ALS), Alzheimer's disease, and Parkinson's disease, as well as traumatic injury to the brain and spinal cord. These diseases and injuries are devastating to patients and caregivers, and also result in great financial burdens, with annual costs currently exceeding several hundred billion dollars in the United States alone. Most current treatments for these diseases and conditions are inadequate. Adding to the urgency of the problems created by these diseases is the fact that many such diseases are age-related, and thus their incidence is increasing rapidly as population demographics change. There is a great need for the development of effective approaches to treating neurodegenerative diseases and nervous system injuries.

SUMMARY OF THE INVENTION

The invention provides methods for inhibiting degeneration of a neuron or a portion thereof (e.g., the neuron cell body, an axon, or a dendrite). The methods involve administering to the neuron or portion thereof an agent that modulates: (i) the activity or expression of a target protein in the neuron or portion thereof, or (ii) a process in the neuron or portion thereof.

Examples of proteins that can be targeted in the methods of the invention include dual leucine zipper-bearing kinase (DLK), glycogen synthase kinase 3β (GSK3β), p38 mitogen-activated protein kinase (p38 MAPK), β-catenin, transcription factor 4 (TCF4), epidermal growth factor receptor (EGFR), phosphoinositide 3-kinase (PI3K), cyclin-dependent kinase 5 (cdk5), adenylyl cyclase, c-Jun N-terminal kinase (JNK), BCL2-associated X protein (Bax), Ih channel, calcium/calmodulin-dependent protein kinase kinase (CaMKK), G-proteins, G-protein coupled receptors, transcription factor 4 (TCF4), or β-catenin, while examples of processes that can be targeted are transcription and protein synthesis.

The neuron or portion thereof can consist of or can be within a neuron selected from the group consisting of a cerebellar granule neuron, a dorsal root ganglion neuron, a cortical neuron, a sympathetic neuron, and a hippocampal neuron.

The agents can be, for example, inhibitors of the target protein or process. Further, the agents can be, for example, selected from the group consisting of antibodies, polypeptides, peptides, peptibodies, nucleic acid molecules, short interfering RNAs (siRNAs), polynucleotides, aptamers, small molecules, and polysaccharides. In the case of antibodies, the antibodies can be monoclonal antibodies, chimeric antibodies, humanized antibodies, human antibodies, or antibody fragments (e.g., an Fv, Fab, Fab', or F(ab')$_2$ fragment). In the case of small molecules, the agent can be, for example, selected from the group consisting of MG132, SB 415286, GSK3β inhibitor I, GSK3β inhibitor VII, GSK3β inhibitor VIII, GSK3β inhibitor XII, Lithium Chloride, SB 202190, SB 239063, SB 239069, SB 203580, SB 203580HCl, AG 556, AG 555, AG 494, PD168393, Tyrphostin B44, Tyrphostin B42 (AG 490), LY 294022, Anisomycin, Cycloheximide, Roscovitine, Forskolin, NKH 477, Actinomycin D, SP600125, Bax Channel Blocker, ZD7288, STO-609, bortezomid, disulfuram, pamapimod, gefitinib, erlotinib, lapatinib ditosylate, demeclocycline hydrochloride, gentamicin sulfate, neomycin sulfate, paromomycin sulfate, and pharmaceutically acceptable salts thereof.

The neuron or portion thereof can be present in a subject, such as a human subject. The subject can, for example, have or be at risk of developing a disease or condition selected from the group consisting of (i) disorders of the nervous system, (ii) conditions of the nervous system that are secondary to a disease, condition, or therapy having a primary effect outside of the nervous system, (iii) injuries to the nervous system caused by physical, mechanical, or chemical trauma, (iv) pain, (v) ocular-related neurodegeneration, (vi) memory loss, and (vii) psychiatric disorders.

Examples of disorders of the nervous system include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, plexus disorders, thoracic outlet destruction syndromes, peripheral neuropathies, prophyria, Alzheimer's disease, Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, Guillain-Barré syndrome, multiple sclerosis, Charcot-Marie-Tooth disease, prion disease, Creutzfeldt-Jakob disease, Gerstmann-Sträussler-Scheinker syndrome (GSS), fatal familial insomnia (FFI), bovine spongiform encephalopathy, Pick's disease, epilepsy, and AIDS demential complex.

Examples of pain include chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neuogenic or neuropathic pain, nerve inflammation or damage, shingles, herniated disc, torn ligament, and diabetes.

Examples of conditions of the nervous system that are secondary to a disease, condition, or therapy having a primary effect outside of the nervous system include peripheral neuropathy or neuralgia caused by diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

Examples of injuries to the nervous system caused by physical, mechanical, or chemical trauma include nerve damage caused by exposure to toxic compounds, heavy metals, industrial solvents, drugs, chemotherapeutic agents, dapsone, HIV medications, cholesterol lowering drugs, heart or blood pressure medications, and metronidazole. Additional examples include burn, wound, surgery, accidents, ischemia, prolonged exposure to cold temperature, stroke, intracranial hemorrhage, and cerebral hemorrhage.

Examples of psychiatric disorders include schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders.

Examples of ocular-related neurodegeneration include glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis. Examples of glaucoma include primary glaucoma, low-tension glaucoma, primary angle-closure glaucoma, acute angle-closure glaucoma, chronic angle-closure glaucoma, intermittent angle-closure glaucoma, chronic open-angle closure glaucoma, pigmentary glaucoma, exfoliation glaucoma, developmental glaucoma, secondary glaucoma, phacogenic glaucoma, glaucoma secondary to intraocular hemorrhage, traumatic glaucoma, neovascular glaucoma, drug-induced glaucoma, toxic glaucoma, and glaucoma associated with intraocular tumors, retinal deatchments, severe chemical burns of the eye, and iris atrophy.

Contacting of the neuron or portion thereof with the agent, according to the methods of the invention, can involve administering to a subject a pharmaceutical composition including the agent. The administering can be carried out by, for example, intravenous infusion; injection by intravenous, intraperitoneal, intracerebral, intramuscular, intraocular, intraarterial or intralesional routes; or topical or ocular application. Further, the methods of the invention can include administering to a subject one or more additional pharmaceutical agents.

In other examples, the neuron or portion thereof treated according to the methods of the invention is ex vivo or in vitro (e.g., a nerve graft or nerve transplant).

The invention also includes methods of identifying agents for use in inhibiting degeneration of a neuron or a portion thereof. These methods involve contacting a neuron or portion thereof with a candidate agent in an assay of axon or neuron degeneration (e.g., anti-nerve growth factor (NGF) antibodies, serum deprivation/KCl reduction, and/or rotenone treatment). Detection of reduced degeneration of the neuron or portion thereof in the presence of the candidate agent, relative to a control, indicates the identification of an agent for use in inhibiting degeneration of a neuron or portion thereof. The candidate agent can be, for example, selected from the group consisting of antibodies, polypeptides, peptides, peptibodies, nucleic acid molecules, short interfering RNAs (siRNAs), polynucleotides, aptamers, small molecules, and polysaccharides.

The invention also includes pharmaceutical compositions and kits that contain one or more agent that can be used to inhibit degeneration of a neuron or a portion thereof, as described herein. The pharmaceutical compositions and kits can include, for example, one or more agent selected from the group consisting of MG132, SB 415286, GSK3β inhibitor I, GSK3β inhibitor VII, GSK3β inhibitor VIII, GSK3β inhibitor XII, Lithium Chloride, SB 202190, SB 239063, SB 239069, SB 203580, SB 203580HCl, AG 556, AG 555, AG 494, PD168393, Tyrphostin B44, Tyrphostin B42 (AG 490), LY 294022, Anisomycin, Cycloheximide, Roscovitine, Forskolin, NKH 477, Actinomycin D, SP600125, Bax Channel Blocker, ZD7288, STO-609, bortezomid, disulfuram, pamapimod, gefitinib, erlotinib, lapatinib ditosylate, demeclocycline hydrochloride, gentamicin sulfate, neomycin sulfate, paromomycin sulfate, and pharmaceutically acceptable salts thereof. The pharmaceutical compositions and kits can optionally include one or more pharmaceutically acceptable excipients. Further, the pharmaceutical compositions and kits can optionally include instructions for use of the compositions and kits in methods for inhibiting degeneration of a neuron or portion thereof.

In any of the methods, compositions, and kits of the invention, the agent may be a DLK signaling inhibitor (e.g., a siRNA molecule targeting DLK comprising, e.g., the sequence of, desirably, GCACTGAATTGGACAACTCTT (SEQ ID NO: 1), GAGTTGTCCAATTCAGTGCTT (SEQ ID NO: 2), GGACATCGCCTCCGCTGATTT (SEQ ID NO: 3), or ATCAGCGGAGGCGATGTCCTT (SEQ ID NO: 4), or GCAAGACCCGTCACCGAAATT (SEQ ID NO: 5), TTTCGGTGACGGGTCTTGCTT (SEQ ID NO: 6), GCGGTGTCCTG GTCTACTATT (SEQ ID NO: 7), or TAGTAGACCAGGACACCGCTT (SEQ ID NO: 8); an antibody, such as, antibody 317, antibody 318, antibody 319, antibody 320, antibody 321, antibody 322, an siRNA molecule targeting the JNK1 sequence of TTGGATGAAGCCATTAGACTA (SEQ ID NO: 9), an siRNA molecule targeting the JNK2 sequence of ACCTTTAATGGACAACATTAA (SEQ ID NO: 10) or AAGGATTAGCTTTGTATCATA (SEQ ID NO: 11), an siRNA targeting the JNK3 sequence of CCCGCATGTGTCTGTATTCAA (SEQ ID NO: 12), SP600125, JNKV inhibitor, JNKVIII inhibitor, SC-202673, SY-CC-401, SP600125, As601245, XG-102, myricetin, T278A DLK, S281A DLK, S152A DLK, and the leucine zipper domain of DLK), a GSK3β inhibitor (e.g., SB415287, GSK3β inhibitor I, GSK3β inhibitor VII, GSK3β inhibitor VIII, GSK3β inhibitor XII, and lithium chloride), an EGFR pathway inhibitor (e.g., erlotinib, tyrphostin B44, tyrphostin B42/AG490, AG555, AG494, PD168393, SB203580, SB239063, SB202190, SB239069, STO-609, and SP600125), or a G-protein inhibitor (e.g., SCG292676 and pertussis toxin).

In any of the above-described methods, the administering of an agent results in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in one or more (e.g., 1, 2, 3, 4, 5, 6, 7, 8. 9, or 10) symptoms of a disorder of the nervous system; condition of the nervous system that is secondary to a disease, condition, or therapy having a primary effect outside of the nervous system; injury to the nervous system caused by physical, mechanical, or chemical trauma; pain; ocular-related neurodegeneration; memory loss; or psychiatric disorder. Non-limiting examples of such symptoms include tremors, slowness of movement, ataxia, loss of balance, depression, decreased cognitive function, short-term memory loss, long-term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity.

In any of the above-described methods, the administering results in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the likelihood of developing a disorder of the nervous system; condition of the nervous system that is secondary to a disease, condition, or therapy having a primary effect outside of the nervous system; injury to the nervous system caused by physical, mechanical, or chemical trauma; pain; ocular-related neurodegeneration; memory loss; or psychiatric disorder, compared to a control population of subjects that are not administered said agent.

The invention also provides methods for activating degeneration of a neuron or portion thereof. These methods involve administering to a neuron or portion thereof an agent that modulates: (i) the activity of a target protein in the neuron or portion thereof, or (ii) a process in the neuron or portion thereof. The target protein can be, for example, selected from the group consisting of dual leucine zipper-bearing kinase (DLK), glycogen synthase kinase 3β (GSK3β), p38 mitogen-activated protein kinase (p38 MAPK), epidermal growth factor receptor (EGFR), phosphoinositide 3-kinase (PI3K), cyclin-dependent kinase 5 (cdk5), adenylyl cyclase, c-Jun N-terminal kinase (JNK), BCL2-associated X protein (Bax), Ih channel, calcium/calmodulin-dependent protein kinase (CaMKK), a G-protein, a G-protein coupled receptor, transcription factor 4 (TCF4), or β-catenin, while the process can be, for example, transcription or protein synthesis. Further, the agent can be, for example, an activator of the target protein or process (as is the case for the targets listed above, with the exception of adenylyl cyclase). In the methods of activating degeneration of a neuron or portion thereof described above, the modulation of a target protein may be an increase in the activity or expression of GSK3β, a decrease in the activity or expression of β-catenin, and/or a loss in the activity or expression of TCF4.

The invention also provides purified antibodies that specifically bind to the phosphorylated form of DLK (e.g., antibody 318, antibody 319, antibody 320, antibody 321, or antibody 322) and inhibitory nucleic acids (e.g., siRNA) that comprise the sequence of, desirably, GCACTGAATTGGA-CAACTCTT (SEQ ID NO: 1), GAGTTGTCCAATTCAGT-GCTT (SEQ ID NO: 2), GGACATCGCCTC CGCTGATTT (SEQ ID NO: 3), or ATCAGCGGAGGCGATGTCCTT (SEQ ID NO: 4), or GCAAGACCCGTCACCGAAATT (SEQ ID NO: 5), TTTCGGTGACGGGTC TTGCTT (SEQ ID NO: 6), GCGGTGTCCTGGTCTACTATT (SEQ ID NO: 7), or TAGTAGACCAGGACACCGCTT (SEQ ID NO: 8) that mediate a decrease in the expression of DLK.

BRIEF DESCRIPTION OF THE DRAWINGS

FIG. 5 illustrates Wallerian degeneration, which takes place in axons severed from neuron cell bodies (top panel; Raff et al., Science 296(5569):868-871, 2002), and shows that there is a significant delay in axon degeneration after lesion in Wallerian Degeneration Slow (W/dS) mutants, as compared to controls (bottom panel; Araki et al., Science 305(5686): 1010-1013, 2004).

FIG. 39 shows that siRNA knockdown of DLK signaling delays local axon degeneration.

FIG. 43A shows Western blot analyses of the binding of each of the anti-pDLK antibodies described herein to DLK, DLK in the presence of a dominant negative DLK, and control kinase MLK3. FIG. 43B shows immunofluorescent microscopic images of the binding of anti-pDLK antibodies 318 and 319 to cultured 293T cells transformed with DLK (upper two images) or control kinase MLK3 (lower two images). FIGS. 43C and 43D show Western blots using JNK and phospho-JNK antibodies.

DETAILED DESCRIPTION OF THE INVENTION

A. Definitions

Figure 1:
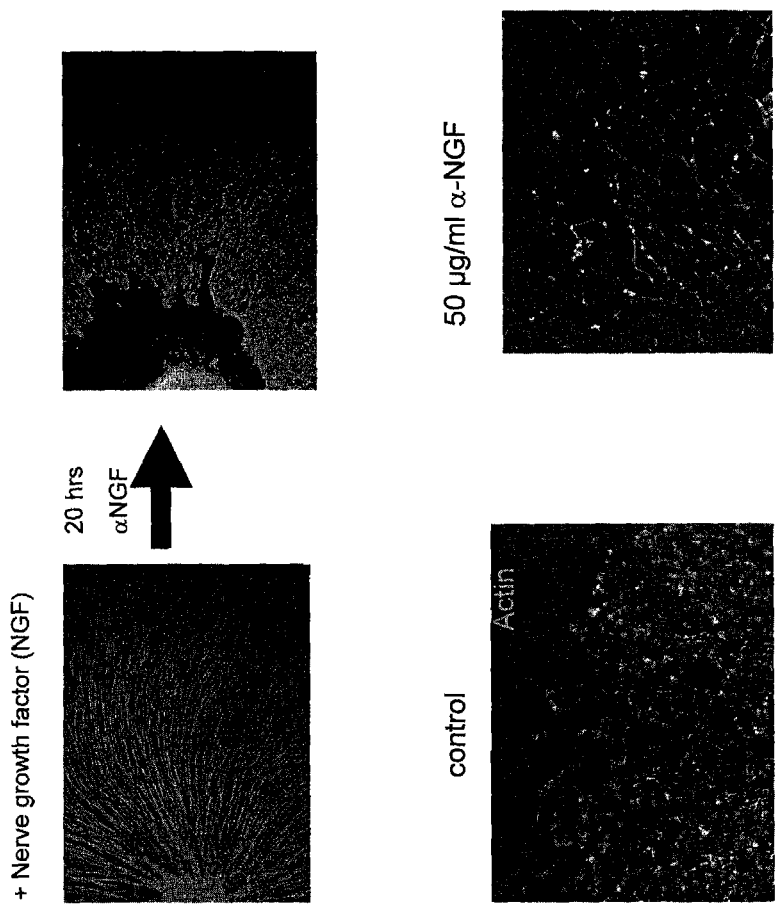
FIG. 1 shows that treatment of neurons for 20 hours with anti-NGF antibodies results in axon degeneration. The two images in the top row show neurons visualized with Tuj1 (neuron specific β-tubulin) antibodies, with and without 20 hours of treatment with anti-NGF antibodies. The two images in the bottom row show neurons visualized with actin antibodies incubated with or without (control) 50 μg/ml anti-NGF antibodies.

The term "target" is used herein to refer to proteins and processes that, when modulated by agents impacting their activities, inhibit or decrease axon degeneration. Most of the targets described herein, when contacted with an agent that inhibits their activity, inhibit or decrease axon degeneration, but the targets of the present invention also include proteins and processes that, when activated, inhibit or decrease axon degeneration. Exemplary targets of the invention are as follows: dual leucine zipper-bearing kinase (DLK), glycogen synthase kinase 3β (GSK3β), p38 mitogen-activated protein kinase (p38 MAPK), epidermal growth factor receptor (EGFR), phosphoinositide 3 kinase (PI3K), cyclin-dependent kinase 5 (Cdk5), adenylyl cyclase, c-Jun N-terminal kinase (JNK), BCL2-associated X protein (Bax), Ih channel, calcium/calmodulin-dependent protein kinase (CaMKK), a G-protein, a G-protein coupled receptor, transcription factor 4 (TCF4), β-catenin, transcription, and protein synthesis. A selection of common alternate designations for several of these targets is listed in Table 1. The targets include native, human sequences and homologues of these sequences from monkeys, mice, rats, and other non-human mammals, including all naturally occurring variants, such as alternatively spliced and allelic variants and isoforms, as well as soluble forms thereof. Exemplary, non-limiting sequence references are also provided in Table 1. Additional sequences, including sequences of various target isoforms, variants, homologues, and fragments may also be considered as targets, according to the present invention.

TABLE 1

| Target | Alternate names | Exemplary Genbank Accession numbers |
|---|---|---|
| Gycogen synthase kinase 3 beta (GSK3β) | GSK-3β; GSK-3 beta 3; GSK3beta isoform; GSK-3α, GSK-3b2 | CAG38748<br>NP_002084<br>NP_063937 |
| β-catenin | Catenin beta-1, beta-catenin, CTNNB, CTNB1 | NP_001091679<br>NP_001091680<br>NP_001895 |
| TCF4 | Transcription factor 4, E2-2, ITF2, SEF2, SEF2-1, SEF2-1A, SEF2-1B | AAI25085<br>NP_001077431<br>NP_003190<br>EAW63024<br>EAW63023<br>EAW63022<br>EAW63021<br>EAW63020<br>EAW63019<br>EAW63018<br>EAW63017<br>AAI25086<br>Q9NQB0 |
| p38 Mitogen-activated protein kinase | p38alpha (MAPK14, CSBP2, Crk1, Csbp1, MGC102436, Mxi2, PRKM14, PRKM15, p38, p38-alpha, p38MAPK, p38a, p38alpha, OTTMUSP00000021706; cytokine suppressive anti-inflammatory drug binding protein 1; mitogen activated protein kinase 14; p38 MAP kinase alpha; p38 MAPK; p38 alpha; tRNA synthetase cofactor p38)<br>p38beta (MAPK11, DKFZp586C1322, P38b, Prkm11, Sapk2, Sapk2b, p38-2, p38beta2, mitogen activated protein kinase 11; protein kinase, mitogen activated kinase, 11, p38beta)<br>p38delta (MAPK13, SAPK4, Serk4, OTTMUSP00000028863; SAPK/Erk/kinase 4; mitogen activated protein kinase 13; p38 delta MAP kinase)<br>p38gamma (MAPK12, AW123708, Erk6, Prkm12, Sapk3, mitogen activated protein kinase 12; stress activated protein kinase 3) | NP_002736.3<br>NP_620407 |
| Epidermal growth factor receptor (EGFR) | EGFR (ERBB, ERBB1, HER1, PIG61, mENA, avian erythroblastic leukemia viral (v-erb-b) oncogene homolog; cell growth inhibiting protein 40; cell proliferation-inducing protein 61; epidermal growth factor receptor)<br>ErbB2 (CD340, HER-2, HER-2/neu, HER2, NEU, NGL, TKR1, c-erb B2/neu protein; erbB-2; herstatin; neuroblastoma/glioblastoma derived oncogene homolog; v-erb-b2 avian erythroblastic leukemia viral oncogene homolog 2 | AAG35789<br>NP_005219<br>NP_958439<br>NP_958440<br>NP_958441 |

TABLE 1-continued

| Target | Alternate names | Exemplary Genbank Accession numbers |
|---|---|---|
| | (neuro/glioblastoma derived oncogene homolog)) ErbB3 (ErbB-3, HER3, LCCS2, MDA-BF-1, MGC88033, c-erbB-3, c-erbB3, erbB3-S, p180-ErbB3, p45-sErbB3, p85-sErbB3, erbB-3; lethal congenital contracture syndrome 2; v-erb-b2 avian erythroblastic leukemia viral oncogene homolog 3) ErbB4 (HER4, MGC138404, p180erbB4, avian erythroblastic leukemia viral (v-erb-b2) oncogene homolog 4; receptor tyrosine-protein kinase erbB-4; tyrosine kinase-type cell surface receptor HER4; v-erb-a avian erythroblastic leukemia viral oncogene homolog-like 4; v-erb-a erythroblastic leukemia viral oncogene homolog 4) | |
| Mitogen-activated protein kinase 8 (JNK) | Jun N-terminal kinase (1); JNK; JNK1; PRKM8; SAPK1; JNK1A2; JNK21B1/2; mitogen-activated protein kinase-8; MAPK8; JNK-46 JNK-2; Jun N-terminal kinase (2); MAPK9; JNK2; SAPK; p54a; JNK2A; JNK2B; PRKM9; JNK-55; JNK2BETA; p54aSAPK; JNK2ALPHA JNK-3; Jun N-terminal kinase (3); MAPK10; JNK3; JNK3A; PRKM10; p493F12; FLJ12099; FLJ33785; MGC50974; p54bSAPK | NP_003609 CAG38817 AAH65516 NP_002741 NP_620634 NP_620635 NP_620637 |
| Calcium/calmodulin-dependent protein kinase beta (CaMKbeta) | CAMKKA; CAMKK alpha protein; CaM-KK alpha; CaM-kinase IV kinase; CaM-kinase kinase alpha; CaMKK 1; CaMKK alpha; calcium/calmodulin-dependent protein kinase kinase alpha; calcium/calmodulin-dependent protein kinase 1 alpha; calcium/calmodulin-dependent protein kinase kinase 1, alpha CAMKKB; CAMKK beta protein; CaM-KK beta; CaM-kinase kinase beta; CaMKK beta; calcium/calmodulin-dependent protein kinase kinase beta; calcium/calmodulin-dependent protein kinase beta; calcium/calmodulin-dependent protein kinase kinase 2, beta; calcium/calmodulin-dependent protein kinase kinase 2, beta | NP_115670 NP_757343 NP_757344 NP_006540 NP_705719 NP_705720 NP_757363 NP_757364 NP_757365 NP_757380 |
| dual leucine zipper-bearing kinase | DLK, DLK1, fetal antigen 1 (FA1), PG2, PREF-1, PREF1, ZOG, delta-lika protein dlk, pG2, preadipocyte factor 1 | NP_003827 ABC26857 EAW81713 EAW81712 EAW81711 AAH14015 AAH13197 AAH07741 P80370 |
| Phosphoinositide 3 kinase | PI3-kinase, PI3K, Phosphotidylinositol 3 kinase | CAA74194 |
| Cyclin-dependent kinase 5 | Cdk5 | NP_004926 |
| Adenylyl cyclase | Adenylyl cyclase 1 (ADCY1); 3',5'-cyclic AMP synthetase (1); ATP pyrophosphate-lyases (1); Ca$^{2+}$/calmodulin-activated adenylyl cyclase; Adenylate cyclase type I; Brain adenylate cyclase 1 Adenylyl cyclase 2 (ADCY2); 3',5'-cyclic AMP synthetase (2); ATP pyrophosphate-lyase (2); adenylate cyclase type II; adenylate cyclase 2 (brain); Adenylate cyclase II; Type II adenylate cyclase Adenylyl cyclase 8 (ADCY8); ATP pyrophosphate-lyase 8; adenylate cyclase type VIII; adenylyl cyclase 8; Ca(2+)/calmodulin-activated adenylyl cyclase; adenylate cyclase 8 (brain); adenylyl cyclase-8, brain adenylate cyclase 3 (Adcy3, AC3, mKIAA0511, adenylyl cyclase 3) adenylate cyclase 4 (Adcy4, KIAA4004, mKIAA4004) adenylate cyclase 5 (Adcy5, AW121902, Ac5) adenylate cyclase 6 (Adcy6, mKIAA0422) adenylate cyclase 7 (Adcy7, AA407758, MGC141539, adenylyl cyclase type VII) adenylate cyclase 9 (Adcy9, AW125421, D16Wsu65e, mKIAA0520) | NM_021116 NP_065433 NP_001106 |

TABLE 1-continued

| Target | Alternate names | Exemplary Genbank Accession numbers |
| --- | --- | --- |
| | adenylate cyclase 10 (Adcy10, 4930431D04Rik, 4931412F17, Sacy, sAC, OTTMUSP00000023839; soluble adenylyl cyclase; testicular soluble adenylyl cyclase) | |
| Ih Channel | HCN1; hyperpolarization activated cyclic nucleotide-gated potassium channel 1; brain cyclic nucleotide-gated channel 1; BCNG-1; HAC-2 | NP_066550 |
| | HCN2; hyperpolarization activated cyclic nucleotide-gated potassium channel 2; brain cyclic nucleotide-gated channel 2; BCNG-2; HAC-1 | NP_001185 |
| | HCN3; KIAA1535; MGC131493; OTTHUMP00000034062; hyperpolarization activated cyclic nucleotide-gated potassium channel 3; potassium/sodium hyperpolarization-activated cyclic nucleotide-gated channel 3 | NP_065948 |
| | HCN4; hyperpolarization activated cyclic nucleotide-gated potassium channel 4 | NP_005468 |
| BCL2-associated X protein (Bax) | apoptosis regulator BAX; BCL2L4 | Q07812 NP_004315 NP_620116 NP_620118 NP_620119 NP_620120 |
| Transcription | Actinomycin D | |

"Isolated" when used to describe the various proteins disclosed herein, means a protein that has been identified and separated and/or recovered from a component of its natural environment. Contaminant components of its natural environment are materials that may interfere with uses (e.g., uses in therapy or antibody production) for the protein, and may include enzymes, hormones, and other proteinaceous or non-proteinaceous solutes. In various embodiments, the protein will be purified (i) to a degree sufficient to obtain at least 15 residues of N-terminal or internal amino acid sequence by use of a spinning cup sequenator, and/or (ii) to homogeneity by SDS-PAGE under non-reducing or reducing conditions using Coomassie blue or silver stain, and/or (iii) to homogeneity by mass spectroscopic or peptide mapping techniques. Isolated protein includes protein in situ within recombinant cells, as at least one component of the natural environment of the protein in question will not be present. Ordinarily, however, isolated protein will be prepared by at least one purification step. Isolated target proteins as described herein (or fragments thereof) can be used to make antibodies as described herein against the target proteins.

An "isolated" nucleic acid molecule is a nucleic acid molecule that is identified and separated from at least one contaminant nucleic acid molecule with which it is ordinarily associated in the natural source of the nucleic acid in question. An isolated nucleic acid molecule is other than in the form or setting in which it is found in nature. Isolated nucleic acid molecules therefore are distinguished from the nucleic acid molecules as they exist in natural cells. However, an isolated nucleic acid molecule includes nucleic acid molecules contained in cells that ordinarily express such nucleic acid molecule where, for example, the nucleic acid molecule is in a chromosomal location different from that of natural cells. An example of an isolated nucleic acid molecule is one lacking 5' and/or 3' flanking sequences with which it is contiguous in a natural setting.

As used herein, the terms "antagonist" and "inhibitor" refer to agents capable of blocking, neutralizing, inhibiting, abrogating, reducing and/or interfering with one or more of the activities of targets and/or reducing the expression of one or more target proteins (or the expression of nucleic acids encoding one or more target proteins) as described herein. They include, for example, antibodies, polypeptides, peptides, nucleic acid molecules, short interfering RNAs (siRNAs) and other inhibitory RNAs, small molecules (e.g., small inorganic molecules), polysaccharides, polynucleotides, aptamers, and peptibodies. Antagonists or inhibitors of particular targets as described herein (i.e., targets other than adenylyl cyclase) generally inhibit or decrease axon degeneration (e.g., by at least 10%, 15%, 20%, 25%, 30%, 35%, 40%, 45%, 50%, 55%, 60%, 65%, 70%, 75%, 80%, 85%, 90%, 95%, or even 100% decrease compared to a control that is untreated with the inhibitor), as described herein. An inhibitor may decrease the activity and/or expression of a target protein by at least 10% (e.g., by at least 15%, 20%, 25%, 30%, 35%, 40%, 45%, 50%, 55%, 60%, 65%, 70%, 75%, 80%, 85%, 90%, or even 100% decrease) as compared to the expression and/or activity of the target protein that is untreated with the inhibitor. A "DLK signaling inhibitor" is an agent capable of decreasing the activity (e.g., kinase activity) or the expression of a DLK protein (or a nucleic acid encoding a DLK protein) and/or decreasing the activity and/or expression of one or more proteins involved in a DLK signaling pathway (e.g., JNK1, JNK2, JNK3, cJun (e.g., cJun-63 and cJun-73), MKK4, and MKK7). Examples of DLK signaling inhibitors include siRNA molecules that decrease the expression of a nucleic acid encoding DLK (e.g., desirably, a sequence of GCACTGAATTGGACAACTCTT (SEQ ID NO: 1), GAGTTGTCCAATTCAGTGCTT (SEQ ID NO: 2), GGACATCGCCTCCGCTGA TTT (SEQ ID NO: 3), or ATCAGCGGAGGCGATGTCCTT (SEQ ID NO: 4), or GCAAGACCCGTCACCGAAATT (SEQ ID NO: 5), TTTCGGTGACGGG TCTTGCTT (SEQ ID NO: 6), GCG-GTGTCCTGGTCTACTATT (SEQ ID NO: 7), or TAGTA-GACCAGGACACCGCTT (SEQ ID NO: 8)), JNK1 (e.g., a sequence targeting the JNK1 sequence of TTGGATGAAGC- CATTAGACTA (SEQ ID NO: 9)), JNK2 (e.g., a sequence targeting the JNK2 sequence of ACCTTTAATGGACAA CATTAA (SEQ ID NO: 10) or AAGGATTAGCTTTGTAT-CATA (SEQ ID NO: 11)), JNK3 (e.g., a sequence targeting the JNK3 sequence of CCCGCATGTGTCT GTATTCAA (SEQ ID NO: 12)), cJun (e.g., cJun-63 and cJun-73), MKK4, and MKK7. Additional examples of DLK inhibitors include antibodies that bind to a DLK protein (e.g., antibodies that recognize unphosphorylated or phosphorylated DLK, such as the 317, 318, 319, 320, 321, and 322 antibodies described herein), JNK1, JNK2, JNK3, cJun (e.g., cJun-63 and cJun-73), MKK4, and/or MKK7; inhibitors of INK activity (e.g., SC-202673, SY-CC-401, SP600125, JNKV inhibitor, JNKVIII inhibitor, AS601245, and XG-102, as well as Catalog Nos. 420119, 420130, 420131, 420123, 420116, 420118, 420136, 420129, 420135, 420134, 420133, 420140, and 420128 from EMD Biosciences); inhibitors of MKK4 activity (e.g., myricetin and the inhibitors described in WO 04/058764), and inhibitors of MKK7 activity (e.g., inhibitors described in U.S. Pat. No. 7,195,894 and WO 04/002532). A DLK inhibitor may also be a dominant negative form or kinase-dead form of DLK protein (or a nucleic acid encoding a dominant negative form or a kinase-dead form of DLK protein), such as T278A DLK, S281A DLK, S152A DLK, and the leucine zipper domain of DLK.

Another example of an inhibitor is a "GSK3β inhibitor." GSK3β inhibitor refers to an agent capable of decreasing the activity and/or expression of GSK3β (or a nucleic acid encoding GSK3β and/or decreasing the activity and/or the expression of one or more proteins (or a nucleic acid encoding the one or more proteins) that activate GSK3β or the expression or activity of one or more substrates of GSK3β. Non-limiting examples of GSK3β inhibitors include SB415286, GSK3β inhibitor I, GSK3β inhibitor VII, GSK3β inhibitor VIII, GSK3β inhibitor XII, and lithium chloride.

An additional example of an inhibitor is a "G-protein inhibitor." A G-protein inhibitor refers to an agent capable of decreasing the activity and/or expression of one or more G-proteins or G-protein coupled receptors (GPCRs) (or the expression of one or more nucleic acids encoding a G-protein or a GPCR), and/or decreasing the activity and/or expression of one or more proteins downstream of a G-protein or a GPCR. Non-limiting examples of a G-protein inhibitor include siRNA molecules that decrease the level of expression of a nucleic acid encoding a G-protein or a GPCR, an antibody or peptibody that binds to a G-protein or GPCR, or a small molecule or peptide that inhibits the activity of a G-protein or GPCR (e.g., SCH202676 and pertussis toxin).

Another example of an inhibitor is a "EGFR pathway inhibitor." EGFR pathway inhibitor refers to an agent capable of decreasing the activity and/or expression of EGFR protein (or a nucleic acid encoding EGFR) and/or decreasing the activity and/or the expression of one or more proteins that function downstream of EGFR in the cell (e.g., p38 MAPK, CAMKK, and JNK). Non-limiting examples of EGFR pathway inhibitors include inhibitors of EGFR (e.g., erlotinib, tyrphostin B44, tyrphostin B42/AG 490, AG555, AG494, and PD168393), inhibitors of p38 MAPK (e.g., SB203580, SB239063, SB202190, and SB239069), inhibitors of CAMKK (e.g., STO-609), and inhibitors of JNK (e.g., SP600125). Additional examples of EGFR pathway inhibitors include antibodies and peptibodies that bind to EGFR, p38 MAPK, CAMKK, and/or JNK; and siRNA molecules that decrease the expression of one or more nucleic acids that encode a protein that functions downstream of EGFR in the cell (e.g., EGFR, p38 MAPK, CAMKK, and/or JNK).

An additional example of an inhibitor is a "CAMKβ inhibitor." A CAMKβ inhibitor refers to an agent capable of decreasing the activity and/or expression of CAMKβ protein (or a nucleic acid encoding CAMKβ and/or decreasing the activity and/or expression of one or more proteins that function downstream of CAMKβ in the cell. Non-limiting examples of CAMKβ inhibitors include antibodies and peptibodies that specifically bind to CAMKβ, and siRNA molecules that decrease the expression of one or more nucleic acids that encode CAMKβ or a protein that functions downstream of CAMKβ.

Another example of an inhibitor is a "cdk5 inhibitor." A cdk5 inhibitor refers to an agent capable of decreasing the activity and/or expression of cdk5 protein (or a nucleic acid encoding cdk5) and/or decreasing the activity and/or expression of one or more proteins that function downstream of cdk5 in the cell. Non-limiting examples of cdk5 inhibitors include antibodies and peptibodies that specifically bind to cdk5, and siRNA molecules that decrease the expression of one or more nucleic acids that encode cdk5 or a protein that functions downstream of cdk5.

An additional example of an inhibitor is a "TCF4 inhibitor." A TCF4 inhibitor refers to an agent capable of decreasing the activity and/or expression of TCF4 protein (or a nucleic acid encoding TCF4) and/or decreasing the activity and/or expression of a gene regulated by TCF4 protein. Non-limiting examples of TCF4 inhibitors include antibodies and peptibodies that specifically bind to TCF4 or a protein encoded by a gene regulated by TCF4, and siRNA molecules that decrease the expression of one or more nucleic acids that encode TCF4 or decrease the expression of an mRNA encoded by a gene regulated by TCF4.

An additional example of an inhibitor is a "β-catenin inhibitor." A β-catenin refers to an agent capable of decreasing the activity and/or expression of "β-catenin protein (or a nucleic acid encoding "β-catenin) and/or decreasing the activity and/or expression of a gene regulated by "β-catenin protein. Non-limiting examples of β-catenin inhibitors include antibodies and peptibodies that specifically bind to β-catenin or a protein encoded by a gene regulated by β-catenin, and siRNA molecules that decrease the expression of one or more nucleic acids that encode β-catenin or decrease the expression of an mRNA encoded by a gene regulated by β-catenin.

An additional example of an inhibitor is an "adenyl cyclase inhibitor." An adenyl cyclase inhibitor refers to an agent capable of decreasing the activity and/or expression of adenyl cyclase protein (or a nucleic acid encoding adenyl cyclase) and/or decreasing the activity and/or expression of one or more proteins that function downstream of adenyl cyclase in the cell. Non-limiting examples of adenyl cyclase inhibitors include antibodies and peptibodies that specifically bind to adenyl cyclase, and siRNA molecules that decrease the expression of one or more nucleic acids that encode adenyl cyclase or a protein that functions downstream of adenyl cyclase. Additional examples of adenyl cyclase inhibitors include small molecules that inhibit the activity of adenyl cyclase (e.g., forksolin and NKH 477).

The terms "agonist" or "activator" as used herein refer to agents capable of increasing or activating one or more of the activities of targets as described herein, and include, for example, antibodies, polypeptides, peptides, nucleic acid molecules, short interfering RNAs (siRNAs) or other inhibitory RNAs, small molecules (e.g., small inorganic molecules), polysaccharides, polynucleotides, aptamers, and peptibodies. Agonists or activators of adenylyl cyclase as described herein generally inhibit or decrease axon degeneration, while agonists or activators of the other particular targets described herein can be considered to activate axon degeneration.

The term "antibody" herein is used in the broadest sense understood in the art and specifically covers, for example, intact antibodies, monoclonal antibodies, polyclonal antibodies, monospecific antibodies, multispecific antibodies (e.g., bispecific antibodies) formed from at least two intact antibodies, antibody fragments, provided that they exhibit the desired biological activity, and intrabodies.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site or epitope. Furthermore, in contrast to polyclonal antibody preparations, which include different antibodies directed against different determinants (epitopes), each monoclonal antibody is directed against a single determinant on an antigen. In addition to their specificity, monoclonal antibodies are advantageous in that they may be synthesized so that they are uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using, for example, the techniques described in Clackson et al., Nature 352:624-628, 1991, and Marks et al., J. Mol. Biol. 222:581-597, 1991.

Antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et al., Proc. Natl. Acad. Sci. U.S.A. 81:6851-6855, 1984). Chimeric antibodies of interest herein include primatized antibodies comprising variable domain antigen-binding sequences derived from a non-human primate (e.g., Old World Monkey, Ape, etc.) and human constant region sequences.

"Antibody fragments" comprise a portion of an intact antibody, such as the antigen-binding or variable region thereof. Examples of antibody fragments include Fab, Fab', F(ab')$_2$, and Fv fragments; diabodies; linear antibodies; and single-chain antibody molecules.

The term "multispecific antibody" is used in the broadest sense and specifically covers an antibody comprising a heavy chain variable domain ($V_H$) and a light chain variable domain ($V_L$), where the $V_H V_L$ unit has polyepitopic specificity (i.e., is capable of binding to more than one different epitope on one or more biological molecules). If the multispecific antibody binds to two epitopes, it can be designated as a "bispecific antibody." Multispecific antibodies include, but are not limited to, full length antibodies, antibodies having two or more $V_L$ and $V_H$ domains, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s).

An "intact" antibody is one that comprises an antigen-binding variable region as well as a light chain constant domain ($C_L$) and heavy chain constant domains, $C_H1$, $C_H2$, and $C_H3$. The constant domains may be native sequence constant domains (e.g., human native sequence constant domains) or amino acid sequence variants thereof. In one example, the intact antibody has one or more effector functions.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit, or nonhuman primate having the desired specificity and affinity. In some instances, framework region (FR) residues of the human immunoglobulin are replaced by corresponding non-human residues. Furthermore, humanized antibodies may comprise residues that are not found in the recipient antibody or in the donor antibody. These modifications may be made to further refine antibody performance. In general, the humanized antibody will comprise substantially all of at least one, and typically two, variable domains (Fab, Fab', F(ab')$_2$, Fabc, Fv), in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fe), typically that of a human immunoglobulin. For further details see, for example, Jones et al., Nature 321:522-525, 1986; Riechmann et al., Nature 332:323-329, 1988; and Presta, Curr. Op. Struct. Biol. 2:593-596, 1992.

The term "hypervariable region" when used herein refers to the regions of an antibody variable domain that are hypervariable in sequence and/or form structurally defined loops. The hypervariable region comprises amino acid residues from a "complementarity determining region" or "CDR" (i.e., residues 24-34, 50-56, and 89-97 in the light chain variable domain and 31-35, 50-65, and 95-102 in the heavy chain variable domain; Kabat et al., Sequences of Proteins of Immunological Interest, 5th Ed. Public Health Service, National Institutes of Health, Bethesda, Md., 1991) and/or those residues from a "hypervariable loop" (i.e., residues 26-32, 50-52, and 91-96 in the light chain variable domain and 26-32, 53-55, and 96-101 in the heavy chain variable domain; Chothia et al., J. Mol. Biol. 196:901-917, 1987). In both cases, the variable domain residues are numbered according to Kabat et al., supra, as discussed in more detail below. "Framework" or "FR" residues are those variable domain residues other than the residues in the hypervariable regions as herein defined.

A "parent antibody" or "wild-type" antibody is an antibody comprising an amino acid sequence that lacks one or more amino acid sequence alterations compared to an antibody variant as herein disclosed. Thus, the parent antibody generally has at least one hypervariable region that differs in amino acid sequence from the amino acid sequence of the corresponding hypervariable region of an antibody variant. The parent polypeptide may comprise a native sequence (i.e., a naturally occurring) antibody (including a naturally occurring allelic variant), or an antibody with pre-existing amino acid sequence modifications (such as insertions, deletions, and/or other alterations) of a naturally occurring sequence. The terms "wild type," "WT," "wt," and "parent" or "parental" antibody may be used interchangeably.

As used herein, "antibody variant" or "variant antibody" refers to an antibody that has an amino acid sequence that differs from the amino acid sequence of a parent antibody. In one example, the antibody variant comprises a heavy chain variable domain or a light chain variable domain having an amino acid sequence that is not found in nature. Such variants necessarily have less than 100% sequence identity or similarity with the parent antibody. In one embodiment, the antibody variant will have an amino acid sequence from about 75% to less than 100% amino acid sequence identity or similarity with the amino acid sequence of either the heavy or light chain variable domain of the parent antibody, for example, about 80% to less than 100%, from about 85% to less than 100%, from about 90% to less than 100%, or from about 95% to less than 100%. The antibody variant is generally one that comprises one or more amino acid alterations in or adjacent to one or more hypervariable regions thereof.

An "amino acid alteration" refers to a change in the amino acid sequence of a predetermined amino acid sequence. Exemplary alterations include insertions, substitutions, and deletions. An "amino acid substitution" refers to the replacement of an existing amino acid residue in a predetermined amino acid sequence with another, different amino acid residue.

A "replacement" amino acid residue refers to an amino acid residue that replaces or substitutes another amino acid residue in an amino acid sequence. The replacement residue may be a naturally occurring or non-naturally occurring amino acid residue.

An "amino acid insertion" refers to the introduction of one or more amino acid residues into a predetermined amino acid sequence. The amino acid insertion may comprise a "peptide insertion" in which case a peptide comprising two or more amino acid residues joined by peptide bond(s) is introduced into the predetermined amino acid sequence. Where the amino acid insertion involves insertion of a peptide, the inserted peptide may be generated by random mutagenesis such that it has an amino acid sequence that does not exist in nature. An amino acid alteration "adjacent a hypervariable region" refers to the introduction or substitution of one or more amino acid residues at the N-terminal and/or C-terminal end of a hypervariable region, such that at least one of the inserted or replacement amino acid residue(s) forms a peptide bond with the N-terminal or C-terminal amino acid residue of the hypervariable region in question.

A "naturally occurring amino acid residue" is one encoded by the genetic code, generally selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val).

A "non-naturally occurring amino acid residue" as referred to herein is an amino acid residue other than those naturally occurring amino acid residues listed above, which is able to covalently bind adjacent amino acid residue(s) in a polypeptide chain. Examples of non-naturally occurring amino acid residues include norleucine, ornithine, norvaline, homoserine, and other amino acid residue analogues such as those described in Ellman et al., *Meth. Enzym.* 202:301-336, 1991. To generate such non-naturally occurring amino acid residues, the procedures of Noren et al., *Science* 244:182, 1989, and Ellman et al., supra, can be used. Briefly, these procedures involve chemically activating a suppressor tRNA with a non-naturally occurring amino acid residue followed by in vitro transcription and translation of the RNA.

Throughout this disclosure, reference is made to the numbering system from Kabat, E. A., et al., Sequences of Proteins of Immunological Interest (National Institutes of Health, Bethesda, Md., 1987 and 1991). In these compendiums, Kabat lists many amino acid sequences for antibodies for each subclass, and lists the most commonly occurring amino acid for each residue position in that subclass. Kabat uses a method for assigning a residue number to each amino acid in a listed sequence, and this method for assigning residue numbers has become standard in the field. The Kabat numbering scheme is followed in this description. For purposes of this invention, to assign residue numbers to a candidate antibody amino acid sequence that is not included in the Kabat compendium, one follows the following steps. Generally, the candidate sequence is aligned with any immunoglobulin sequence or any consensus sequence in Kabat. Alignment may be done by hand or by computer using commonly accepted computer programs, such as the Align 2 program. Alignment may be facilitated by using some amino acid residues that are common to most Fab sequences. For example, the light and heavy chains each typically have two cysteines that have the same residue numbers; in $V_L$ domain the two cysteines are typically at residue numbers 23 and 88, and in the $V_H$ domain the two cysteine residues are typically at numbers 22 and 92. Framework residues generally, but not always, have approximately the same number of residues, however the CDRs will vary in size. For example, in the case of a CDR from a candidate sequence that is longer than the CDR in the sequence in Kabat to which it is aligned, typically suffixes are added to the residue number to indicate the insertion of additional residues. For candidate sequences that, for example, align with a Kabat sequence for residues 34 and 36 but have no residue between them to align with residue 35, the number 35 is simply not assigned to a residue.

As used herein, an antibody with a "high-affinity" is an antibody having a $K_D$, or dissociation constant, in the nanomolar (nM) range or better. A $K_D$ in the "nanomolar range or better" may be denoted by XnM, where X is a number less than about 10.

The term "filamentous phage" refers to a viral particle capable of displaying a heterogenous polypeptide on its surface and includes, without limitation, fl, fd, Pfl, and M13. The filamentous phage may contain a selectable marker such as tetracycline (e.g., "fd-tet"). Various filamentous phage display systems are well known to those of skill in the art (see, e.g., Zacher et al., *Gene* 9:127-140, 1980, Smith et al., *Science* 228:1315-1317, 1985; and Parmley et al., *Gene* 73:305-318, 1988).

The term "panning" is used to refer to the multiple rounds of a screening process that is used in the identification and isolation of phages carrying compounds, such as antibodies, with high affinity and specificity to a target.

The term "short-interfering RNA (siRNA)" refers to small double-stranded RNAs that interfere with gene expression. siRNAs are mediators of RNA interference, the process by which double-stranded RNA silences homologous genes. siRNAs typically are comprised of two single-stranded RNAs of about 15-25 nucleotides in length that form a duplex, which may include single-stranded overhang(s). Processing of the double-stranded RNA by an enzymatic complex, for example, polymerases, results in cleavage of the double-stranded RNA to produce siRNAs. The antisense strand of the siRNA is used by an RNA interference (RNAi) silencing complex to guide mRNA cleavage, thereby promoting mRNA degradation. To silence a specific gene using siRNAs, for example, in a mammalian cell, a base pairing region is selected to avoid chance complementarity to an unrelated mRNA. RNAi silencing complexes have been identified in the art, such as, for example, by Fire et al., *Nature* 391:806-811, 1998, and McManus et al., *Nat. Rev. Genet.* 3(10):737-747, 2002.

The term "interfering RNA (RNAi)" is used herein to refer to a double-stranded RNA that results in catalytic degradation of specific mRNAs, and thus can be used to inhibit/lower expression of a particular gene.

As used herein, the term "disorder" in general refers to any condition that would benefit from treatment with the agents or inhibitors of the present invention, including any disease or disorder that can be treated by effective amounts of inhibitors of the targets described herein (or activators, in the case of adenylyl cyclase). Non-limiting examples of disorders to be treated herein include those listed in section E of the present application, below.

The terms "treating," "treatment," and "therapy" as used herein refer to curative therapy, prophylactic therapy, and preventative therapy. Consecutive treatment or administration refers to treatment on at least a daily basis without interruption in treatment by one or more days. Intermittent treatment or administration, or treatment or administration in an intermittent fashion, refers to treatment that is not consecutive, but rather cyclic in nature. Treatment according to the methods of the invention can result in complete relief or cure from a disease or condition, or partial amelioration of one or more symptoms of the disease or condition, and can be temporary or permanent.

The phrases "preventing axon degeneration," "preventing neuron degeneration," "inhibiting axon degeneration," or "inhibiting neuron degeneration" as used herein include (i) the ability to inhibit or prevent axon or neuron degeneration in patients newly diagnosed as having a neurodegenerative disease or at risk of developing a new neurodegenerative disease and (ii) the ability to inhibit or prevent further axon or neuron degeneration in patients who are already suffering from, or have symptoms of, a neurodegenerative disease. Preventing axon or neuron degeneration includes decreasing or inhibiting axon or neuron degeneration, which may be characterized by complete or partial inhibition of neuron or axon degeneration. This can be assessed, for example, by analysis of neurological function. The above-listed terms also include in vitro and ex vivo methods. Further, the phrases "preventing neuron degeneration" and "inhibiting neuron degeneration" include such inhibition with respect to the entire neuron or a portion thereof, such as the neuron cell body, axons, and dendrites. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, or even 100% decrease) in one or more (e.g., 1, 2, 3, 4, 5, 6, 7, 8, or 9) symptoms of a disorder of the nervous system; a condition of the nervous system that is secondary to a disease, condition, or therapy having a primary effect outside of the nervous system; an injury to the nervous system caused by physical, mechanical, or chemical trauma, pain; an ocular-related neurodegeneration; memory loss; or a psychiatric disorder (e.g., tremors, slowness of movement, ataxia, loss of balance, depression, decreased cognitive function, short-term memory loss, long-term memory loss, confusion, changes in personality, language difficulties, loss of sensory perception, sensitivity to touch, numbness in extremities, muscle weakness, muscle paralysis, muscle cramps, muscle spasms, significant changes in eating habits, excessive fear or worry, insomnia, delusions, hallucinations, fatigue, back pain, chest pain, digestive problems, headache, rapid heart rate, dizziness, blurred vision, shadows or missing areas of vision, metamorphopsia, impairment in color vision, decreased recovery of visual function after exposure to bright light, and loss in visual contrast sensitivity) in a subject or population compared to a control subject or population that does not receive the one or more agent described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the number of neurons (or neuron bodies, axons, or dendrites thereof) that degenerate in a neuron population or in a subject compared to the number of neurons (or neuron bodies, axons, or dendrites thereof) that degenerate in neuron population or in a subject that is not administered the one or more of the agents described herein. The administration of one or more agent as described herein may result in at least a 10% decrease (e.g., at least 15%, 20%, 25%, 30%, 35%, 40%, 45%, 50%, 55%, 60%, 65%, 70%, 75%, 80%, 85%, 90%, 95%, or even 100% decrease) in the likelihood of developing a disorder of the nervous system; a condition of the nervous system that is secondary to a disease, condition, or therapy having a primary effect outside of the nervous system; an injury to the nervous system caused by physical, mechanical, or chemical trauma, pain; an ocular-related neurodegeneration; memory loss; or a psychiatric disorder in a subject or a subject population compared to a control subject or population not treated with the one or more agent described herein.

The term "administering" as used herein refers to contacting a neuron or portion thereof with an inhibitor as described herein. This includes administration of the inhibitor to a subject in which the neuron or portion thereof is present, as well as introducing the inhibitor into a medium in which a neuron or portion thereof is cultured.

The term "neuron" as used herein denotes nervous system cells that include a central cell body or soma, and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment according to the invention include cerebellar granule neurons, dorsal root ganglion neurons, and cortical neurons.

The term "mammal" as used herein refers to any animal classified as a mammal, including humans, higher non-human primates, rodents, and domestic and farm animals, such as cows, horses, dogs, and cats. In one embodiment of the invention, the mammal is a human.

Administration "in combination with" one or more further therapeutic agents includes simultaneous (concurrent) and consecutive administration, in any order.

An "effective amount" is an amount sufficient to effect beneficial or desired therapeutic (including preventative) results. An effective amount can be administered in one or more administrations.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. The term "progeny" refers to any and all offspring of every generation subsequent to an originally transformed cell or cell line. Mutant progeny that have the same function or biological activity as screened for in the originally transformed cell are included.

A "small molecule" is defined herein to have a molecular weight below about 1000 Daltons, for example, below about 500 Daltons. Small molecules may be organic or inorganic, and may be isolated from, for example, compound libraries or natural sources, or may be obtained by derivatization of known compounds.

"Aptamers" are nucleic acid molecules that form tertiary structures that specifically bind to a target molecule, such as the targets described herein. The generation and therapeutic use of aptamers are well established in the art (see, e.g., U.S. Pat. No. 5,475,096). Aptamers used in the invention can include modified nucleotides (e.g., nucleic acid analogs or derivatives) that are stable from degradation in vivo. At a minimum, the nucleic acid molecules are designed to be sufficiently stable in vivo, for a sufficient length of time, to allow therapeutic action to take place prior to degradation and/or elimination. As non-limiting examples, such nucleotide analogs can be selected from the group consisting of phosphorothioate, boranophosphate, methyl-phosphonate, and 2'-O-methyl analogs, and analogs thereof. As a specific example, the analog can be 2'-deoxy-2'-fluoro-RNA (2'-F-RNA).

"Peptibodies" are peptide sequences linked to an amino acid sequence encoding a fragment or portion of an immunoglobulin molecule. The peptide sequences may be derived from randomized sequences selected by any method for specific binding. including but not limited to, phage display technology. In one embodiment, the selected polypeptide may be linked to an amino acid sequence encoding the Fc portion of an immunoglobulin. Peptibodies that specifically bind to and modulate the targets described herein, leading to inhibition of neuron degeneration, are also useful in the methods of the invention.

The term "pharmaceutically acceptable salt" is used herein to refer to those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, Berge et al. describe pharmaceutically acceptable salts in detail in *J. Pharm. Sci.* 66:1-19, 1977. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

B. Screening Assays to Identify and Characterize Inhibitors of Neuron Degeneration The invention is based in part on the discovery that certain modulators of the target proteins and activities listed in Table 1 in section A, above (dual leucine zipper-bearing kinase (DLK), glycogen synthase kinase 3β (GSK3β), p38 mitogen-activated protein kinase (p38 MAPK), epidermal growth factor receptor (EGFR), phosphoinositide 3 kinase (PI3K), cyclin-dependent kinase 5 (Cdk5), adenylyl cyclase, c-Jun N-terminal kinase (JNK), BCL2-associated X protein (Bax), Ih channel, calcium/calmodulin-dependent protein kinase kinase (CaMKK), a G-protein, a G-protein coupled receptor, transcription factor 4 (TCF4), β-catenin, transcription, and protein synthesis) are effective inhibitors of neuron (such as axon) degeneration. The modulators function as inhibitors of the target proteins and activities, with the exception of the modulator of adenylyl cyclase, which is an activator. The inhibitors of neuron or axon degeneration are referred to as "inhibitors" herein, regardless of their effects on their respective targets, as they are inhibitors of neuron or axon degeneration. They are also referred to herein as "agents" that modulate the activity of a target protein or activity in the neuron or axon, leading to inhibition of neuron or axon degeneration.

The invention includes methods of inhibiting neuron or axon degeneration by use of inhibitors as described herein. As described in further detail below, the methods can be carried out in vivo, such as in the treatment of neurological disorders or injuries to the nervous system. The methods can also be carried out in vitro or ex vivo, such as in laboratory studies of neuron function and in the treatment of nerve grafts or transplants. These methods are described further below, after a description of methods for identifying and testing inhibitors used in the invention.

Inhibitors that can be used in the invention include those listed in Table 2 (section C, below), which have been shown in assays described herein to prevent neuron or axon degeneration, as well as additional, known inhibitors of the targets described herein (see, e.g., Table 3). Additional inhibitors for use in the invention can be identified using standard screening methods specific for each target, as summarized below. These assays can also be used to confirm the activities of derivatives of compounds found to have a desired activity, which are designed according to standard medicinal chemistry approaches. After an inhibitor (or activator, in the case of adenylyl cyclase) is confirmed as being active with respect to a particular target, the inhibitors can be tested in models of neuron or axon degeneration, as described herein, as well as in appropriate animal model systems.

Exemplary assays for identifying inhibitors of the targets listed in Table 1, as well as for identifying and characterizing additional inhibitors of neuron or axon degeneration, which can be used in the methods of the invention, are described briefly as follows.

i) Cell-Based and In Vitro Assays for Inhibitors of Neuron or Axon Degeneration

Assays for confirming that an inhibitor of the targets described herein also inhibits neuron or axon degeneration, as well as for identifying additional inhibitors of neuron or axon degeneration, are described in detail in the Examples, below, and are briefly summarized as follows. These assays include (i) anti-Nerve Growth Factor (anti-NGF) antibody assays, (ii) serum deprivation/potassium chloride (KCl) reduction assays, (iii) rotenone degeneration assays, and (iv) vincristine degeneration assays. Additional assays for assessing neuron or axon degeneration that are known in the art can also be used in the invention.

NGF is a small, secreted protein involved in differentiation and survival of target neurons. Treatment of cultured neurons with NGF results in proliferation of axons, while treating such neurons with anti-NGF antibodies results in axon degeneration. Treatment of neurons with anti-NGF antibodies also leads to several different morphological changes that are detectable by microscopy, and which can be monitored to observe the effects of candidate inhibitors. These changes, which are described further in Example 1 and illustrated in, for example, FIGS. 1-4, include varicosity formation, loss of elongated mitochondria, accumulation of mitochondria in varicosities, cytoskeletal disassembly, and axon fragmentation. Agents that are found to counter any of the morphological changes induced by anti-NGF antibodies can be considered as candidate inhibitors of neuron or axon degeneration, which may, if desired, be tested in additional systems, such as those described herein.

The serum deprivation/KCl reduction assay is based on the use of cultures of cerebellar granule neurons (CGN) isolated from mouse (e.g., P7 mouse) brains. In this assay, the neurons are cultured in a medium including KCl and then are switched to medium containing less KCl (Basal Medium Eagles including 5 mM KCl), which induces neuron degeneration. Agents that are found to block or reduce neuron degeneration upon KCl withdrawal, which can be detected by, for example, analysis of images of fixed neurons stained with a neuronal marker (e.g., anti-class III beta-tubulin) can be considered as candidate inhibitors of neuron or axon degeneration, which may, if desired, be tested in additional systems, such as those described herein.

Another model of neuron or axon degeneration involves contact of cultured neurons with rotenone (2R,6aS,12aS)-1,2,6,6a,12,12a-hexahydro-2-isopropenyl-8,9-dimethoxy-chromeno[3,4-b]furo(2,3-h)chromen-6-one), which is a pesticide and insecticide that naturally occurs in the roots and stems of several plants, interferes with mitochondrial electron transport, and causes Parkinson's disease-like symptoms when injected into rats. Agents that are found to block or reduce degeneration of neurons cultured in the presence of rotenone, which can be detected by, for example, analysis of images of fixed neurons stained with, e.g., an antibody against neuron specific beta III tubulin, can be considered as candidate inhibitors of neuron or axon degeneration, which may, if desired, be tested in additional systems, such as those described herein.

An additional model of neuron or axon degeneration involves contact of cultured neurons with vincristine, an alkaloid that binds to tubulin dimers and prevents assemble of microtubule structures. Agenst that are found to block or reduce degeneration of neurons cultured in the presence of vincristine, which can be detected by, for example, analysis of images of fixed neurons stained with, e.g., an antibody against neuron specific beta III tubulin, can be considered as candidate inhibitors of neuron or axon degeneration, which may, if desired, be tested in additional systems, such as those described herein.

In addition to the assays described above, for which the read-out is inhibition of neuron or axon degeneration, the invention also employs assays directed at detecting inhibitors of the targets listed in Table 1, for which the read-out is, for example, target binding or target activity. Thus, the invention includes the use of screening assays for inhibitors of the targets listed in Table 1, which may be designed to identify compounds that bind or complex with the targets, or otherwise interfere with their activities. The screening assays include assays amenable to high-throughput screening of chemical libraries, making them suitable for identifying small molecule drug candidates. Generally, binding assays and activity assays are used. The assays can be performed in a variety of formats, including, without limitation, kinase assays, biochemical screening assays, immunoassays, and cell-based assays, as determined to be appropriate, based on the subject target.

In binding assays, the interaction is binding, and the complex formed can be isolated or detected in the reaction mixture. In a particular embodiment, either the target polypeptide or the drug candidate is immobilized on a solid phase, e.g., on a microtiter plate, by covalent or non-covalent attachments. Non-covalent attachment generally is accomplished by coating the solid surface with a solution of the polypeptide and drying. Alternatively, an immobilized antibody, e.g., a monoclonal antibody, specific for the target polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound is a polypeptide that interacts with but does not bind to the target, the interaction of the target with the respective polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields et al., Nature (London) 340:245-246, 1989; Chien et al., Proc. Natl. Acad. Sci. U.S.A. 88:9578-9582, 1991) as disclosed by Chevray et al., Proc. Natl. Acad. Sci. U.S.A. 89:5789-5793, 1991. Many transcriptional activators, such as yeast GAL4, consist of two physically discrete modular domains, one acting as the DNA-binding domain, and the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain.

The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of the target and other intra- or extracellular components can be tested as follows. Usually a reaction mixture is prepared containing the target and the intra- or extracellular component under conditions and for a time allowing for the interaction of the two products. To test the ability of a candidate compound to inhibit the interaction of the target, the reaction is run in the absence and in the presence of the test compound. In addition, a placebo may be added to a third reaction mixture, to serve as a positive control.

Assays for measuring the impact of a candidate inhibitor on the activity of a protein kinase are known in the art, and include direct phosphorylation assays, typically interpreted via radio-labeled phosphate, phosphorylation-specific antibodies to a substrate, and cell-based assays that measure the downstream consequence of kinase activity, e.g., activation of a reporter gene. Both of these major strategies, in addition to alternative assays based on fluorescence polarization, may be used in small-scale or high-throughput format to identify, validate, or characterize an inhibitor (see, for example, Favata et al., *J. Biol. Chem.* 273:18623-18632, 1998; Parker et al., *J. Biomol. Screening* 5:77-99, 2000; Singh et al., *Comb. Chem. High Throughput Screen* 8:319-325, 2005; Garton et al., *Meth. Enz.* 439:491-500, 2008; and Kupchko et al., *Anal. Biochem.* 317:210-217, 2003).

The screening assays specifically discussed herein are for the purpose of illustration only. A variety of other assays, which can be selected depending on the particular target and type of antagonist candidates screened (e.g., antibodies, polypeptides, peptides, non-peptide small organic molecules, nucleic acid molecules, etc.) are well known to those skilled in the art and may also be used in the present invention.

The assays described herein may be used to screen libraries of compounds including, without limitation, chemical libraries, natural product libraries (e.g., collections of microorganisms, animals, plants, etc.), and combinatorial libraries comprised of random peptides, oligonucleotides, or small organic molecules. In a particular embodiment, the assays herein are used to screen antibody libraries including, without limitation, naïve human, recombinant, synthetic, and semi-synthetic antibody libraries. The antibody library can, for example, be a phage display library, including monovalent libraries, displaying on average one single-chain antibody or antibody fragment per phage particle, and multi-valent libraries, displaying, on average, two or more antibodies or antibody fragments per viral particle. However, the antibody libraries to be screened in accordance with the present invention are not limited to phage display libraries. Other display techniques include, for example, ribosome or mRNA display (Mattheakis et al., *Proc. Natl. Acad. Sci. U.S.A.* 91:9022-9026, 1994; Hanes et al., *Proc. Natl. Acad. Sci. U.S.A.* 94:4937-4942, 1997), microbial cell display, such as bacterial display (Georgiou et al., *Nature Biotech.* 15:29-34, 1997), or yeast cell display (Kieke et al., *Protein Eng.* 10:1303-1310, 1997), display on mammalian cells, spore display, viral display, such as retroviral display (Urban et al., *Nucleic Acids Res.* 33:e35, 2005), display based on protein-DNA linkage (Odegrip et al., *Proc. Acad. Natl. Sci. U.S.A.* 101:2806-2810, 2004; Reiersen et al., *Nucleic Acids Res.* 33:e10, 2005), and microbead display (Sepp et al., *FEBS Lett.* 532:455-458, 2002).

The results obtained in the primary binding/interaction assays herein can be confirmed in in vitro and/or in vivo assays of axon degeneration. Alternatively, in vitro and/or in vivo assays of axon degeneration may be used as primary assays to identify inhibitors and antagonists as described herein.

ii) Animal Models of Neuron or Axon Degeneration

In vivo assays for use in the invention include animal models of various neurodegenerative diseases, such as animal models of amyotrophic lateral sclerosis (ALS), Alzheimer's disease, Parkinson's disease, and multiple sclerosis (e.g., experimental autoimmune encephalitis (EAE) in mice). In addition, spinal cord and traumatic brain injury models can be used. Non-limiting examples of in vivo assays that can be used in characterizing inhibitors for use in the invention are described as follows.

In the case of amyotrophic lateral sclerosis (ALS), a transgenic mouse that expresses a mutant form of superoxide dismutase 1 (SOD1) recapitulates the phenotype and pathology of ALS (Rosen et al., *Nature* 362(6415):59-62, 1993). In addition to the SOD1 mouse, several mouse models of amyotrophic lateral sclerosis (ALS) have been developed and can be used in the invention. These include motor neuron degeneration (Mnd), progressive motor neuropathy (pmn), wobbler (Bird et al., *Acta Neuropathologica* 19(1):39-50, 1971), and TDP-43 mutant transgenic mice (Wegorzewska et al., *Proc. Natl. Acad. Sci. U.S.A.*, e-published on Oct. 15, 2009). In addition, a canine model has been developed and can be used in the invention (hereditary canine spinal muscular atrophy (HCSMA)).

Animal models that simulate the pathogenic, histological, biochemical, and clinical features of Parkinson's disease, which can be used in characterizing inhibitors for use in the methods of the present invention, include the reserpine (rabbit; Carlsson et al., *Nature* 180:1200, 1957); methamphetamine (rodent and non-human primates; Seiden et al., *Drug Alcohol Depend* 1:215-219, 1975); 6-OHDA (rat; Perese et al., *Brain Res.* 494:285-293, 1989); MPTP (mouse and non-human primates; Langston et al., *Ann. Neurol.* 46:598-605, 1999); paraquat/maneb (mouse; Brooks et al., *Brain Res.* 823:1-10, 1999 and Takahashi et al., *Res. Commun. Chem. Pathol. Pharmacol.* 66:167-170, 1989); rotenone (rat; Betarbet et al., *Nat. Neurosci.* 3:1301-1306, 2000); 3-nitrotyrosine (mouse; Mihm et al., *J. Neurosci.* 21:RC149, 2001); and mutated α-synuclein (mouse and *Drosophila*; Polymeropoulos et al., *Science* 276:2045-2047, 1997) models.

Genetically-modified animals, including mice, flies, fish, and worms, have been used to study the pathogenic mechanisms behind Alzheimer's disease. For example, mice transgenic for β-amyloid develop memory impairment consistent with Alzheimer's disease (Götz et al., *Mol. Psychiatry.* 9:664-683, 2004). Models such as these may be used in characterizing the inhibitors.

Several animal models are used in the art to study stroke, including mice, rats, gerbils, rabbits, cats, dogs, sheep, pigs, and monkeys. Most focal cerebral ischemia models involve occlusion of one major cerebral blood vessel such as the middle cerebral artery (see, e.g., Garcia, *Stroke* 15:5-14, 1984 and Bose et al., *Brain Res.* 311:385-391, 1984). Any of these models may also be used in the invention.

C. Inhibitors of Neuron or Axon Degeneration

As described further below, in the Examples, the compounds listed in Table 2, below, were identified as inhibitors of neuron or axon degeneration. These compounds, as well as other agents (see, e.g., Table 3) that inhibit (or activate, in the case of adenylyl cyclase) the targets and processes listed in Table 2, can be used in methods of inhibiting neuron or axon degeneration, according to the invention.

TABLE 2

| Target | Compounds (Source) | Structure |
|---|---|---|
| Proteasome | MG132 (Calbiochem Cat. No. 474790) (CAS: 133407-82-6) | *(structure)* |
| GSK3β | SR 415286 (Tocris Cat. No. 1617) (CAS: 264218-23-7) | *(structure)* |
| | GSK3β inhibitor I (Calbiochem Cat. No. 361540) (CAS: 327036-89-5) | *(structure)* |
| | GSK3β inhibitor VII (Calbiochem Cat. No. 361548) (CAS: 99-73-0) | *(structure)* |
| | GSK3β inhibitor VIII (Calbiochem Cat. No. 361549) (CAS: 487021-52-3) | *(structure)* |
| | GSK3β inhibitor XII (Calbiochem Cat. No. 361554) (CAS: 601514-19-6) | *(structure)* |
| | Lithium Chloride Other lithium salts (e.g., lithium carbonate (e.g., Lithobid™) and lithium citrate) (CAS: 7447-41-8) | LiCl |

TABLE 2-continued

| Target | Compounds (Source) | Structure |
|---|---|---|
| P38 MAPK | SB 202190 (Calbiochem Cat. No. 559388) (CAS: 152121-30-7) | 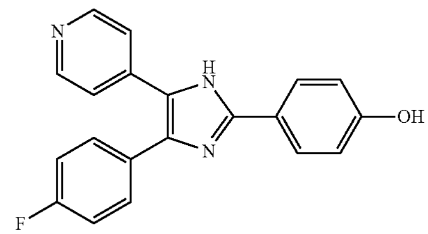 [SMILES: Oc1ccc(-c2nc(-c3ccc(F)cc3)c(-c3ccncc3)[nH]2)cc1] |
| | SB 239063 (Calbiochem Cat. No. 559404) (CAS: 193551-21-2) | |
| | SB 239069 | |
| | SB 203580 (Calbiochem Cat. No. 559389) (CAS: 152121-47-6) | |
| EGFRK | AG 556 (Calbiochem Cat. No. 658415) (CAS: 149092-35-3) | 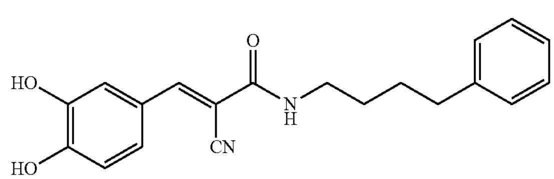 [SMILES: N#C/C(=C\c1ccc(O)c(O)c1)C(=O)NCCCCc1ccccc1] |
| | AG 555 (Calbiochem Cat. No. 658404) (CAS: 133550-34-2) | |
| | AG 494 (Tocris Cat. No. 0619) (CAS: 133550-35-3) | |

TABLE 2-continued
| Target | Compounds (Source) | Structure |
|---|---|---|
| | PD168393 (Calbiochem Cat. No. 513033) | 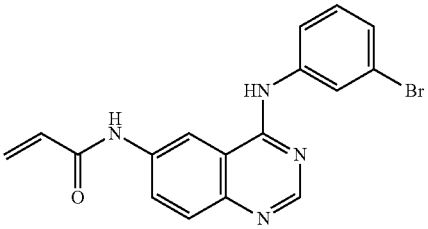 [SMILES: C=CC(=O)Nc1ccc2ncnc(Nc3cccc(Br)c3)c2c1] |
| | Tyrphostin B44 (+ and − isomers) (Calbiochem Cat. No. 658402) (CAS: 133550-32-0) | 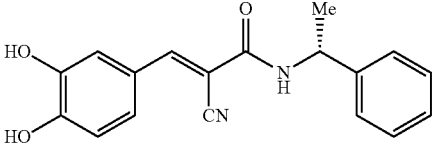 |
| | AG 490 Tyrphostin B42 (Calbiochem. Cat. No. 658401) (CAS: 133550-30-8) | 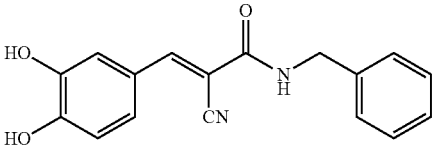 [SMILES: N#C/C(=C\c1ccc(O)c(O)c1)C(=O)NCc1ccccc1] |
| PI3K | LY294002 (Calbiochem. Cat. No. 440202) (CAS: 154447-36-6) | 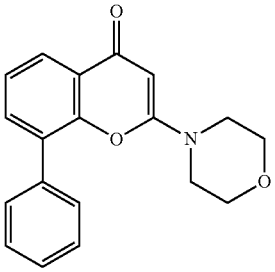 [SMILES: O=c1cc(N2CCOCC2)oc2c(-c3ccccc3)cccc12] |
| Cdk5 | Seliciclib (R-roscovitine/CYC202) (CAS: 186692-46-6) | 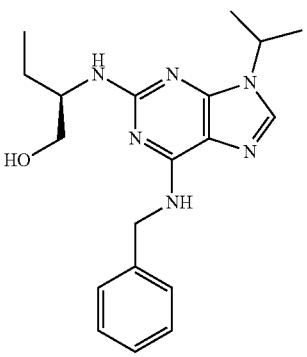 [SMILES: CC[C@H](CO)Nc1nc(NCc2ccccc2)c2ncn(C(C)C)c2n1] |
| Adenylyl cyclase | Forskolin (Calbiochem Cat. No. 344270) (CAS: 66575-29-9) | 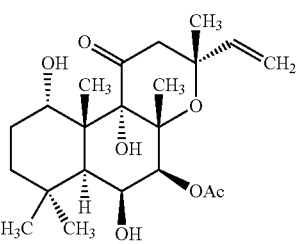 |

TABLE 2-continued

| Target | Compounds (Source) | Structure |
|---|---|---|
| | NKH 477 (Tocris Cat. No. 1603) (CAS: 138605-00-2) | |
| Transcription | Actinomycin D (Calbiochem Cat. No. 114666) (CAS: 50-76-0) | 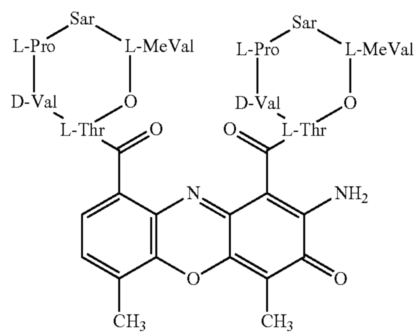 |
| JNK | SP600125 (Calbiochem Cat. No. 420119) (CAS: 129-56-6) | 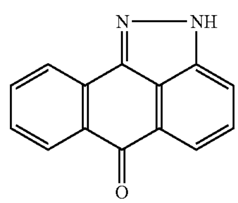 [SMILES: O=C1c2ccccc2-c2n[nH]c3cccc1c23] |
| | JNKV Inhibitor AS601245 (Calbiochem Cat. No. 420129) | |
| | JNKVIII Inhibitor Calbiochem Cat. No. 420135 | |

TABLE 2-continued

| Target | Compounds (Source) | Structure |
|---|---|---|
| Bax Channel | Bax Channel Blocker (Tocris Cat. No. 2160) (CAS: 335165-68-9) | 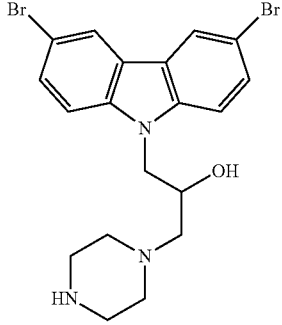 [SMILES: OC(CN1CCNCC1)Cn1c2ccc(Br)cc2c2cc(Br)ccc21] |
| Ih Channel | ZD7288 (Tocris Cat. No. 1000) (CAS: 133059-99-1) | 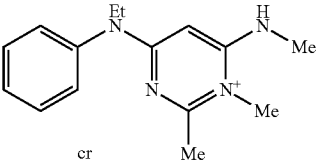 |
| CAMK | STO-609 (Calbiochem Cat. No. 570250) (CAS: 52029-86-4) | 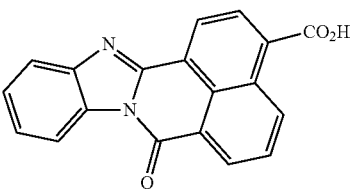 [SMILES: O=C(O)c1ccc2c3c1cccc3c(=O)n1c3ccccc3nc21] |
| Protein Synthesis | Anisomycin (CAS: 22862-76-6) | 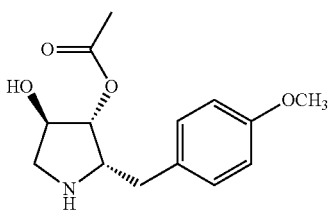 [SMILES: COc1ccc(C[C@@H]2NC[C@@H](O)[C@@H]2OC(C)=O)cc1] |
| | Cycloheximide (CAS: 66-81-9) | 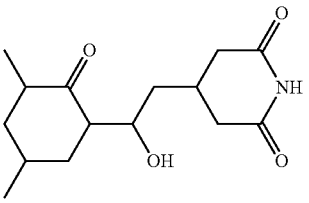 [SMILES: CC1CC(C)C(=O)C(C(O)CC2CC(=O)NC(=O)C2)C1] |

TABLE 3

| Target | Compounds | Structure | CAS/Reference |
|---|---|---|---|
| Proteasome | Bortezomib (Velcade ™) | [(1R)-3-methyl-1-({(2S)-3-phenyl-2-[(pyrazin-2-ylcarbonyl)amino]propanoyl}amino)butyl]boronic acid | CAS: 179324-69-7 Adams et al., Cancer Invest. 22 (2): 304 (2004) |
| | Disulfiram (Antabus ™/ Antabuse ™) | 1-(diethylthiocarbamoyldisulfanyl)-N,N-diethyl-methanethioamide | CAS: 97-77-8 Lövborg et al., International Journal of Cancer 118 (6): 1577 (2006) |

TABLE 3-continued

| Target | Compounds | Structure | CAS/Reference |
|---|---|---|---|
| GSK3β | Lithium Salts (e.g., lithium carbonate (e.g., Lithobid ™) and lithium citrate) | | CAS: 7447-41-8 Kaladchibachi et al., J. Circadian Rhythms 5:3 (2007) |
| p38 MAPK | Pamapimod | Pyrido[2,3-d]pyrimidin-7(8H)-one, 6-(2,4-difluorophenoxy)-2-[[3-hydroxy-1-(2-hydroxyethyl)propyl]amino]-8-methyl- | CAS: 449811-01-2 Hill et al., J. Pharmacol Exp. Therapeutics Online publication (September 2008) |
| EGFRK | Gefitinib (Iressa ™) | N-(3-chloro-4-fluoro-phenyl)-7-methoxy-6-(3-morpholin-4-ylpropoxy)quinazolin-4-amine | CAS: 184475-35-2 Paez et al., Science 304(5676): 1497 (2004) |
| | Erlotinib (Tarceva ™) | N-(3-ethynylphenyl)-6,7-bis(2-methoxyethoxy)quinazolin-4-amine | CAS: 183321-74-6 Shepherd et al., N. Engl. J. Med. 353: 123 (2005) |
| | Lapatinib ditosylate (Tykerb ™/ Tyverb ™) | N-[3-chloro-4-[(3-fluorophenyl)methoxy]phenyl]-6-[5-[(2-methylsulfonylethylamino)methyl]-2-furyl]quinazolin-4-amine | CAS: 388082-78-8 Higa et al., Exp. Rev. Anticancer Ther. 7(9): 1183 (2007) |
| Adenylyl cyclase | Demeclocycline hydrochloride (Declomycin ™/ Declostatin ™/ Ledermycin ™) | 2-(amino-hydroxy-methylidene)-7-chloro-4-dimethylamino-6,10,11,12a-tetrahydroxy-4,4a,5,5a,6,12a-hexahydrotetracene-1,3,12-trione | CAS: 127-33-3 Roitman et al., Human Psychopharmacololgy: Clinical and Experimental 13(2): 121-125 (1998) |
| Protein Synthesis | Gentamicin sulfate (Garamycin ™) | 2-[4,6-diamino-3-[3-amino-6-(1-methylaminoethyl)tetrahydropyran-2-yl]oxy-2-hydroxy-cyclohexoxy]-5-methyl-4-methylamino-tetrahydropyran-3,5-diol | CAS: 1405-41-0 Kadurugamuwa et al., J. Bacteriol. 175: 5798 (1993) |
| | Neomycin sulfate (Mycifradin ™, Neo-Rx ™) | (1R,2R,3S,4R,6S)-4,6-diamino-2-{[3-O-(2,6-diamino-2,6-dideoxy-β-L-idopyranosyl)-β-D-ribofuranosyl]oxy}-3-hydroxycyclohexyl 2,6-diamino-2,6-dideoxy-α-D-glucopyranoside | CAS: 1404-04-2 Hu, Proc. Natl. Acad. Sci. USA 95(17): 9791 (1998) |
| | Paromomycin sulfate (Humatin ™) | (2R,3S,4R,5R,6S)-5-amino-6-[(1R,2S,3S,4R,6S)-4,6-diamino-2-[(2S,3R,4R,5R)-4-[(2R,3R,4R,5R,6S)-3-amino-6-(aminomethyl)-4,5-dihydroxy-oxan-2-yl]oxy-3-hydroxy-5-(hydroxymethyl)oxolan-2-yl]oxy-3-hydroxy-cyclohexyl]oxy-2-(hydroxymethyl)oxane-3,4-diol | CAS: 1263-89-4 VanLoock et al., J. Molecular Biol. 304(4): 507 (2000) |

D. Making Antibody Inhibitors of Neuron or Axon Degeneration

Antibodies identified by the binding and activity assays of the present invention can be produced by methods known in the art, including techniques of recombinant DNA technology.

(i) Antigen Preparation

Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells that have been transformed by recombinant techniques to express the transmembrane molecule. Exemplary sequences of targets of the invention are referred to in Table 1, and can be used in the preparation of antigens for making antibodies for use in the invention. Other antigens and forms thereof useful for preparing antibodies will be apparent to those in the art.

(ii) Polyclonal Antibodies

Polyclonal antibodies are typically raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R_1N=C=NR$, where R and $R_1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ⅒ of the original amount of peptide or conjugate in Freund's complete adjuvant by subcutaneous injection at multiple sites. Seven to 14 days later the animals are bled and serum is assayed for antibody titer. Animals are boosted until the titer plateaus. The animal can be boosted with a conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et al., *Nature* 256:495, 1975, or may be made by recombinant DNA methods (see, e.g., U.S. Pat. No. 4,816,567). In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103, Academic Press, 1986).

The hybridoma cells thus prepared are seeded and grown in a suitable culture medium that can contain one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Exemplary myeloma cells are those that fuse efficiently, support stable high-level production of antibody by the selected antibody-producing cells, and are sensitive to a medium such as HAT medium. Among these, particular myeloma cell lines that may be considered for use are murine myeloma lines, such as those derived from MOPC-21 and MPC-11 mouse tumors available from the Salk Institute Cell Distribution Center, San Diego, Calif., USA, and SP-2 or X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.* 133:3001, 1984; Brodeur et al., Monoclonal Antibody Production Techniques and Applications, pp. 51-63, Marcel Dekker, Inc., New York, 1987).

Culture medium in which hybridoma cells are growing is assayed for production of monoclonal antibodies directed against the antigen. The binding specificity of monoclonal antibodies produced by hybridoma cells can be determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, clones may be subcloned by limiting dilution procedures and grown by standard methods (Goding, Monoclonal Antibodies: Principles and Practice, pp. 59-103, Academic Press, 1986). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

In a further embodiment, antibodies or antibody fragments can be isolated from antibody phage libraries generated using the techniques described, for example, in McCafferty et al., *Nature* 348:552-554, 1990.

Clackson et al., *Nature* 352:624-628, 1991 and Marks et al., *J. Mol. Biol.* 222:581-597, 1991, describe the isolation of murine and human antibodies, respectively, using phage libraries. Subsequent publications describe the production of high affinity (nM range) human antibodies by chain shuffling (Marks et al., *Bio/Technology* 10:779-783, 1992), as well as combinatorial infection and in vivo recombination as a strategy for constructing very large phage libraries (Waterhouse et al., *Nucl. Acids. Res.* 21:2265-2266, 1993). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison et al., *Proc. Natl. Acad. Sci. U.S.A.* 81:6851, 1984), or by covalently joining to the immunoglobulin coding sequence all or part of the coding sequence for a non-immunoglobulin polypeptide.

Typically, such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iv) Humanized and Human Antibodies

A humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., *Nature* 321:522-525, 1986; Riechmann et al., *Nature* 332:323-327, 1988; Verhoeyen et al., *Science* 239:1534-1536, 1988), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework (FR) for the humanized antibody (Sims et al., *J. Immunol.* 151:2296, 1993; Chothia et al., *J. Mol. Biol.* 196:901, 1987). Another method uses a particular framework derived from the consensus sequence of all human antibodies of a particular subgroup of light or heavy chains. The same framework may be used for several different humanized antibodies (Carter et al., *Proc. Natl. Acad. Sci. USA.* 89:4285, 1992; Presta et al., *J. Immunol.* 151:2623, 1993).

It is further important that antibodies be humanized with retention of high affinity for the antigen and other favorable biological properties. To achieve this goal, according to an exemplary method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. U.S.A.* 90:2551, 1993; Jakobovits et al., *Nature* 362:255-258, 1993; Bruggermann et al., *Year in Immunol.* 7:33, 1993; and Duchosal et al., *Nature* 355:258, 1992. Human antibodies can also be derived from phage-display libraries (Hoogenboom et al., *J. Mol. Biol.* 227:381, 1991; Marks et al., *J. Mol. Biol.* 222:581-597, 1991; Vaughan et al., *Nature Biotech.* 14:309, 1996). Generation of human antibodies from antibody phage display libraries is further described below.

(v) Antibody Fragments

Various techniques have been developed for the production of antibody fragments. Traditionally, these fragments were derived via proteolytic digestion of intact antibodies (see, e.g., Morimoto et al., *J. Biochem. Biophys. Meth.* 24:107-117, 1992 and Brennan et al., *Science* 229:81, 1985). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167, 1992). In another embodiment as described in the example below, the F(ab')$_2$ is formed using the leucine zipper GCN4 to promote assembly of the F(ab')$_2$ molecule. According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv) (see WO 93/16185).

(vi) Multispecific Antibodies

Multispecific antibodies have binding specificities for at least two different epitopes, where the epitopes are usually from different antigens. While such molecules normally will only bind two different epitopes (i.e., bispecific antibodies, BsAbs), antibodies with additional specificities such as trispecific antibodies are encompassed by this expression when used herein.

Methods for making bispecific antibodies are known in the art. Traditional production of full-length bispecific antibodies is based on the coexpression of two immunoglobulin heavy chain-light chain pairs, where the two chains have different specificities (Millstein et al., *Nature* 305:537-539, 1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659, 1991. According to a different approach, antibody variable domains with the desired binding specificities (antibody-antigen combining sites) are fused to immunoglobulin constant domain sequences. The fusion can be with an immunoglobulin heavy chain constant domain, comprising at least part of the hinge, CH2, and CH3 regions. The first heavy-chain constant region (CH1) containing the site necessary for light chain binding can be present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one example of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods Enzymol.* 121: 210, 1986.

According to another approach described in WO 96/27011, the interface between a pair of antibody molecules can be engineered to maximize the percentage of heterodimers that are recovered from recombinant cell culture. The interface may comprise at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360 and WO 92/200373). Heteroconjugate antibodies may be made using any convenient cross-linking methods. Suitable crosslinking agents are well known in the art and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81, 1985 describe a procedure in which intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab'-SH fragments can also be directly recovered from *E. coli*, and can be chemically coupled to form bispecific antibodies. Shalaby et al., *J. Exp. Med.* 175:217-225, 1992 describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers (Kostelny et al., *J. Immunol.* 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. U.S.A.* 90:6444-6448, 1993, has provided an alternative mechanism for making bispecific antibody fragments. The fragments comprise a heavy-chain variable domain (VH) connected to a light-chain variable domain (VL) by a linker that is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported (see Gruber et al., *J. Immunol.* 152:5368, 1994).

Antibodies with more than two valencies are contemplated. For example, trispecific antibodies can be prepared (Tuft et al., *J. Immunol.* 147:60, 1991).

(vii) Effector Function Engineering

It may be desirable to modify an antibody used in the invention with respect to effector function, so as to enhance the effectiveness of the antibody. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC; see Caron et al., *J. Exp. Med.* 176:1191-1195, 1992 and Shopes, *J. Immunol.* 148:2918-2922, 1992).

Homodimeric antibodies with enhanced anti-tumor activity may also be prepared using heterobifunctional cross-linkers as described in Wolff et al., *Cancer Research* 53:2560-2565, 1993. Alternatively, an antibody can be engineered which has dual Fc regions and may thereby have enhanced complement lysis and ADCC capabilities (see Stevenson et al., *Anti-Cancer Drug Design* 3:219-230, 1989).

(viii) Antibody-Salvage Receptor Binding Epitope Fusions

In certain embodiments of the invention, it may be desirable to use an antibody fragment, rather than an intact antibody, to increase blood brain barrier penetration, for example. In this case, it may be desirable to modify the antibody fragment in order to increase its serum half-life. This may be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis).

The salvage receptor binding epitope can constitute a region in which any one or more amino acid residues from one or two loops of an Fc domain are transferred to an analogous position of the antibody fragment. In another example, three or more residues from one or two loops of the Fc domain are transferred, while in a further example, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the CL region or VL region, or both, of the antibody fragment.

(ix) Other Covalent Modifications of Antibodies

Covalent modifications of antibodies are included within the scope of this invention. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues. Examples of covalent modifications are described in U.S. Pat. No. 5,534, 615, which is specifically incorporated herein by reference. One example of a type of covalent modification of the antibody comprises linking the antibody to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192; or 4,179,337.

(x) Generation of Antibodies from Synthetic Antibody Phage Libraries

In a further embodiment, the invention may employ a method for generating and selecting novel antibodies using a phage display approach. The approach involves generation of synthetic antibody phage libraries based on single framework template, design of sufficient diversities within variable domains, display of polypeptides having the diversified variable domains, selection of candidate antibodies with high affinity to target the antigen, and isolation of the selected antibodies.

Details of phage display methods can be found, for example, WO 03/102157, the entire disclosure of which is expressly incorporated herein by reference.

In one example, the antibody libraries used in the invention can be generated by mutating the solvent accessible and/or highly diverse positions in at least one CDR of an antibody variable domain. Some or all of the CDRs can be mutated using the methods provided herein. In some embodiments, diverse antibody libraries can be generated by mutating positions in CDRH1, CDRH2, and CDRH3 to form a single library, or by mutating positions in CDRL3 and CDRH3 to form a single library, or by mutating positions in CDRL3 and CDRH1, CDRH2, and CDRH3 to form a single library.

A library of antibody variable domains can be generated, for example, having mutations in the solvent accessible and/or highly diverse positions of CDRH1, CDRH2, and CDRH3. Another library can be generated having mutations in CDRL1, CDRL2, and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

A library can be created by substitution of original amino acids with variant amino acids in the CDRH3 region of the variable region of the heavy chain sequence. The resulting library can contain a plurality of antibody sequences, in which the sequence diversity is primarily in the CDRH3 region of the heavy chain sequence.

In one example, the library is created in the context of the humanized antibody 4D5 sequence, or the sequence of the framework amino acids of the humanized antibody 4D5 sequence. The library can be created by substitution of at least residues 95-100a of the heavy chain with amino acids encoded by the DVK codon set, wherein the DVK codon set is used to encode a set of variant amino acids for every one of these positions. An example of an oligonucleotide set that is useful for creating these substitutions comprises the sequence (DVK). In some embodiments, a library is created by substitution of residues 95-100a with amino acids encoded by both DVK and NNK codon sets. An example of an oligonucleotide set that is useful for creating these substitutions comprises the sequence $(DVK)_6$ (NNK). In another embodiment, a library is created by substitution of at least residues 95-100a with amino acids encoded by both DVK and NNK codon sets. An example of an oligonucleotide set that is useful for creating these substitutions comprises the sequence $(DVK)_5$ (NNK). Another example of an oligonucleotide set that is useful for creating these substitutions comprises the sequence $(NNK)_6$. Other examples of suitable oligonucleotide sequences can be determined by one skilled in the art according to the criteria described herein.

In another embodiment, different CDRH3 designs are utilized to isolate high affinity binders and to isolate binders for a variety of epitopes. The range of lengths of CDRH3 generated in this library is 11 to 13 amino acids, although lengths different from this can also be generated. H3 diversity can be expanded by using NNK, DVK, and NVK codon sets, as well as more limited diversity at N and/or C-terminal.

Diversity can also be generated in CDRH1 and CDRH2. The designs of CDRH1 and H2 diversities follow the strategy of targeting to mimic natural antibodies repertoire as described with modification that focus the diversity more closely matched to the natural diversity than previous design.

For diversity in CDRH3, multiple libraries can be constructed separately with different lengths of H3 and then combined to select for binders to target antigens. The multiple libraries can be pooled and sorted using solid support selection and solution-sorting methods as described previously and herein below. Multiple sorting strategies may be employed. For example, one variation involves sorting on target bound to a solid, followed by sorting for a tag that may be present on the fusion polypeptide (e.g., anti-gD tag) and followed by another sort on target bound to solid. Alternatively, the libraries can be sorted first on target bound to a solid surface, the eluted binders are then sorted using solution phase binding with decreasing concentrations of target antigen. Utilizing combinations of different sorting methods provides for minimization of selection of only highly expressed sequences and provides for selection of a number of different high affinity clones.

High affinity binders for the target antigen can be isolated from the libraries. Limiting diversity in the H1/H2 region decreases degeneracy about $10^4$ to $10^5$ fold and allowing more H3 diversity provides for more high affinity binders. Utilizing libraries with different types of diversity in CDRH3 (e.g., utilizing DVK or NVT) provides for isolation of binders that may bind to different epitopes of a target antigen.

Of the binders isolated from the pooled libraries as described above, it has been discovered that affinity may be further improved by providing limited diversity in the light chain. Light chain diversity is generated in this embodiment as follows in CDRL1: amino acid position 28 is encoded by RDT; amino acid position 29 is encoded by RKT; amino acid position 30 is encoded by RVW; amino acid position 31 is encoded by ANR; amino acid position 32 is encoded by THT; optionally, amino acid position 33 is encoded by CTG; in CDRL2: amino acid position 50 is encoded by KBG; amino acid position 53 is encoded by AVC; and optionally, amino acid position 55 is encoded by GMA; in CDRL3: amino acid position 91 is encoded by TMT or SRT or both; amino acid position 92 is encoded by DMC; amino acid position 93 is encoded by RVT; amino acid position 94 is encoded by NHT; and amino acid position 96 is encoded by TWT or YKG or both.

In another embodiment, a library or libraries with diversity in CDRII, CDRH2, and CDRH3 regions is generated. In this embodiment, diversity in CDRH3 is generated using a variety of lengths of H3 regions and using primarily codon sets XYZ and NNK or NNS. Libraries can be formed using individual oligonucleotides and pooled or oligonucleotides can be pooled to form a subset of libraries. The libraries of this embodiment can be sorted against target bound to solid. Clones isolated from multiple sorts can be screened for specificity and affinity using ELISA assays. For specificity, the clones can be screened against the desired target antigens as well as other nontarget antigens. Those binders to the target antigen can then be screened for affinity in solution binding competition ELISA assay or spot competition assay. High affinity binders can be isolated from the library utilizing XYZ codon sets prepared as described above. These binders can be readily produced as antibodies or antigen binding fragments in high yield in cell culture.

In some embodiments, it may be desirable to generate libraries with a greater diversity in lengths of CDRH3 region. For example, it may be desirable to generate libraries with CDRH3 regions ranging from about 7 to 19 amino acids.

High affinity binders isolated from the libraries of these embodiments are readily produced in bacterial and eukaryotic cell culture in high yield. The vectors can be designed to readily remove sequences such as gD tags, viral coat protein component sequence, and/or to add in constant region sequences to provide for production of full length antibodies or antigen binding fragments in high yield.

A library with mutations in CDRH3 can be combined with a library containing variant versions of other CDRs, for example CDRL1, CDRL2, CDRL3, CDRH1, and/or CDRH2. Thus, for example, in one embodiment, a CDRH3 library is combined with a CDRL3 library created in the context of the humanized 4D5 antibody sequence with variant amino acids at positions 28, 29, 30, 31, and/or 32 using predetermined codon sets. In another embodiment, a library with mutations to the CDRH3 can be combined with a library comprising variant CDRH1 and/or CDRH2 heavy chain variable domains. In one embodiment, the CDRH1 library is created with the humanized antibody 4D5 sequence with variant amino acids at positions 28, 30, 31, 32, and 33. A CDRH2 library may be created with the sequence of humanized antibody 4D5 with variant amino acids at positions 50, 52, 53, 54, 56, and 58 using the predetermined codon sets.

(xi) Antibody Mutants

The antibodies generated from phage libraries can be further modified to generate antibody mutants with improved physical, chemical, and/or biological properties over the parent antibody. Where the assay used is a biological activity assay, the antibody mutant can have a biological activity in the assay of choice that is at least about 10 fold better, at least about 20 fold better, at least about 50 fold better, and sometimes at least about 100 fold or 200 fold better, than the biological activity of the parent antibody in that assay. For example, an anti-target antibody mutant may have a binding affinity for the target that is at least about 10 fold stronger, at least about 20 fold stronger, at least about 50 fold stronger, and sometimes at least about 100 fold or 200 fold stronger, than the binding affinity of the parent antibody.

To generate the antibody mutant, one or more amino acid alterations (e.g., substitutions) are introduced in one or more of the hypervariable regions of the parent antibody. Alternatively, or in addition, one or more alterations (e.g., substitutions) of framework region residues may be introduced in the parent antibody where these result in an improvement in the binding affinity of the antibody mutant for the antigen from the second mammalian species. Examples of framework region residues to modify include those that non-covalently bind antigen directly (Amit et al., Science 233:747-753, 1986); interact with/affect the conformation of a CDR (Chothia et al., J. Mol. Biol. 196:901-917, 1987); and/or participate in the $V_L$-$V_H$ interface (EP 239 400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alteration(s).

The hypervariable region residues that are altered may be changed randomly, especially where the starting binding affinity of the parent antibody is such that such randomly produced antibody mutants can be readily screened.

One useful procedure for generating such antibody mutants is called "alanine scanning mutagenesis" (Cunningham et al., Science 244:1081-1085, 1989). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing further or other mutations at or for the sites of substitution. Thus, while the site for introducing an amino acid sequence variation is predetermined, the nature of the mutation per se need not be predetermined. The ala-mutants produced this way are screened for their biological activity as described herein.

Normally one would start with a conservative substitution such as those shown below under the heading of "preferred substitutions." If such substitutions result in a change in biological activity (e.g., binding affinity), then more substantial changes, denominated "exemplary substitutions" in the Table 4, or as further described below in reference to amino acid classes, are introduced and the products screened.

TABLE 4

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |

TABLE 4-continued

| Original Residue | Exemplary Substitutions | Preferred Substitutions |
|---|---|---|
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Even more substantial modifications in the antibodies biological properties are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr, asn, gln;
(3) acidic: asp, glu;
(4) basic: his, lys, arg;
(5) residues that influence chain orientation: gly, pro; and
(6) aromatic: trp, tyr, phe.

Non-conservative substitutions will entail exchanging a member of one of these classes for another class.

In another embodiment, the sites selected for modification are affinity matured using phage display (see above).

Nucleic acid molecules encoding amino acid sequence mutants are prepared by a variety of methods known in the art. These methods include, but are not limited to, oligonucleotide-mediated (or site-directed) mutagenesis (see, e.g., Kunkel, Proc. Natl. Acad. Sci. USA 82:488 (1985)), PCR mutagenesis, and cassette mutagenesis of an earlier prepared mutant or a non-mutant version of the parent antibody.

In certain embodiments, the antibody mutant will only have a single hypervariable region residue substituted. In other embodiments, two or more of the hypervariable region residues of the parent antibody will have been substituted, e.g., from about two to about ten hypervariable region substitutions.

Ordinarily, the antibody mutant with improved biological properties will have an amino acid sequence having at least 75% amino acid sequence identity or similarity with the amino acid sequence of either the heavy or light chain variable domain of the parent antibody, for example, at least 80%, at least 85%, at least 90%, or at least 95% sequence identity or similarity. Identity or similarity with respect to this sequence is defined herein as the percentage of amino acid residues in the candidate sequence that are identical (i.e., same residue) or similar (i.e., amino acid residue from the same group based on common side-chain properties, see above) with the parent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

Following production of the antibody mutant, the biological activity of that molecule relative to the parent antibody is determined. As noted above, this may involve determining the binding affinity and/or other biological activities of the antibody. In a preferred embodiment of the invention, a panel of antibody mutants is prepared and screened for binding affinity for the antigen or a fragment thereof. One or more of the antibody mutants selected from this initial screen are optionally subjected to one or more further biological activity assays to confirm that the antibody mutant(s) with enhanced binding affinity are indeed useful, e.g., for preclinical studies.

The antibody mutant(s) so selected may be subjected to further modifications, oftentimes depending on the intended use of the antibody. Such modifications may involve further alteration of the amino acid sequence, fusion to heterologous polypeptide(s) and/or covalent modifications such as those elaborated below. With respect to amino acid sequence alterations, exemplary modifications are elaborated above. For example, any cysteine residue not involved in maintaining the proper conformation of the antibody mutant also may be substituted, generally with serine, to improve the oxidative stability of the molecule and prevent aberrant cross linking. Conversely, cysteine bond(s) may be added to the antibody to improve its stability (particularly where the antibody is an antibody fragment such as an Fv fragment). Another type of amino acid mutant has an altered glycosylation pattern. This may be achieved by deleting one or more carbohydrate moieties found in the antibody, and/or adding one or more glycosylation sites that are not present in the antibody. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

(xii) Recombinant Production of Antibodies

For recombinant production of an antibody, a nucleic acid encoding the antibody is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence (e.g., as described in U.S. Pat. No. 5,534,615, which is specifically incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serrafia*, e.g., *Serratia marcescans*, and *Shigella*, as well as Bacilli such as *B. subtilis* and *B. licheniformis* (e.g., *B. licheniformis* 41P disclosed in DD 266,710), *Pseudomonas* such as *P. aeruginosa*, and *Streptomyces*. One exemplary *E. coli* cloning host is *E. coli* 294 (ATCC 31,446), although other strains such as *E. coli* B, *E. coli* X 1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183, 070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subloned for growth in suspension culture, Graham et al., *J. Gen. Virol.* 36:59 (1977)); baby hamster kidney cells (BHK, ATCC CCL 10); Chinese hamster ovary cells/–DHFR (CHO, Urlaub et al., *Proc. Natl. Acad. Sci. U.S.A.* 77:4216, 1980); mouse sertoli cells (TM4, Mather, *Biol. Reprod.* 23:243-25, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68, 1982); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

The host cells used to produce antibodies for use in the invention may be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham et al., *Meth. Enz.* 58:44, 1979, Barnes et al., *Anal. Biochem.* 102:255, 1980, U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed cells, is removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13, 1983). Protein G is recommended for all mouse isotypes and for human γ3 (Guss et al., *EMBO J.* 5:1567-1575, 1986). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

E. Use of Inhibitors of Neuron or Axon Degeneration

Inhibitors of the targets described herein, such as inhibitors identified or characterized in the screening assays described herein (e.g., the particular inhibitors described above) can be used in methods for inhibiting neuron or axon degeneration.

The inhibitors are, therefore, useful in the therapy of, for example, (i) disorders of the nervous system (e.g., neurodegenerative diseases), (ii) conditions of the nervous system that are secondary to a disease, condition, or therapy having a primary effect outside of the nervous system, (iii) injuries to the nervous system caused by physical, mechanical, or chemical trauma, (iv) pain, (v) ocular-related neurodegeneration, (vi) memory loss, and (vii) psychiatric disorders. Non-limiting examples of some of these diseases, conditions, and injuries are provided below.

Examples of neurodegenerative diseases and conditions that can be prevented or treated according to the invention include amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, progressive bulbar palsy, inherited muscular atrophy, invertebrate disk syndromes (e.g., herniated, ruptured, and prolapsed disk syndromes), cervical spondylosis, plexus disorders, thoracic outlet destruction syndromes, peripheral neuropathies, prophyria, mild cognitive impairment, Alzheimer's disease, Huntington's disease, Parkinson's disease, Parkinson's-plus diseases (e.g., multiple system atrophy, progressive supranuclear palsy, and corticobasal degeneration), dementia with Lewy bodies, frontotemporal dementia, demyelinating diseases (e.g., Guillain-Barré syndrome and multiple sclerosis), Charcot-Marie-Tooth disease (CMT; also known as Hereditary Motor and Sensory Neuropathy (HMSN), Hereditary Sensorimotor Neuropathy (HSMN), and Peroneal Muscular Atrophy), prion disease (e.g., Creutzfeldt-Jakob disease, Gerstmann-Sträussler-Scheinker syndrome (GSS), fatal familial insomnia (FFI), and bovine spongiform encephalopathy (BSE, commonly known as mad cow disease)), Pick's disease, epilepsy, and AIDS demential complex (also known as HIV dementia, HIV encephalopathy, and HIV-associated dementia).

The methods of the invention can also be used in the prevention and treatment of ocular-related neurodegeneration and related diseases and conditions, such as glaucoma, lattice dystrophy, retinitis pigmentosa, age-related macular degeneration (AMD), photoreceptor degeneration associated with wet or dry AMD, other retinal degeneration, optic nerve drusen, optic neuropathy, and optic neuritis. Non-limiting examples of different types of glaucoma that can be prevented or treated according to the invention include primary glaucoma (also known as primary open-angle glaucoma, chronic open-angle glaucoma, chronic simple glaucoma, and glaucoma simplex), low-tension glaucoma, primary angle-closure glaucoma (also known as primary closed-angle glaucoma, narrow-angle glaucoma, pupil-block glaucoma, and acute congestive glaucoma), acute angle-closure glaucoma, chronic angle-closure glaucoma, intermittent angle-closure glaucoma, chronic open-angle closure glaucoma, pigmentary glaucoma, exfoliation glaucoma (also known as pseudoexfoliative glaucoma or glaucoma capsulare), developmental glaucoma (e.g., primary congenital glaucoma and infantile glaucoma), secondary glaucoma (e.g., inflammatory glaucoma (e.g., uveitis and Fuchs heterochromic iridocyclitis)), phacogenic glaucoma (e.g., angle-closure glaucoma with mature cataract, phacoanaphylactic glaucoma secondary to rupture of lens capsule, phacolytic glaucoma due to phacotoxic meshwork blockage, and subluxation of lens), glaucoma secondary to intraocular hemorrhage (e.g., hyphema and hemolytic glaucoma, also known as erythroclastic glaucoma), traumatic glaucoma (e.g., angle recession glaucoma, traumatic recession on anterior chamber angle, postsurgical glaucoma, aphakic pupillary block, and ciliary block glaucoma), neovascular glaucoma, drug-induced glaucoma (e.g., corticosteroid induced glaucoma and alpha-chymotrypsin glaucoma), toxic glaucoma, and glaucoma associated with intraocular tumors, retinal deatchments, severe chemical burns of the eye, and iris atrophy.

Examples of types of pain that can be treated according to the methods of the invention include those associated with the following conditions: chronic pain, fibromyalgia, spinal pain, carpel tunnel syndrome, pain from cancer, arthritis, sciatica, headaches, pain from surgery, muscle spasms, back pain, visceral pain, pain from injury, dental pain, neuralgia, such as neuogenic or neuropathic pain, nerve inflammation or damage, shingles, herniated disc, torn ligament, and diabetes.

Certain diseases and conditions having primary effects outside of the nervous system can lead to damage to the nervous system, which can be treated according to the methods of the present invention. Examples of such conditions include peripheral neuropathy and neuralgia caused by, for example, diabetes, cancer, AIDS, hepatitis, kidney dysfunction, Colorado tick fever, diphtheria, HIV infection, leprosy, lyme disease, polyarteritis nodosa, rheumatoid arthritis, sarcoidosis, Sjogren syndrome, syphilis, systemic lupus erythematosus, and amyloidosis.

In addition, the methods of the invention can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine, Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexyline), and Metronidazole.

The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage).

Further, the methods of the invention can be used in the prevention or treatment of memory loss such as, for example, age-related memory loss. Types of memory that can be affected by loss, and thus treated according to the invention, include episodic memory, semantic memory, short-term memory, and long-term memory. Examples of diseases and conditions associated with memory loss, which can be treated according to the present invention, include mild cognitive impairment, Alzheimer's disease, Parkinson's disease, Huntington's disease, chemotherapy, stress, stroke, and traumatic brain injury (e.g., concussion).

The methods of the invention can also be used in the treatment of psychiatric disorders including, for example, schizophrenia, delusional disorder, schizoaffective disorder, schizopheniform, shared psychotic disorder, psychosis, paranoid personality disorder, schizoid personality disorder, borderline personality disorder, anti-social personality disorder, narcissistic personality disorder, obsessive-compulsive disorder, delirium, dementia, mood disorders, bipolar disorder, depression, stress disorder, panic disorder, agoraphobia, social phobia, post-traumatic stress disorder, anxiety disorder, and impulse control disorders (e.g., kleptomania, pathological gambling, pyromania, and trichotillomania).

In addition to the in vivo methods described above, the methods of the invention can be used to treat nerves ex vivo, which may be helpful in the context of nerve grafts or nerve transplants. Thus, the inhibitors described herein can be useful as components of culture media for use in culturing nerve cells in vitro.

Therapeutic formulations of the inhibitors described herein are prepared for storage by mixing the inhibitor (such as small molecule or an antibody) having the desired degree of purity with optional physiologically acceptable carriers, excipients, or stabilizers (see, e.g., Remington's Pharmaceutical Sciences (18$^{th}$ edition), ed. A. Gennaro, 1990, Mack Publishing Co., Easton, Pa.), in the form of lyophilized cake or aqueous solutions. Acceptable carriers, excipients, or stabilizers are nontoxic to recipients at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics, or PEG.

Inhibitors to be used for in vivo administration must be sterile, which can be achieved by filtration through sterile filtration membranes, prior to or following lyophilization and reconstitution. Therapeutic compositions may be placed into a container having a sterile access port, for example, an intravenous solution bag or vial having a stopper pierceable by a hypodermic injection needle.

The inhibitors can be optionally combined with or administered in concert with each other or other agents known to be useful in the treatment of the relevant disease or condition. Thus, in the treatment of ALS, for example, inhibitors can be administered in combination with Riluzole (Rilutek), minocycline, insulin-like growth factor 1 (IGF-1), and/or methylcobalamin. In another example, in the treatment of Parkinson's disease, inhibitors can be administered with L-dopa, dopamine agonists (e.g., bromocriptine, pergolide, pramipexole, ropinirole, cabergoline, apomorphine, and lisuride), dopa decarboxylase inhibitors (e.g., levodopa, benserazide, and carbidopa), and/or MAO-B inhibitors (e.g., selegiline and rasagiline). In a further example, in the treatment of Alzheimer's disease, inhibitors can be administered with acetylcholinesterase inhibitors (e.g., donepezil, galantamine, and rivastigmine) and/or NMDA receptor antagonists (e.g., memantine). The combination therapies can involve concurrent or sequential administration, by the same or different routes, as determined to be appropriate by those of skill in the art. The invention also includes pharmaceutical compositions and kits including combinations as described herein.

In addition to the combinations noted above, other combinations included in the invention are combinations of inhibitors of degeneration of different neuronal regions. Thus, the invention includes combinations of agents that (i) inhibit degeneration of the neuron cell body, and (ii) inhibit axon degeneration. As described further below, inhibitors of GSK and transcription were found to prevent degeneration of neuron cell bodies, while inhibitors of EGFR and p38 MAPK prevent degeneration of axons. Thus, the invention includes combinations of inhibitors of GSK and EGFR (and/or p38 MAPK), combinations of transcription inhibitors and EGFR (and/or p38 MAPK), and further combinations of inhibitors of dual leucine zipper-bearing kinase (DLK), glycogen synthase kinase 3β (GSK3β), p38 MAPK, EGFF, phosphoinositide 3-kinase (PI3K), cyclin-dependent kinase 5 (cdk5), adenylyl cyclase, c-Jun N-terminal kinase (JNK), BCL2-associated X protein (Bax), In channel, calcium/calmodulin-dependent protein kinase (CaMKK), a G-protein, a G-protein coupled receptor, transcription factor 4 (TCF4), and β-catenin. The inhibitors used in these combinations can be any of those described herein, or other inhibitors of these targets.

The route of administration of the inhibitors is selected in accordance with known methods, e.g., injection or infusion by intravenous, intraperitoneal, intracerebral, intramuscular, intraocular, intraarterial or intralesional routes, topical administration, or by sustained release systems as described below.

For intracerebral use, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, *J. Neural Transm. Suppl.* 24:271, 1987; and DeYebenes et al., *Mov. Disord.* 2:143, 1987.

Suitable examples of sustained release preparations include semipermeable polymer matrices in the form of shaped articles, e.g., films or microcapsules. Sustained release matrices include polyesters, hydrogels, polylactides (U.S. Pat. No. 3,773,919; EP 58,481), copolymers of L-glutamic acid and gamma ethyl-L-glutamate (Sidman et al., *Biopolymers* 22:547, 1983), poly (2-hydroxyethyl-methacrylate) (Langer et al., *J. Biomed. Mater. Res.* 15:167, 1981; Langer, *Chem. Tech.* 12:98, 1982), ethylene vinyl acetate (Langer, et al., Id), or poly-D-(-)-3-hydroxybutyric acid (EP 133,988A). Sustained release compositions also include liposomally entrapped compounds, which can be prepared by methods known per se (Epstein et al., *Proc. Natl. Acad. Sci. U.S.A.* 82:3688, 1985; Hwang et al., *Proc. Natl. Acad. Sci.* 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

An effective amount of an active compound to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from, for example, about 1 µg/kg to up to 100 mg/kg or more (e.g., about 1 µg/kg to 1 mg/kg, about 1 µg/kg to about 5 mg/kg, about 1 mg/kg to 10 mg/kg, about 5 mg/kg to about 200 mg/kg, about 50 mg/kg to about 150 mg/mg, about 100 mg/kg to about 500 mg/kg, about 100 mg/kg to about 400 mg/kg, and about 200 mg/kg to about 400 mg/kg), depending on the factors mentioned above. Typically, the clinician will administer an active inhibitor until a dosage is reached that results in improvement in or, optimally, elimination of, one or more symptoms of the treated disease or condition. The progress of this therapy is easily monitored by conventional assays. One or more agent provided herein may be administered together or at different times (e.g., one agent is administered prior to the administration of a second agent). One or more agent may be administered to a subject using different techniques (e.g., one agent may be administered orally, while a second agent is administered via intramuscular injection or intranasally). One or more agent may be administered such that the one or more agent has a pharmacologic effect in a subject at the same time. Alternatively, one or more agent may be administered, such that the pharmacological activity of the first administered agent is expired prior the administration of one or more secondarily administered agents (e.g., 1, 2, 3, or 4 secondarily administered agents).

Antibodies of the invention (and adjunct therapeutic agent) can be administered by any suitable means, including parenteral, subcutaneous, intraperitoneal, intrapulmonary, intranasal, and, if desired for local treatment, intralesional administration. Parenteral infusions include intramuscular, intravenous, intraarterial, intraperitoneal, and subcutaneous administration. In addition, antibodies can be administered by pulse infusion, particularly with declining doses of the antibody. Dosing can be by any suitable route, e.g., by injections, such as intravenous or subcutaneous injections, depending in part on whether the administration is brief or chronic.

The location of the binding target of an antibody used in the invention can be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described in Marasco, *Gene Therapy* 4:11-15, 1997; Kontermann, *Methods* 34:163-170, 2004; U.S. Pat. Nos. 6,004,940 and 6,329,173; U.S. Patent Application Publication No. 2003/0104402, and PCT Publication No. WO 03/077945. Intracellular expression of an intrabody is effected by introducing a nucleic acid encoding the desired antibody or antigen-binding portion thereof (lacking the wild-type leader sequence and secretory signals normally associated with the gene encoding that antibody or antigen-binding fragment) into a target cell. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the binding domain of the target protein is generally advantageous. For example, based upon the variable-region sequences of an antibody, peptide molecules can be designed that retain the ability to bind the target protein sequence. Such peptides can be synthesized chemically and/or produced by recombinant DNA technology (see, e.g., Marasco et al., *Proc. Natl. Acad. Sci. U.S.A.* 90:7889-7893, 1993).

Entry of modulator polypeptides into target cells can be enhanced by methods known in the art. For example, certain sequences, such as those derived from HIV Tat or the Antennapedia homeodomain protein are able to direct efficient uptake of heterologous proteins across cell membranes (see, e.g., Chen et al., *Proc. Natl. Acad. Sci. U.S.A.* 96:4325-4329, 1999).

When the binding target is located in the brain, certain embodiments of the invention provide for the antibody or antigen-binding fragment thereof to traverse the blood-brain barrier. Certain neurodegenerative diseases are associated with an increase in permeability of the blood-brain barrier, such that the antibody or antigen-binding fragment can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or antigen-binding fragment across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., *Gene Therapy* 9:398-406, 2002), interstitial infusion/convection-enhanced delivery (see, e.g., Bobo et al., *Proc. Natl. Acad. Sci. U.S.A.* 91:2076-2080, 1994), and implanting a delivery device in the brain (see, e.g., Gill et al., *Nature Med.* 9:589-595, 2003; and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or antigen-binding fragment across the blood-brain barrier include, but are not limited to, encapsulating the antibody or antigen-binding fragment in liposomes that are coupled to antibody binding fragments that bind to receptors on the vascular endothelium of the blood-brain barrier (see, e.g., U.S. Patent Application Publication No. 2002/0025313), and coating the antibody or antigen-binding fragment in low-density lipoprotein particles (see, e.g., U.S. Patent Application Publication No. 2004/0204354) or apolipoprotein E (see, e.g., U.S. Patent Application Publication No. 2004/0131692).

Receptor and channel-based methods of transporting the antibody or antigen-binding fragment across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

Antibody compositions used in the methods of the invention are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agent currently used to prevent or treat the disorder in question. The effective amount of such other agents depends on the amount of antibodies of the invention present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody (when used alone or in combination with other agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g., 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, e.g., every week or every three weeks (e.g., such that the patient receives from about two to about twenty, or, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

F. Activation of Neuron or Axon Degeneration

The invention also includes methods for activating or increasing neuron or axon degeneration. This may be accomplished by use of an activator or agonist of one or more of the targets listed in Table 2, above (with the exception of adenylyl cyclase, with respect to which an inhibitor can be used to activate neuron or axon degeneration). Thus, agonists of dual leucine zipper-bearing kinase (DLK), glycogen synthase kinase 3β (GSK3β), p38 mitogen-activated protein kinase (p38 MAPK), epidermal growth factor receptor (EGFR), phosphoinositide 3-kinase (PI3K), cyclin-dependent kinase 5 (Cdk5), c-Jun N-terminal kinase (JNK), BCL2-associated X protein (Bax), Ih channel, and calcium/calmodulin-dependent protein kinase (CaMKK) can be used in methods of activating or increasing axon degeneration. Such agonists may be identified or characterized in assays of axon degeneration, as described herein. Thus, for example, a candidate agonist can be present in medium in which neurons are cultured, in the presence of nerve growth factor, and assessed for its effect on degeneration. Agonists of neuron or axon degeneration can be used in the prevention and treatment of diseases or conditions including epilepsy and autism, as well as any disease or condition that may be characterized by the failure of a natural process of axon pruning and degeneration. The agonists may be formulated and administered to subjects in need of such treatment using methods such as those described in section E, above.

G. Articles of Manufacture

In another aspect of the invention, an article of manufacture (e.g., a pharmaceutical composition or kit) containing materials useful for the treatment or prevention of the disorders and conditions described above is provided. The article of manufacture includes a container and a label or package insert on or associated with the container. Suitable containers include, for example, bottles, vials, syringes, etc. The containers may be formed from a variety of materials such as glass or plastic. The container holds a composition that is by itself or when combined with another composition effective for treating or preventing the condition and may have a sterile access port (for example the container may be an intravenous solution bag or a vial having a stopper pierceable by a hypodermic injection needle). At least one active agent in the composition is an inhibitor of the invention. The label or package insert indicates that the composition is used for treating the condition of choice. Moreover, the article of manufacture may include (a) a first container with a composition contained therein, wherein the composition includes an inhibitor of the invention; and (b) a second container with a composition contained therein, wherein the composition includes a further therapeutic agent. The article of manufacture in this embodiment of the invention may further include a package insert indicating that the compositions can be used to treat a particular condition. Alternatively, or additionally, the article of manufacture may further include a second (or third) container including a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Further details of the invention are illustrated by the following non-limiting examples.

H. Examples

As discussed above, neuron or axon degeneration is a common feature of many neurodegenerative diseases and also occurs as a result of injury or trauma to the nervous system. The mechanisms that regulate this active process, however, are just beginning to be understood. Based on studies employing different models of neuron or axon degeneration, it appears that different mechanisms may be involved in this process, depending upon the nature of the disorder or injury. To further characterize the events that regulate neuron or axon degeneration, a library of small molecule compounds targeting known signaling pathways in models of neuron or axon degeneration were screened. Multiple signaling pathways were identified as being necessary for neuron or axon degeneration. Notably, a number of kinases were identified as mediators of neuron or axon degeneration, and further mechanistic studies localized the function of distinct kinases to either the axonal or cell body compartments. These pathways were also studied in other degeneration paradigms with similar results, suggesting common molecular mechanisms leading to neuron or axon self-destruction. These experiments are described in the following Examples.

Example 1

Models of Neuron or Axon Degeneration

Three models of neuron or axon degeneration, which were introduced above in connection with descriptions of assays that can be used to identify and characterize inhibitors of neuron or axon degeneration, as described herein, were used in the experiments described below, including anti-NGF antibody, serum deprivation/KCl reduction, and rotenone treatment assays.

Figure 2:
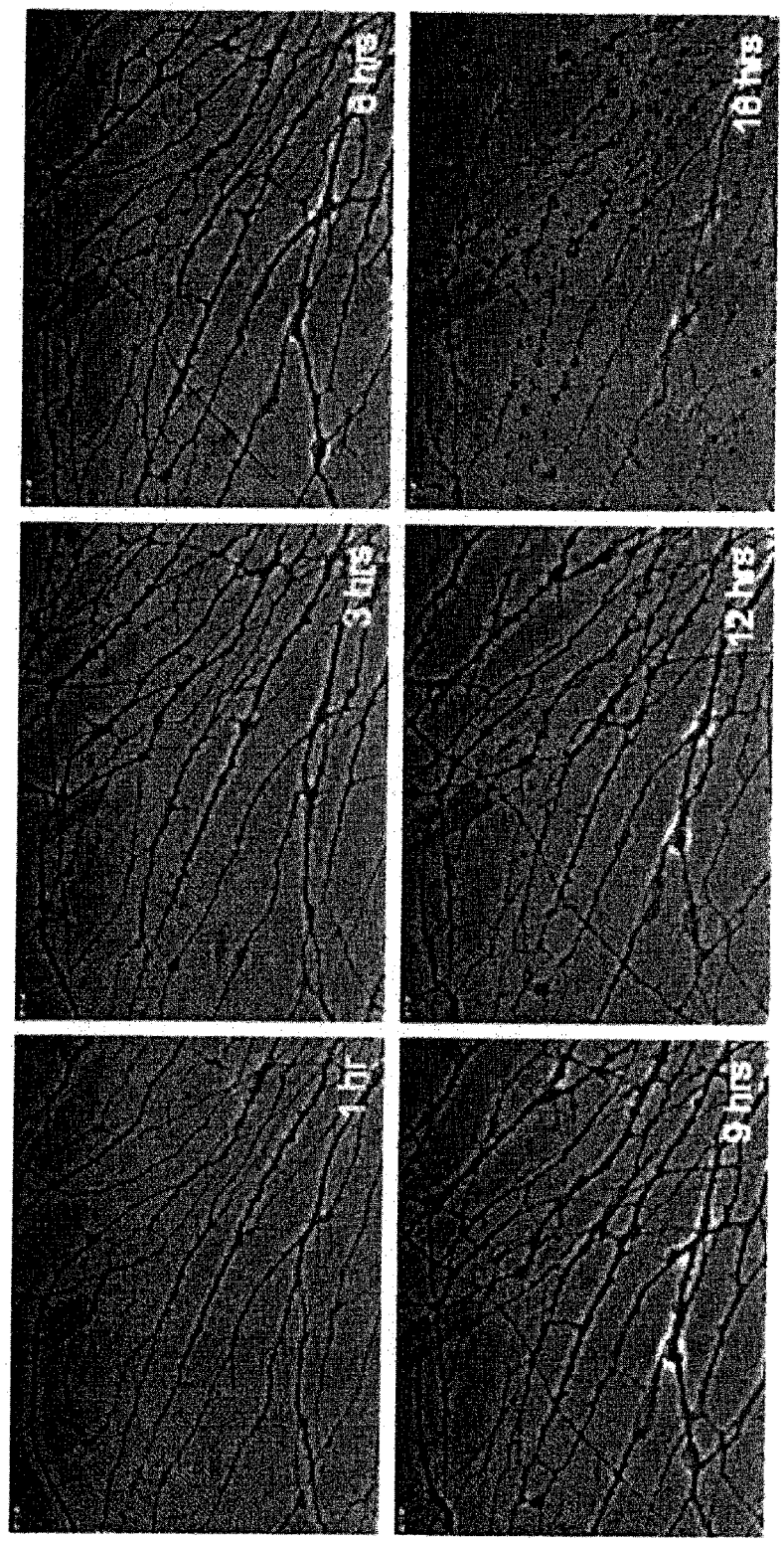
FIG. 2 shows that varicosities form in neurons cultured with anti-NGF antibodies for 1, 3, 6, 9, 12, or 16 hours.
Figure 3:
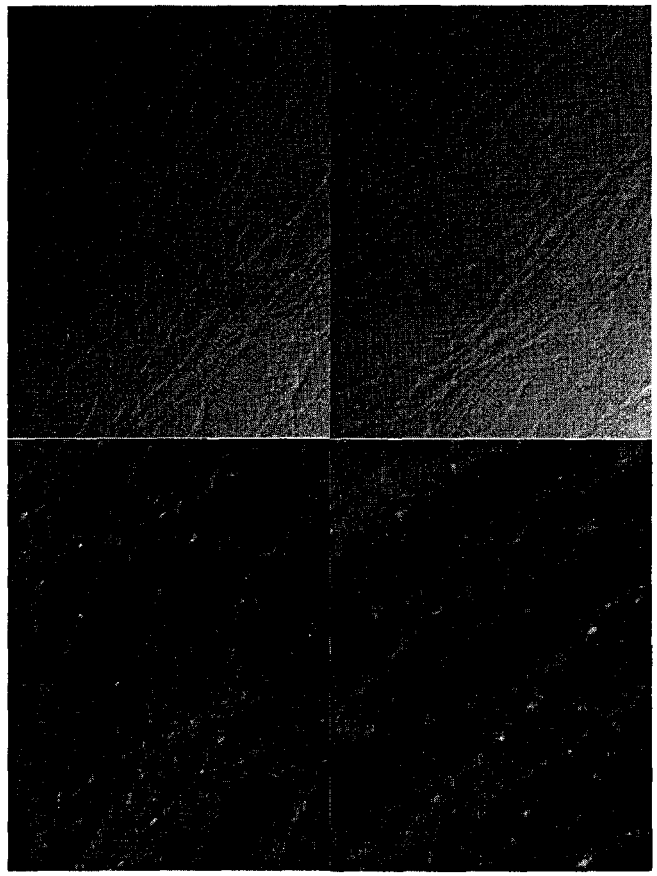
FIG. 3 shows that axons cultured with anti-NGF antibodies for 16 hours lack elongated mitochondria and show accumulation of mitochondria in varicosities.
Figure 4:
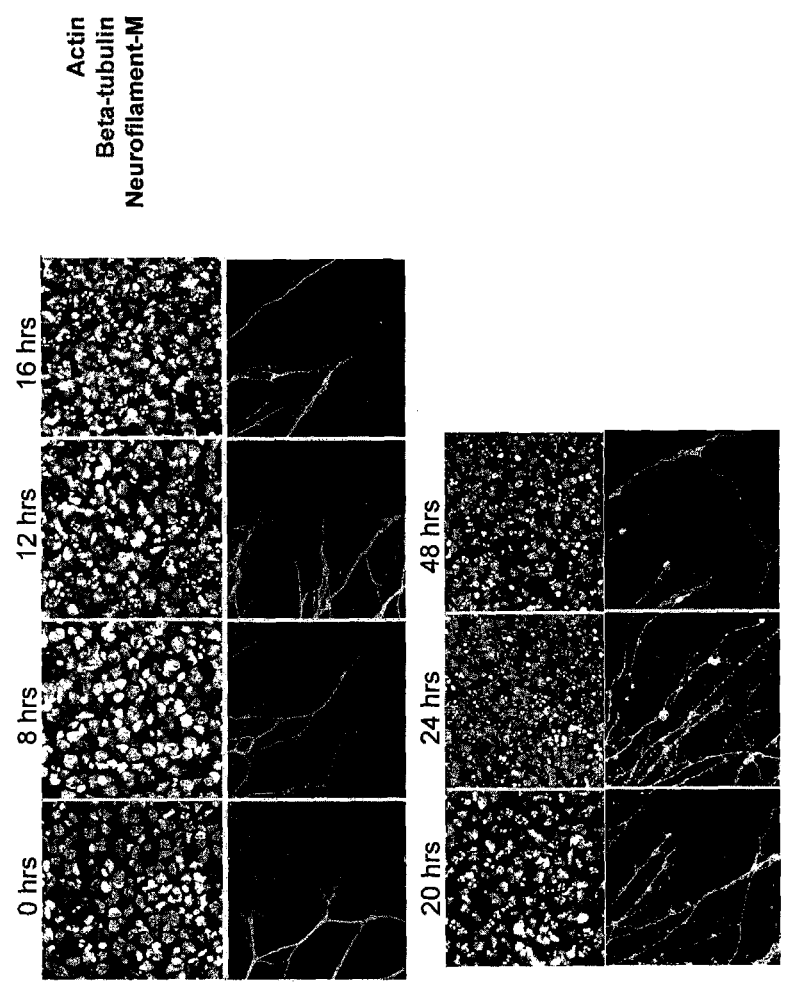
FIG. 4 shows that, in axons cultured with anti-NGF antibodies for 0 to 48 hours, the microtubule network is not disassembled before the actin or neurofilament networks.
Figure 6:
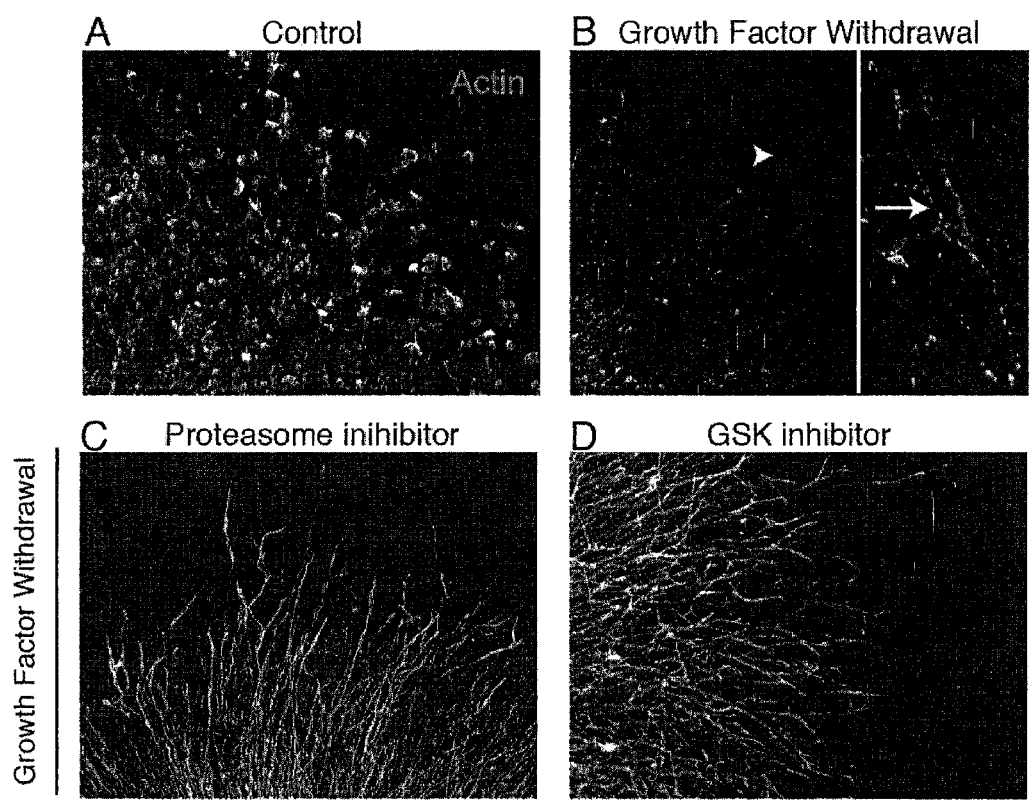
FIGS. 6A-6D show that a proteasome inhibitor and a GSK inhibitor prevent axon degeneration in an anti-NGF antibody-based NGF withdrawal assay.
Figure 7:
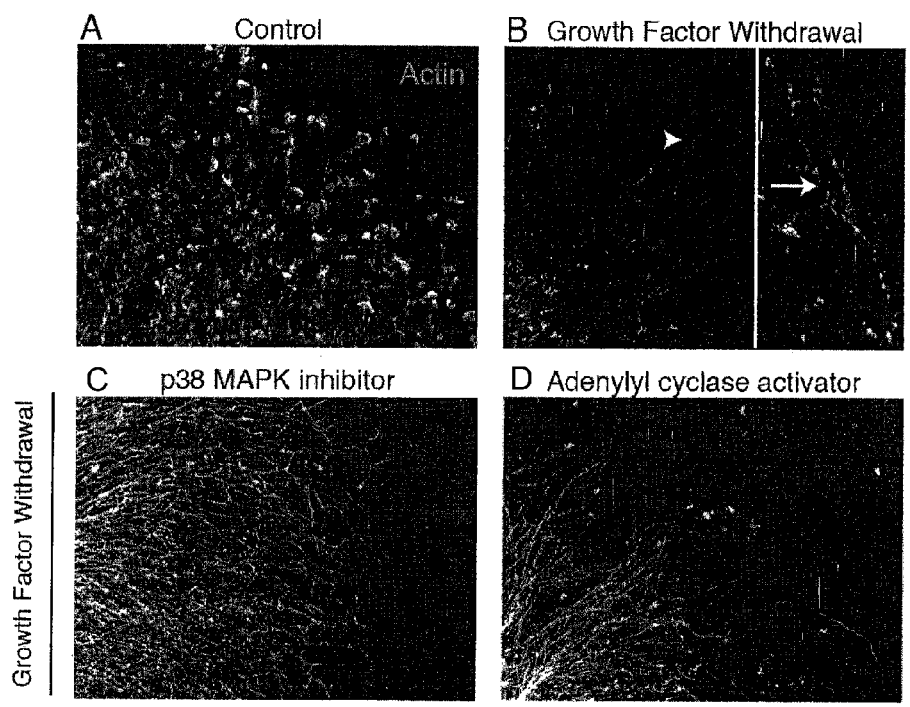
FIGS. 7A-7D show that a p38 MAPK inhibitor and an adenylyl cyclase activator prevent axon degeneration in an anti-NGF antibody-based NGF withdrawal assay.
Figure 8:
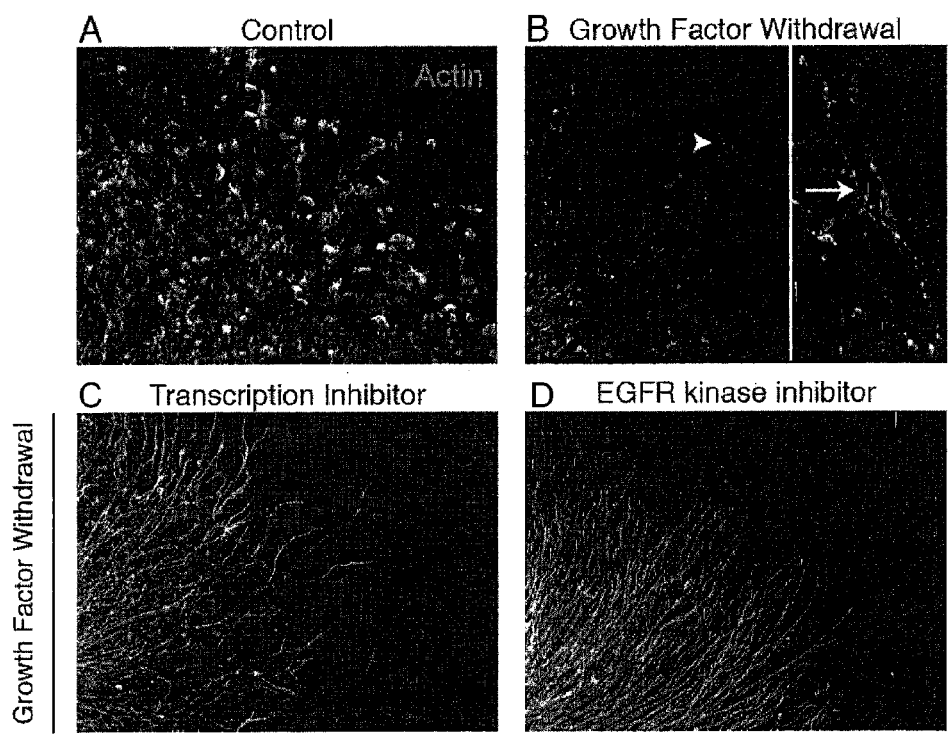
FIGS. 8A-8D show that a transcription inhibitor and an EGFR kinase inhibitor prevent axon degeneration in an anti-NGF antibody-based NGF withdrawal assay.
Figure 9:
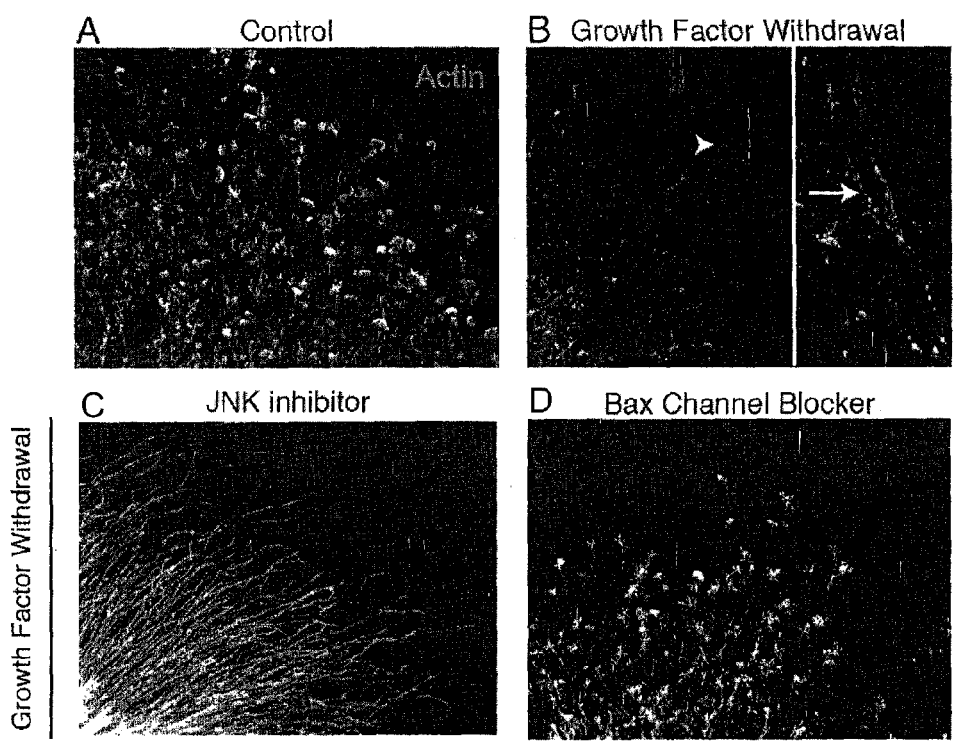
FIGS. 9A-9D show that a JNK inhibitor and Bax Channel Blocker prevent axon degeneration in an anti-NGF antibody-based NGF withdrawal assay.

As described above, treatment of cultured nerves with NGF results in proliferation of axons, while treating such nerves with anti-NGF antibodies results in axon degeneration (FIG. 1). Treatment of neurons with anti-NGF antibodies leads to several different morphological changes that are detectable by microscopy. For example, varicosities formed in nerves cultured with anti-NGF antibodies before axon fragmentation and, in some cases, appeared to burst (FIG. 2). In another example, axons cultured with anti-NGF antibodies lacked elongated mitochondria and showed accumulation of mitochondria in varicosities, suggesting that axon transport is blocked. A significant number of mitochondria were still active within hours of axon fragmentation (FIG. 3). A further example relates to cytoskeletal disassembly. After axotomy, the mictrotubule network disassembles prior to the actin and neurofilament networks. In contrast, in the NGF withdrawal model, the microtubule network was not disassembled before the actin or neurofilament network (FIG. 4).

Another model of axon degeneration is Wallerian degeneration, which is induced by the occurrence of a lesion in the axon that separates it from the cell body (FIG. 5) (see, e.g., Raff et al., *Science* 296(5569):868-871, 2002). In Wallerian Degeneration Slow (Wld$^S$) mutants, axon degeneration was significantly delayed, as compared to wild type controls (FIG. 5; Araki et al., *Science* 305(5686):1010-1013, 2004). The effect of the Wld$^S$ mutant is evidence of the existence of an axonal self-destruction mechanism, which is weakened in the Wld$^S$ mutant. Wld$^S$ protected axons after NGF withdrawal, but did not prevent apoptosis.

Additional information concerning the anti-NGF antibody, serum deprivation/KCL reduction, and rotenone treatment assays is provided in Examples 2-4 (anti-NGF antibody), 7 (serum deprivation/KCl reduction), and 8 and 9 (rotenone treatment).

Example 2

Screen for Inhibitors of Neuron or Axon Degeneration

The anti-NGF antibody model described above in Example 1 was used in a screen for inhibitors of neuron or axon degeneration. A library of more than 400 small molecules (Tocris Bioscience) was tested to see which, if any, modulate degeneration observed in the presence of anti-NGF antibodies.

Methods and Materials

Mouse E13.5 embryos were dissected and placed into L15 medium (Invitrogen). The spinal cord was dissected out from the embryos with DRGs attached. The spinal cords with DRGs attached were placed into L15 medium+5% goat serum (Gibco) on ice. The DRGs were removed using a tungsten needle and the remaining spinal cord was disposed of. Eight well slides were filled with N3-F12 solution (23 ml Ham's F12, 1 ml N3 supplement, and 1 ml 1 M glucose) to which was added 25 ng/ml NGF (Roche). (N3 supplement was made by dilution of N3 100× concentrate, which was made by mixing the following ingredients, in the following order: 5.0 ml Hank's buffered saline solution (HBSS; Ca, Mg free; Invitrogen), 1.0 ml bovine serum albumin (10 mg/ml in HBSS=150 µm), 2.0 ml Transferrin (T1147-1G, human, 100 mg/ml in HBSS=1.1 mM), 1.0 ml sodium selenite (S9133-1MG, 0.01 mg/ml in HBSS=58 µM), 0.4 ml putrescine dihydrochloride (P5780-5G, 80 mg/ml in HBSS=500 mM), 0.2 ml progesterone (P8783-5G, 0.125 mg/ml in absolute ethanol=400 µM), 0.02 ml corticosterone (C2505-500MG, 2 mg/ml in absolute ethanol=5.8 mM), 0.1 ml triiodothyonine, sodium salt (T6397-100MG, 0.2 mg/ml in 0.01 N NaOH=300 µM), 0.4 ml insulin (16634-250MG, bovine pancreas, 241 U/mg, 25 mg/ml in 20 mM HCl=4.4 mM), for a total volume of 10.02 ml (can be stored at −20° C.). An N3 supplement stock was made by combining the following: 10 ml Pen/Strep (100×, Gibco), 10 ml glutamine (200 mM, Gibco), 10 ml MEM vitamins (100×, Gibco), 10 ml N3 concentrate (100×, see above), for a total volume of 40 ml. The mixture was filter sterilized using a 0.22 µm filter, and 1-2 ml aliquots were stored at −20° C.).

The DRGs were sectioned into halves, and placed in the center of each well of an 8-chamber slide (BD Biocoat PDL/Laminin coated glass, Becton Dickinson). The DRGs were permitted to attach to the slide at room temperature for 5-10 minutes, followed by an overnight incubation at 37° C. Inhibitors of choice were added at a concentration of 100 µM (top row) or 10 µM (bottom row) 1 hour before adding anti-NGF antibodies. The anti-NGF antibodies were added to the right half of the slide (4 wells) at a concentration of 25 µg/ml. After incubation for 20 hours at 37° C., the slides were fixed with 30% sucrose/8% paraformaldehyde (PFA) by adding 250 µl of the fix solution directly to the 250 µl of culture medium. (To make the 30% sucrose/8% PFA solution, the following ingredients were added to a 600 ml beaker including a stir bar: 250 ml 16% PFA (cat #15710-S, Electron Microscopy Sciences), 50 ml 10×PBS pH 7.4, and 150 g sucrose. The solution was mixed under low heat until dissolved, and then 6-8 drops of 1 M NaOH were added to bring the pH to 7.4. The volume was then brought to 500 ml with water in a graduated cylinder. The solution was mixed well, placed in aliquots, and frozen.) The slides were fixed for 30 minutes, followed by washing once with PBS. All cells were labeled with an actin stain (Alexa-568 conjugated phalloidin; 1:40; Invitrogen), a membrane dye (DiO; 1:200; Invitrogen), and a DNA stain (Hoechst 33258; 1:10,000; Invitrogen) in 0.1% Triton and 1% goat serum for 2 hours at room temperature. The stain solution was removed and the slides were washed 1× with PBS, and coverslipped with 130 µl of mounting medium (Fluoromount G; Electron Microscopy Sciences) and 24×60 mm no. 1 coverslips (VWR).

Results

Figure 10:
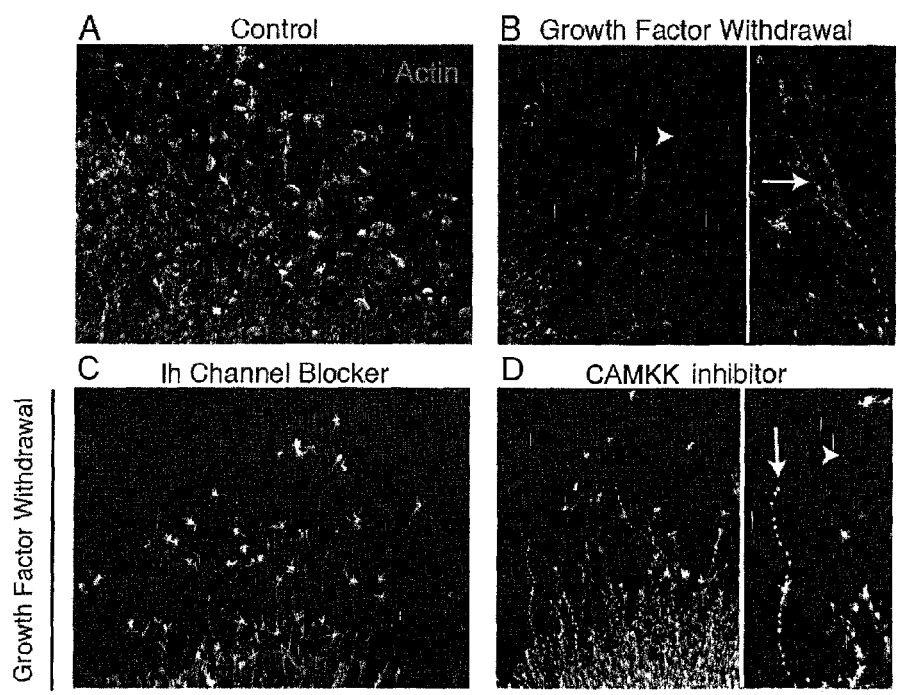
FIGS. 10A-10D shows that an Ih channel blocker and a CAMKK inhibitor prevent axon degeneration in an anti-NGF antibody-based NGF withdrawal assay.

In these experiments, control neurons (as visualized by actin staining) underwent significant degeneration upon NGF withdrawal. In contrast, in the presence of certain small molecules, axon integrity was maintained upon NGF withdrawal. FIGS. 6-10 show the results of these studies for a proteasome inhibitor and a GSK inhibitor (FIG. 6), a p38 MAPK inhibitor and an adenylyl cyclase activator (FIG. 7), a transcription inhibitor and an EGFR kinase inhibitor (FIG. 8), a JNK inhibitor and a Bax channel blocker (FIG. 9), and an Ih channel blocker and a CaMKK inhibitor (FIG. 10). Examples of specific compounds found to protect against neurodegeneration, and corresponding targets, are shown in Table 5, which is similar to Table 2, above, except that it further includes a column with comments concerning observations made with respect to some of the compounds.

TABLE 5

| Target | Compounds | Comments |
|---|---|---|
| Proteasome | MG132 | |
| GSK3β | SB 415286 | |
| | GSK3β inhibitor I | |
| | GSK3β inhibitor VII | |
| | GSK3β inhibitor VIII | |
| | GSK3β inhibitor XII | |
| | Lithium Chloride | |
| P38 MAPK | SB 202190 | |
| | SB 239063 | |
| | SB 239069 | Filopodia enriched growth cones present |
| | SB 203580 | |
| | SB 203580 HCI | Partial |
| EGFRK | AG 556 | |
| | AG 555 | |
| | AG 494 | |
| | PD168393 | |
| | Tyrphostin B44 | Partial |
| | Tyrphostin B42/AG 490 | |
| PI3K | LY294002 (Calbiochem. Cat. No. 440202) | |
| Cdk5 | Roscovitine | |
| Adenylyl cyclase | Forskolin | |
| | NKH 477 | Partial |
| Transcription | Actinomycin D | |
| JNK | SP600125 | |
| Bax Channel | Bax Channel Blocker | Cell bodies detach |
| Ih Channel | ZD7288 | |
| CAMK | STO-609 | Partial |
| Protein Synthesis | Anisomycin | |
| | Cycloheximide | |

Example 3

Characterization of Inhibitors with Respect to Timing of Addition After Growth Factor Withdrawal Studies were conducted to assess the activities of the inhibitors when added at various time points after NGF withdrawal. In particular, experiments were carried out to determine the latest time-point after the start NGF-deprivation at which candidate kinases can be inhibited to stop axon degeneration.

Methods and Materials

Primary cells used in this study were Charles River CD-1 E13 Dorsal Root Ganglia (DRG). The cells were maintained in N3/F12 (+25 ng/ml NGF) medium (Ham's F12 (23 ml), N3 supplement (1 ml), glucose (1 ml of 1 M glucose stock), 25 ng/ml Nerve Growth Factor 2.5 S, mouse (Roche 11362348001) in Ham's F12 (stock: 50 µg/ml-80° C.), filter-sterilized prior to use). The experiments also employed BD Biocoat PDL/Laminin coated glass 8 well chamber slides (BD 354688), and 24×60 mm No. 1 coverslips (VWR 48393 106).

Embryos were dissected in L15 medium (the dissection tools were soaked in 70% isopropanol, and dishes were set up on ice: 10 cm dishes (4 embryos per dish) and one 6 cm dish for spinal cords). E13.5 spinal cords were extracted into DMEM+10% FBS. >128 DRGs were detached from the spinal cord and sectioned into halves with a tungsten needle. 8 well slides were filled with 250 µl N3/F12 (25 ng/ml NGF). Sectioned DRGs (~4 per well) were placed in a 5 µl volume. Attachment was allowed for ~10 minutes at room temperature, and then the DRGs were incubated at 37° C. overnight. The following conditions were used to test the inhibitors. 25 µg/ml anti-NGF antibody was added at 22 hours. Inhibitors were added at T=0, 1, 3, 6, 9, and 12 hours after anti-NGF addition (1.25 µl inhibitors added; 5 µl aliquot from mass mix into −20° C.; 18 µl in 12 µl DMSO; 6 µl in 24 µl DMSO; 18 µl in 12 µl DMSO; 9 µl in 21 µl DMSO; 6 ml in 24 µl DMSO). Mixing was done by addition of the inhibitors and light shaking. The controls were +/−Anti-NGF (+1.25 µl DMSO), and the experiments were done in duplicate.

After 25 hours, 250 µl 30% sucrose/8% PFA was added to the 250 µl of culture medium for 30 minutes. Slides were washed with 1×PBS (stop: 4° C.). Immunofluorescence was carried out as follows. First, blocking was carried out in 5% BSA/0.2% Triton for 30 minutes at room temperature. Primary antibodies (Tuj1 (1:1,000)) were incubated with the slides overnight in 2% BSA at 4° C. Slides were washed with 1×PBS and add a secondary antibody (Goat anti-mouse 488; 1:200) was added. Slides were incubated with the secondary antibody for 1 hour at room temperature in the dark. Slides were washed in 1:10,000 Hoescht in PBS for 10 minutes, washed in PBS in a glass copland for 5 minutes, smacked on a towel to mildly dry, coverslipped with 200 µl of fluoromount G, and stored at 4° C. Pictures were taken all at the same settings (i.e., exposure times). The rate of degeneration was assessed based on detachment of axons from cell bodies as well.

Results

Figure 11:
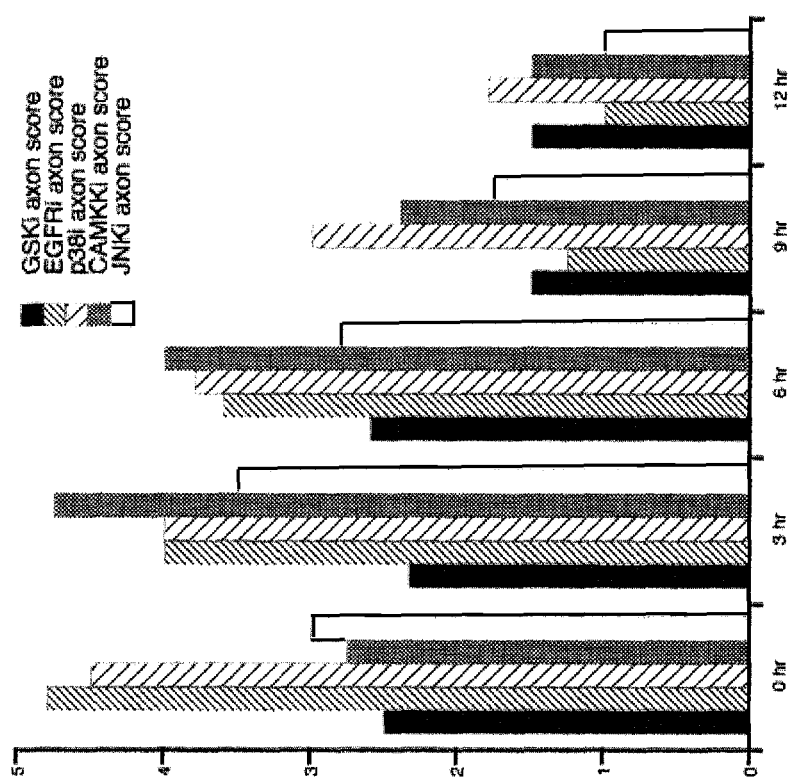
FIG. 11 is a graph showing the activities of inhibitors of GSK3 (30 μM SB415286), EGFR kinase (10 μM AG555), p38 MAPK (30 μM SB239063), CAMKK (15 μM STO-609), and JNK (10 μM SP600125) when added at the time of NGF withdrawal (t=0) or at 3, 6, 9, or 12 hours after NGF withdrawal.

These studies show that the inhibitors are protective even when added several hours (3, 6, 9, and 12 hours) after NGF withdrawal (FIG. 11). Axon score is a score of axon health on a scale from 1 to 10 (0=looks like anti-NGF control; 10=looks like NGF control; 5=looks like kinase inhibitor when added at 0 hours. The inhibitors used in these studies are listed in Table 6.

TABLE 6

| Anti-NGF Inhibitors (stock: 10 mM in DMSO) | | | | |
|---|---|---|---|---|
| Target/ Action | Inhibitor | Concentration | Cell Body Compartment | Axon Compartment |
| 1) GSK3 inhibitor | SB415286 | 30 µM | Yes (5) | No (5) |
| 2) EGFR kinase inhibitor | AG555 | 10 µM | No (4) | Yes (4) |
| 3) p38 MAPK inhibitor | SB239063 | 30 µM | No (3) | Yes (3) |
| 4) CAMKK inhibitor | STO-609 | 15 µM | No (1) | Yes (1) |
| 5) JNK inhibitor | SP600125 | 10 µM | Yes (1) | Yes (1) |

Example 4

Characterization of Compounds with Respect to Localized Degeneration

Figure 12:
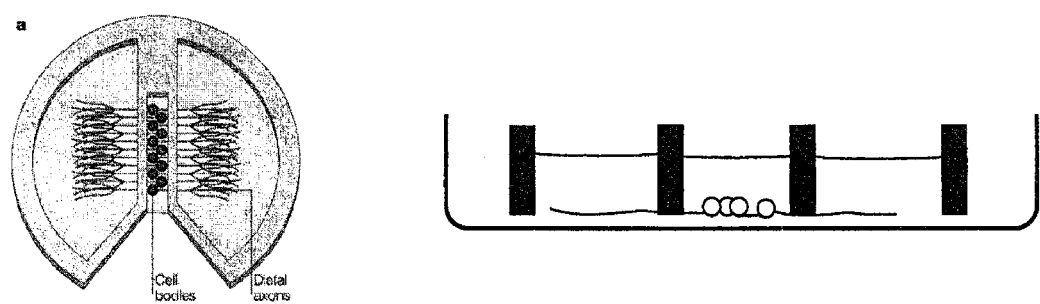
FIG. 12 illustrates a Campenot chamber, in which somal (cell body) and axonal environments are separated.
Figure 13:
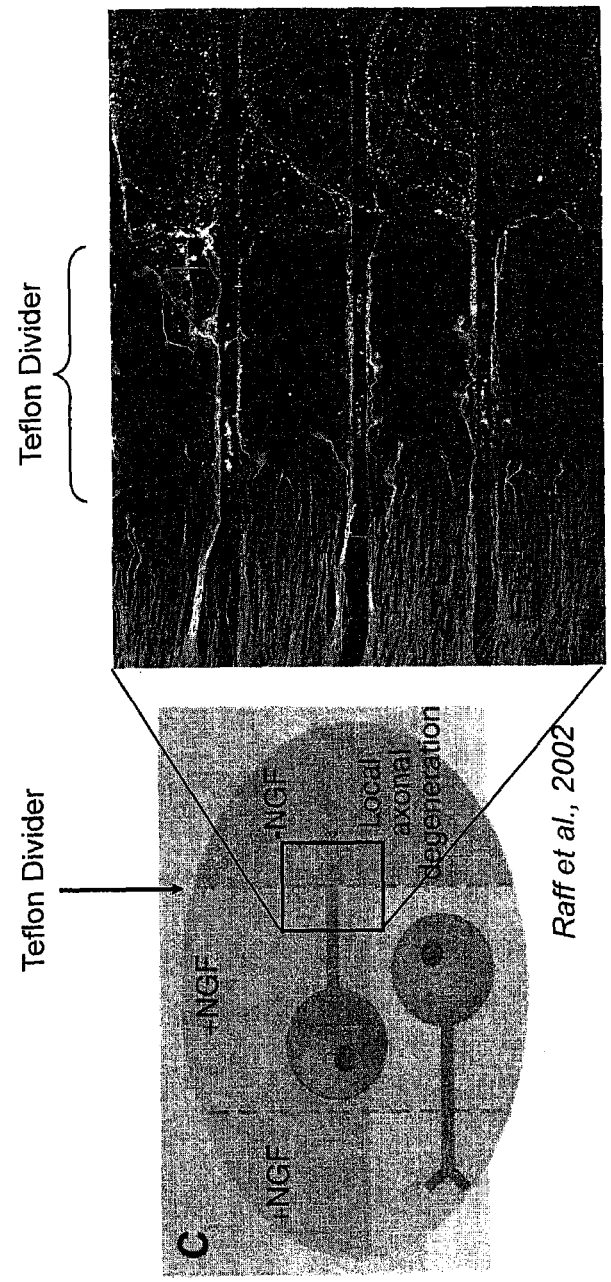
FIG. 13 shows that axon degeneration is localized and proceeds without apoptosis in Campenot chamber studies in which NGF withdrawal took place in the axon-containing chamber. Degeneration is visualized by tubulin immunofluorescence.
Figure 14:
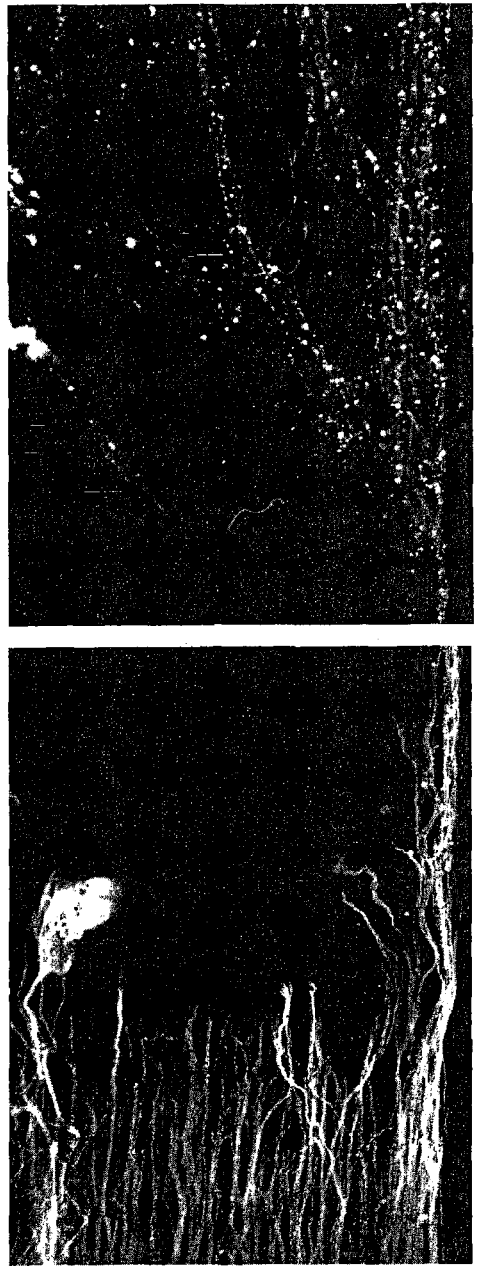
FIG. 14 shows that there are no signs of degeneration in the cell body compartment in the Campenot chamber-based assay illustrated in FIG. 13.

Campenot chambers were used to further analyze compounds identified as inhibiting axon degeneration in Example 2. Campenot chambers allow the separation of somal and axonal environments, and permit the induction of localized degeneration (see FIG. 12 and, e.g., Zweifel et al., *Nat. Rev. Neurosci.* 6(8):615-625, 2005). In such chambers, axon degeneration is localized and proceeds without apoptosis (FIGS. 13 and 14).

Materials and Methods

Teflon dividers (Tyler Research) were cleaned by washing in water and wiping them clean of any residual grease. Dividers were then soaked in Nochromix (Godax Laboratories)/sulfuric acid overnight, rinsed five times in distilled and autoclaved water (SQ water), boiled for 30 minutes, and then air-dried before use.

Mouse laminin (5 μg/ml in sterile filtered water; Invitrogen) was added to PDL coated 35 mm dishes (BD Biosciences) and they were incubated for 1 hour at 37° C., followed by two rinses in SQ water. The dishes were vacuum-dried and then air-dried in a laminar flow hood for 15 minutes. Prepared dishes were then scored with a pin rake (Tyler Research). Fifty microliters of NBM+MC solution containing NGF was applied across the resulting score tracks (The solution was made as follows: 1750 mg of methycellulose was combined with 480 ml of Neurobasal (Invitrogen), to which was added 4.5 ml penicillin/streptomycin, 7.5 ml L-glutamine, 10 ml B-27 serum-free supplement (Invitrogen); the solution was mixed for one hour at room temperature, overnight at 4° C., and one further hour at room temperature; the solution was then filter sterilized, and 50 ng/ml NGF (Roche) was added prior to use). High vacuum grease (VWR) was added to each Teflon divider under a dissection scope. The laminin coated PDL dishes were inverted and dropped onto the Teflon divider, with additional pressure added by use of a toothpick in the non-track-containing regions. Dishes were incubated for 1 hour at 37° C. Five hundred microliters of NBM+MC (50 ng/ml NGF) solution was added to each of the side compartments, and a grease barrier was added in front of the center cell slot.

Free E13.5 spinal cords were dissected from mouse embryos and placed into NBM+MC (25 ng/ml NGF) solution. DRGs were detached from the spinal cord with a tungsten needle. An NBM+MC-lubricated P200 pipette was used to move DRGs into a 1.5 ml tube. DRGs were pelleted with a tabletop centrifuge for 30 seconds. The supernate was discarded and 0.05% Trypsin/EDTA (cold) was added. The pellet was resolubilized with a pipette and incubated at 37° C. for 15 minutes with constant agitation (650 RPM). The sample was again centrifuged and the supernate discarded. The pellet was resuspended in warm NBM+MC (50 ng/ml NGF) solution and triturated with a flamed glass pipette 20 times, followed by trituration with a fire-bored glass pipette another 20 times. The samples were again centrifuged and the resulting pellets were resuspended in 0.5 ml NBM+MC (50 ng/ml NGF) solution. The cells were diluted to a final concentration of $2.5 \times 10^6$ cells/ml. The cell suspensions were loaded into a 1 ml syringe with a 22 gauge needle. The center slot of the Campenot divider was filled using the syringe (to a volume of at least 50 μl). The Campenot chamber was incubated overnight at 37° C. 2.5 ml NGF+MC (50 ng/ml NGF) solution was added to the center compartment and the grease gate was removed. The outer medium (cell body compartment) was replaced after three days with 2.5 ml NBM+MC medium (with 25 ng/ml NGF). After five days in culture, one distal compartment was washed three times with warmed NBM+MC (no NGF) solution. After the third wash, 500 μl NBM+MC (no NGF) solution was added to the axon compartment in combination with either 0.5% DMSO or an inhibitor. The cell body compartment was replaced with 2.5 ml NBM+MC medium (with 25 ng/ml NGF) containing either 0.5% DMSO or inhibitor.

After 28 hours of anti-NGF antibody treatment, 8% PFA/30% sucrose solution (see above) was added directly to the culture medium at a 1:1 dilution and incubated for 30 minutes. The Teflon divider was removed after the first 15 minutes of addition. The system was washed once with 2.5 ml PBS prior to immunostaining. Neurons were blocked in 5% BSA/0.2% triton in PBS for 30 minutes. The primary antibody Tuj1 (Covance) was added to a final dilution of 1:1000 in PBS containing 2% BSA and incubated overnight at 4° C. The dish was washed once with PBS. The secondary antibody (Alexa 488 goat anti-mouse antibody (Invitrogen)) was added at a final dilution of 1:200 in 2% BSA in PBS and incubated for one hour at room temperature. The dish was washed twice with PBS, and a 22×22 mm coverslip (VWR) was added with 350 μl of fluoromount G (Electron Microscopy Sciences). The neurons were visualized by use of a fluorescence microscope.

Results

Figure 15:
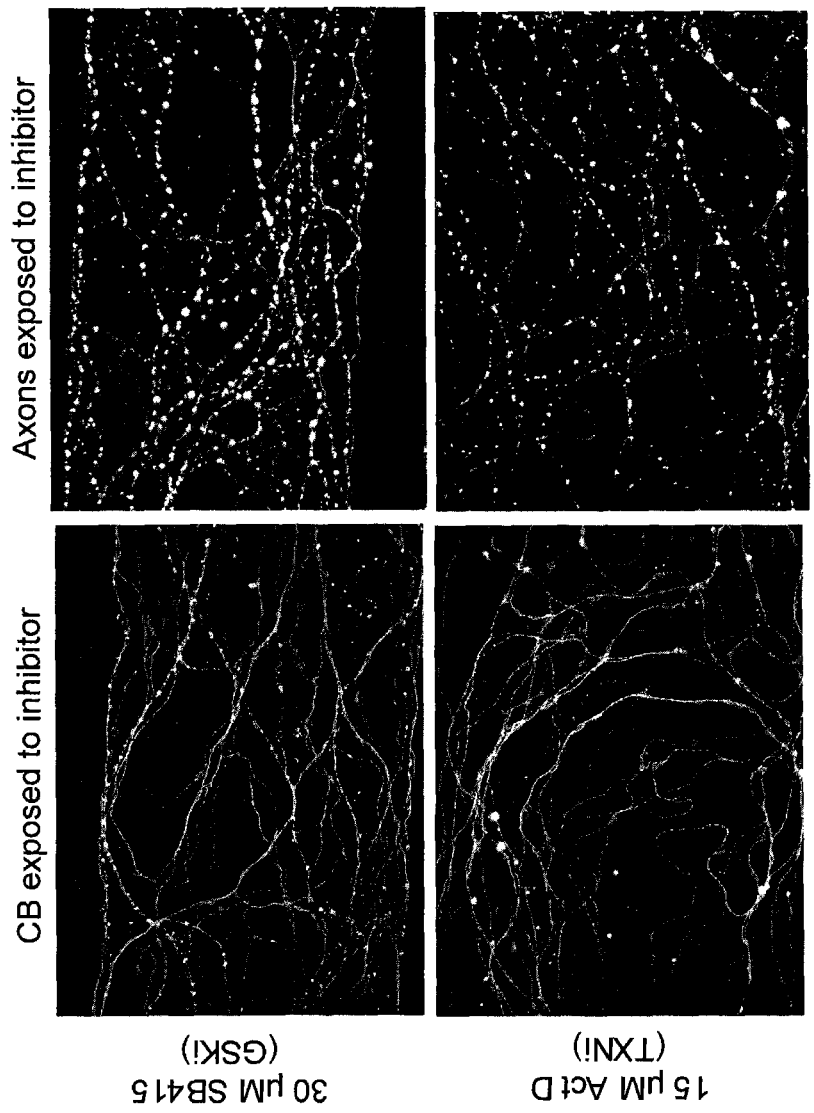
FIG. 15 shows that cell bodies (left panels), but not axons (right panels), in the presence of 30 μM SB415 (GSK inhibitor; GSKi) or 15 μM Act D (transcription inhibitor; TXNi) were protected from local degeneration.
Figure 16:
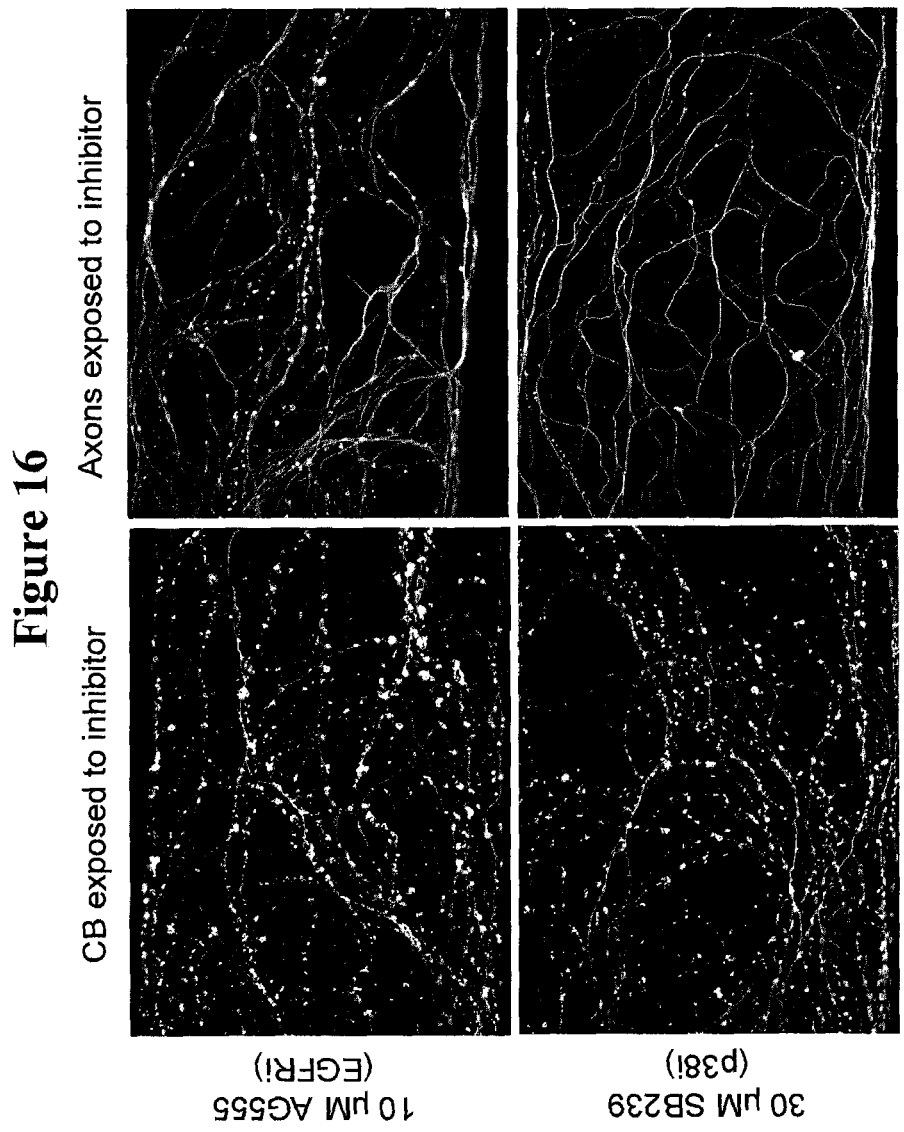
FIG. 16 shows that axons (right panels), but not cell bodies (left panels), exposed to anti-NGF antibodies in the presence of 10 μM AG555 (EGFR inhibitor; EGFRi) or 30 μM SB239 (p38 inhibitor; p38i) were protected from local degeneration.
Figure 17:
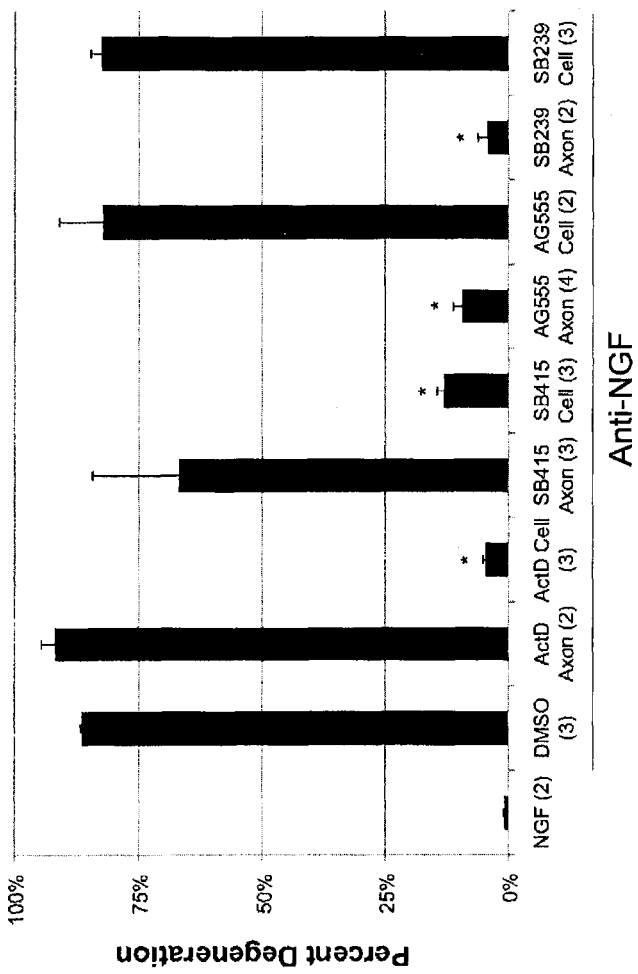
FIG. 17 is a graph showing quantification of axon degeneration in Campenot chambers in which anti-NGF antibodies were added to the axonal environment in the presence or absence (DMSO) of 15 μM actinomycin D (ActD), 30 μM SB415286 (SB415), 10 μM AG555, or 30 μM SB239063 (SB239) in the axonal (Axon) or the somal environment (Cell).

As described above, E13.5 DRGs were isolated and grown for 5 days in a Campenot chamber. Fifty μg/ml anti-NGF was added to the experimental axon compartment, with an inhibitor added either to the axon compartment (together with the NGF antibody), or the cell body compartment, and the axons were allowed to degenerate for 28 hours. Another axon compartment was maintained in NGF as a control. As shown in FIGS. 15 and 16, when cell bodies were exposed to SB415 (GSKi) or Act D (transcription inhibitor), or when axons were exposed to AG555 (EGFRi) or SB239 (p38i), axons deprived of NGF did not degenerate. In contrast, SB415 (GSKi) or Act D (transcription inhibitor) in the NGF-deprived axon compartment, or AG555 (EGFRi) or SB239 (p38i) treatment in the cell body compartment, failed to prevent degeneration, suggesting that signaling in local axon degeneration is not limited to the axon segment being lost; some inhibitors are most effective when applied to the cell body, and others to the axon. Quantification of these results is shown in FIG. 17. Table 7 provides a summary of axon degeneration data from Campenot chambers.

TABLE 7

Inhibitors in Axon vs. Cell Body Compartment

| Target/Action | Inhibitor | Concentration | Cell Body Compartment | Axon Compartment | Cellular IC$_{50}$ |
|---|---|---|---|---|---|
| Transcription inhibitor | Actinomycin D | 15 μM | Yes (4) | No (4) | |

TABLE 7-continued

Inhibitors in Axon vs. Cell Body Compartment

| Target/Action | Inhibitor | Concentration | Cell Body Compartment | Axon Compartment | Cellular IC$_{50}$ |
|---|---|---|---|---|---|
| Protein synthesis inhibitor | Cycloheximide | 5 µM | Yes (2) | No (2) | |
| Proteasome inhibitor | MG132 | 0.5 µM | Yes (1) | No (1) | |
| GSK3 inhibitor | SB415286 | 30 µM | Yes (5) | No (5) | 10 µM$^a$ |
| | GSK3 inhibitor XI | 30 µM | Yes (2) | No (2) | |
| | AR-A014418 | 20 µM | Yes (1) | No (1) | |
| Ih channel blocker | ZD7288 | 5 µM | Yes (3) | No (3) | |
| ErbB kinase inhibitor | AG555 | 10 µM | No (4) | Yes (4) | 5 nM$^b$ |
| | PD168393 | 5 µM | No (1) | Yes (1) | 100 nM$^c$ |
| p38 MAPK inhibitor | SB239063 | 30 µM | No (3) | Yes (3) | 0.35 µM$^d$ |
| | | 5 µM | No (1) | Yes (1) | |
| CAMKK inhibitor | STO-609 | 15 µM | No (1) | Yes (1) | 3 µM$^e$ |
| Adenylyl cyclase activator | Forskolin | 3 µM | Yes (2) | Yes (2) | |
| JNK inhibitor | SP600125 | 5 µM | Yes (1) | Yes (1) | |

(Note: IC$_{50}$ information in Table 7 is from published sources and some values were generated with non-neuronal cell types)
$^a$Cross et al., *J. Neurochem.* 77(1): 94-102, 2001; total GSK-3 activity by in vitro peptide assay in cerebellar granule neurons.
$^b$Fry et al., *Proc. Natl. Acad. Sci. U.S.A.* 95(20): 12022-12027, 1998; heregulin induced tyrosine phosphorylation in MDA-MB-453 cells.
$^c$Bose et al., *Proc. Natl. Acad. Sci. U.S.A.* 103(26): 9773-9778, 2006; protein tyrosine phosphorylation in 3T3-Her2 cells.
$^d$Barone et al., *J. Pharmacol. Exp. Ther.* 296(2): 312-321, 2001; LPS-induced TNF-alpha production in human monocytes.
$^e$Tokumitsu et al., *J. Biol. Chem.* 277(18): 15813-15818, 2002; CaMKK activity after ionomycin stimulation in transfected HeLa cells.

Figure 18:
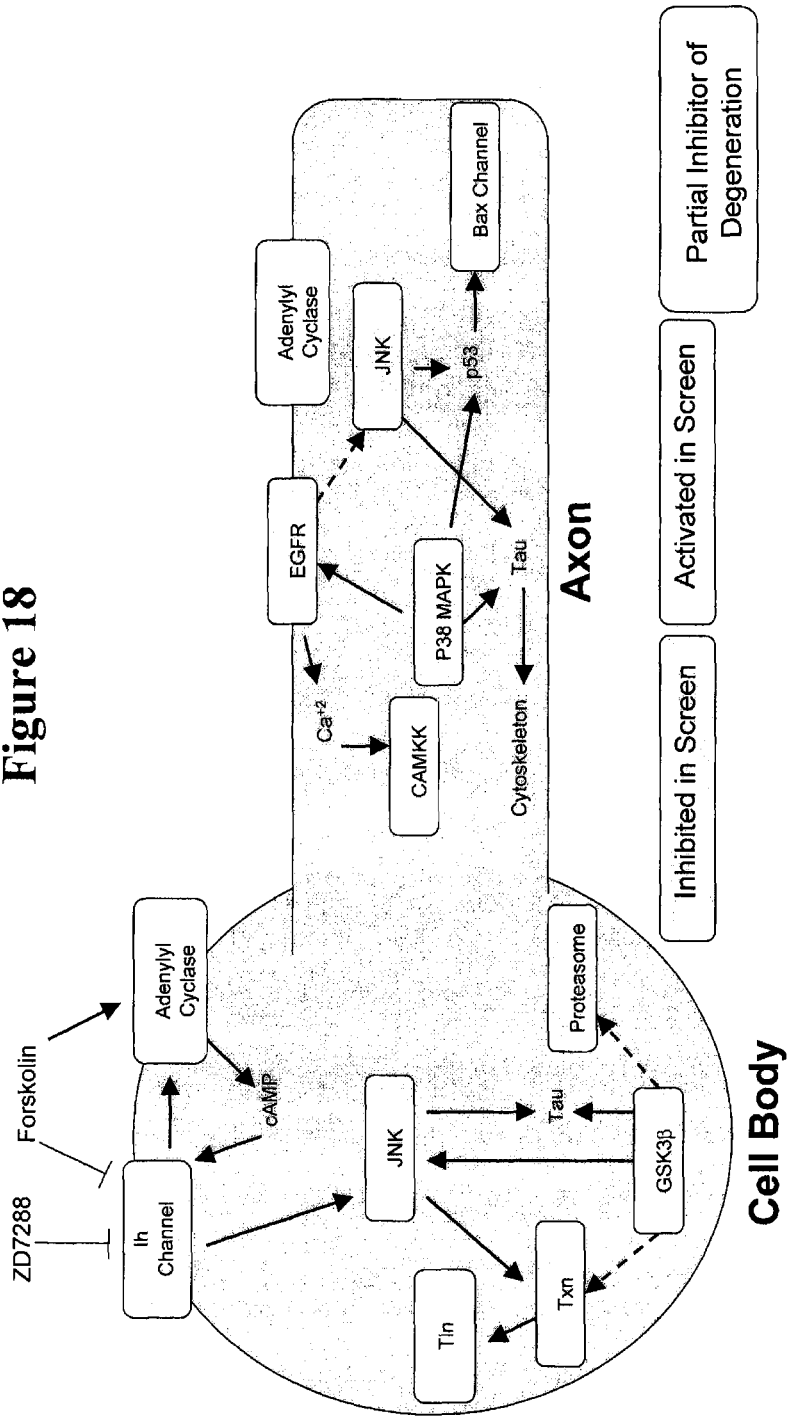
FIG. 18 is a model based on data from the screens described herein.
Figure 19:
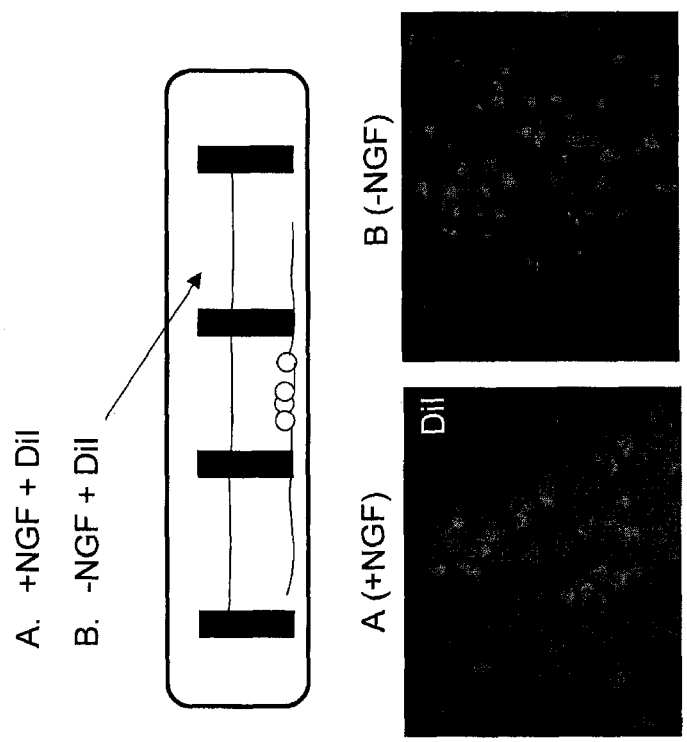
FIG. 19 shows that cell bodies appear smaller when NGF is removed from the axon compartment in a Campenot chamber.
Figure 20:
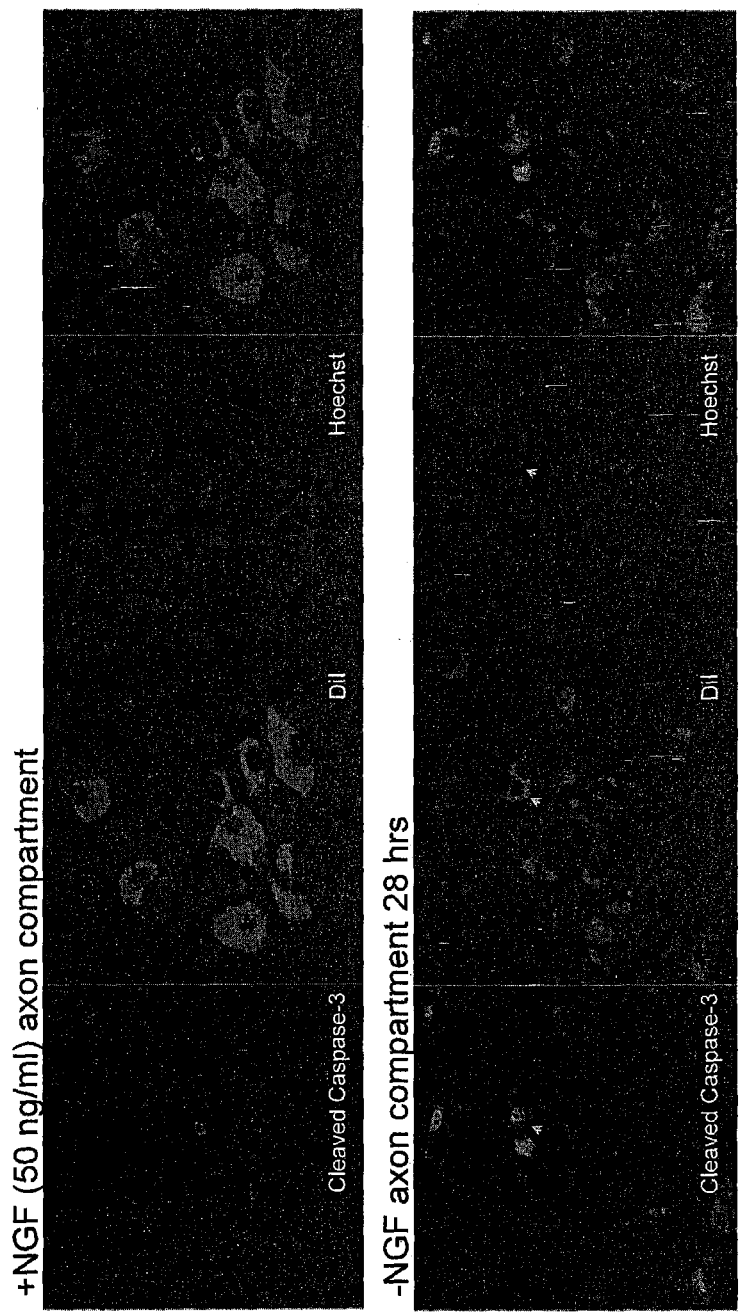
FIG. 20 shows that many neurons deprived of NGF in the axon compartment have increased cleavage of caspase-3 and show nuclear condensation. (Neuron health may be affected by the membrane stain DiI.)
Figure 21:
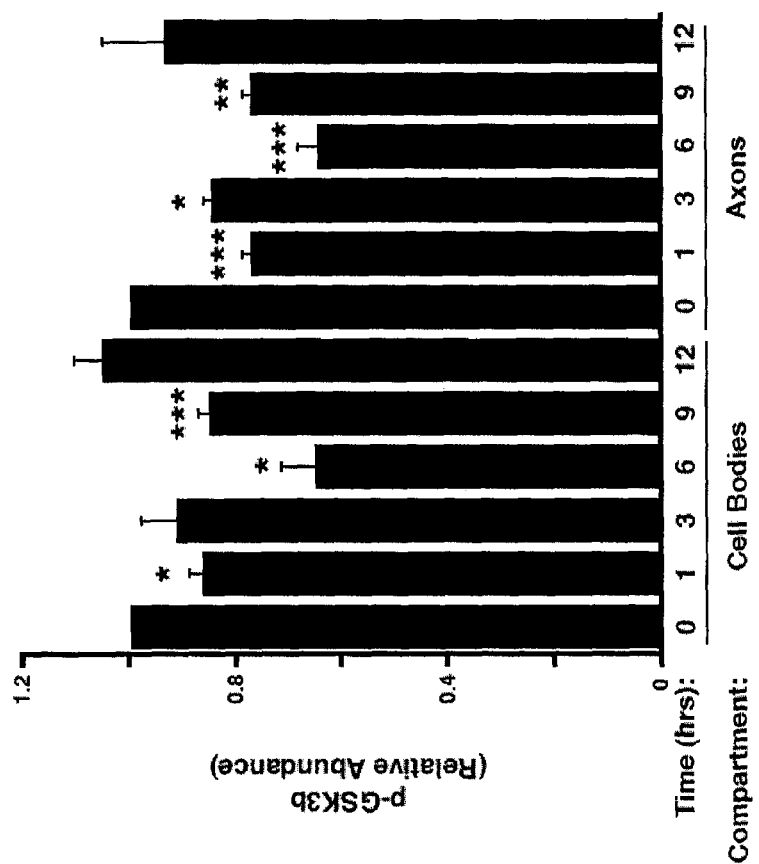
FIG. 21 is a graph showing GSK3 activity (as measured by decreased levels of phosphorylated GSK3β) at the start of NGF withdrawal (t=0) and after 1, 3, 6, 9, and 12 hours of NGF withdrawal in the cell body or axon compartment.
Figure 22:
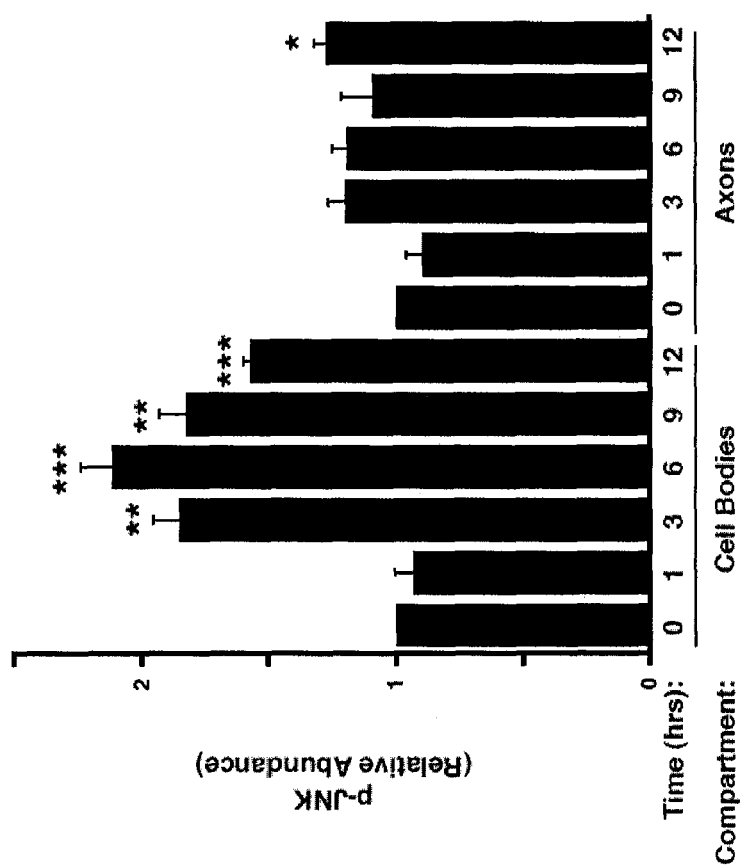
FIG. 22 is a graph showing JNK activity (as measured by increased levels of phosphorylated JNK) at the start of NGF withdrawal (t=0) and after 1, 3, 6, 9, and 12 hours of NGF withdrawal in the cell body or axon compartment.

A model based on data from the screens described above is shown in FIG. 18. Preliminary studies showed that cell bodies appeared smaller when NGF was removed from the axon compartment (FIG. 19), and that many of the neurons locally deprived of NGF were cleaved caspase-3-positive and showed nuclear condensation (FIG. 20). Further studies show that GSK3 (FIG. 21) and JNK (FIG. 22) activities peak 6 hours after NGF withdrawal.

Example 5

Figure 23:
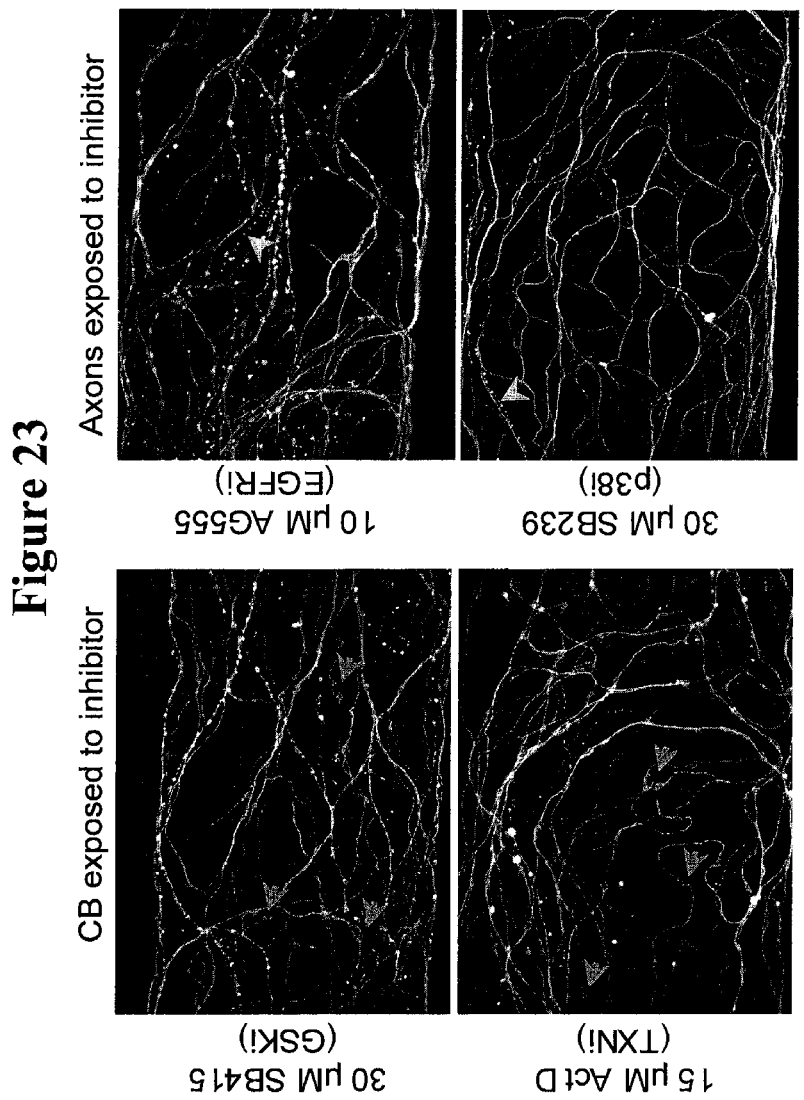
FIG. 23 shows that a large number of axons with varicosities, as well as fragmented axons, were observed when the cell body inhibitors (30 µM SB415 (GSKi) and 15 µM Act D (TXNi)) were added to the cell body compartment. The addition of the axon inhibitors (10 µM AG555 (EGFRi) and 30 µM SB239 (p38i)) to the axon compartment showed fewer varicosities, and the axons seemed to go straight to fragmentation.
Figure 24:
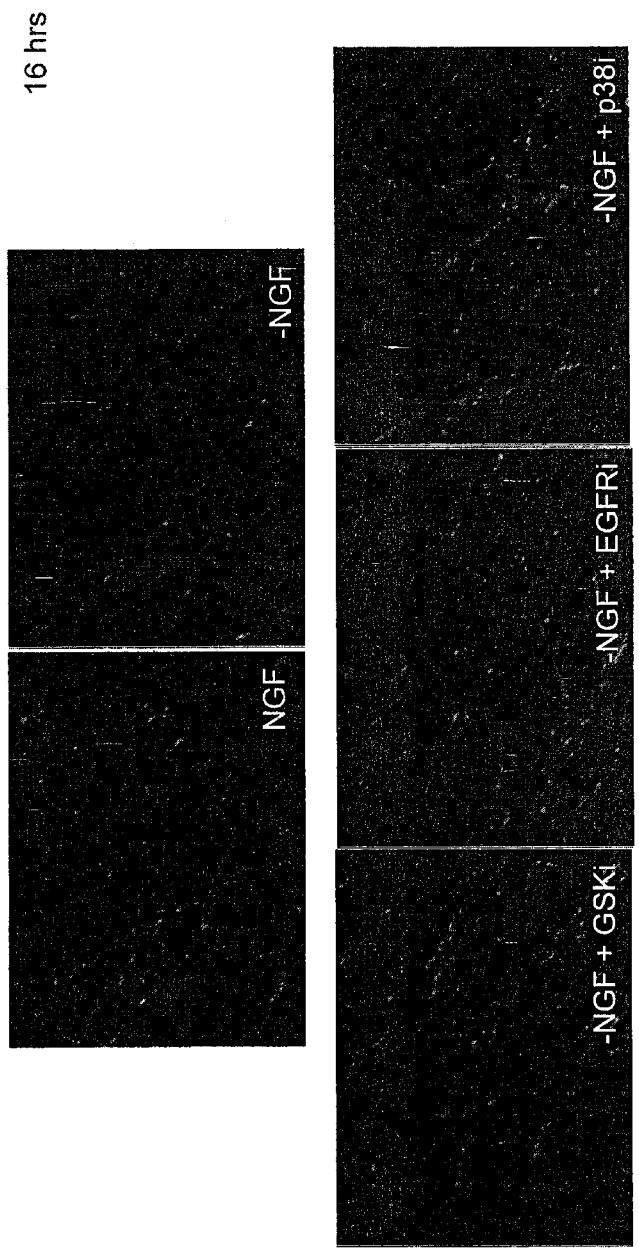
FIG. 24 shows that there may be more functional mitochondria, but still no elongated mitochondria, in NGF-deprived neurons treated with GSK, EGFR, and p38 inhibitors.

Characterization of Compounds with Respect to Particular Phenotypes of Neuron Degeneration With compounds identified above as being cell body inhibitors (SB415 (GSKi) and Act D (transcription inhibitor)) applied to the cell body, and compounds identified as axon inhibitors (AG555 (EGFRi) and SB239 (p38i)) applied to axons, locally deprived axons were observed with respect to formation of varicosities using the Campenot chamber assay described above. A large number of axons with varicosities, as well as fragmented axons, were observed with the cell body inhibitors (FIG. 23). The axon inhibitors showed fewer varicosities, and the axons appeared to proceed straight to fragmentation upon treatment with those inhibitors (FIG. 23). These observations indicate that EGFR and p38 may be upstream of the formation of varicosities. Mitochondrial dysfunction and blockade of axon transport were studied with GSK, EGFR, and p38 inhibitors. As shown in FIG. 24, functional mitochondria were observed, but none were elongated.

Figure 25:
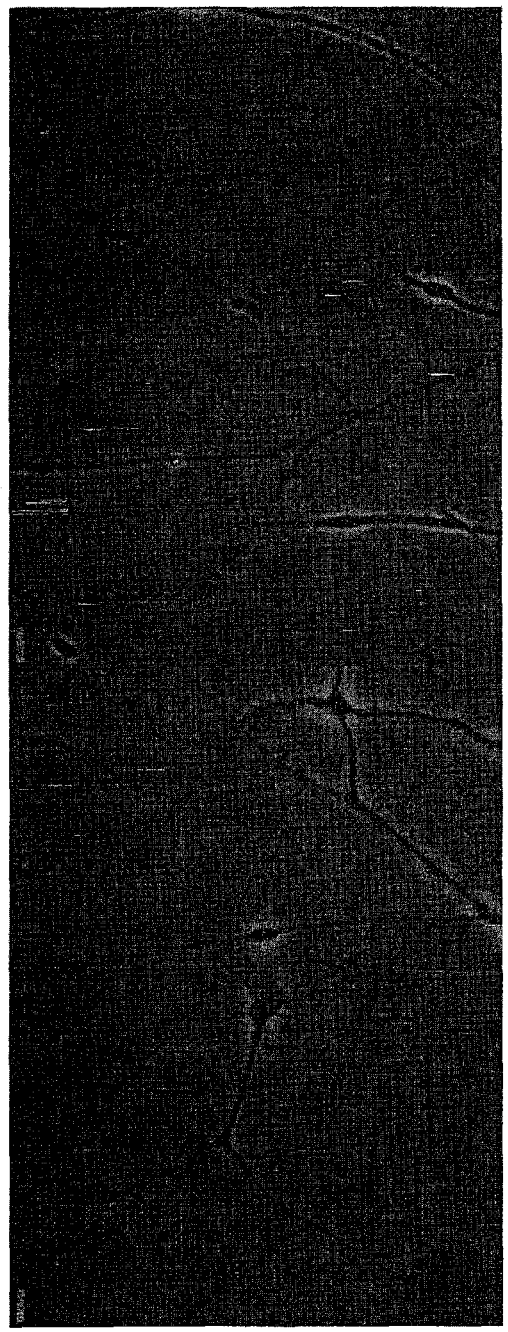
FIG. 25 shows that the GSK inhibitor SB415 can delay axon degeneration after lesion.
Figure 26:
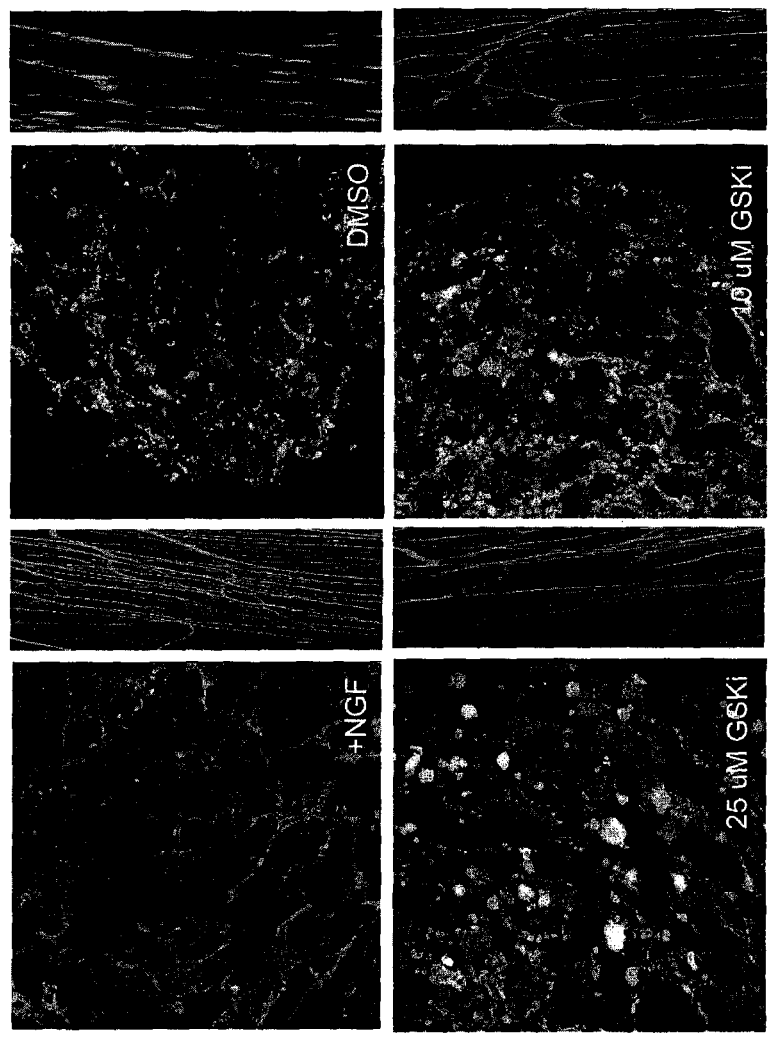
FIG. 26 shows that, after global NGF withdrawal, 10 µM or 25 µM GSK inhibitor blocks axon degeneration, but does not block cell death.

Inhibiting GSK in an axon degeneration paradigm where signaling through the cell body does not occur was also studied. Fifty µM SB415 slightly delayed degeneration after lesion, so inhibiting GSK3 has a direct effect on the axon, most likely through stabilization of the axonal microtubule network. This effect likely contributes to the delay in axon degeneration observed after global NGF withdrawal, but the role of GSK3b in the cell body appears to be more significant (FIG. 25). Additionally, protection of axons after global NGF withdrawal appears to be independent of the role of GSK in neuronal death since the GSK inhibitor blocked axon degeneration but did not block cell death (FIG. 26).

Example 6

Protection Against Peripheral Neuropathy in Patients

Tarceva® (erlotinib) is an EGFR kinase inhibitor. Treatment of patients with paclitaxel and other chemotherapeutic agents is known to lead to peripheral neuropathy (reviewed in Wilkes, *Semin. Oncol. Nurs.* 23(3):162-173, 2007). Patients treated with a combination of Tarceva® and paclitaxel showed significantly less peripheral neuropathy (p=0.012; Fisher's exact), as compared to a placebo+paclitaxel group (16.3% vs. 26.4% of patients; first 400 patients enrolled; analysis of common adverse events).

Example 7

Analysis of EGFR Kinase Levels in an Amyotrophic Lateral Sclerosis (ALS) Model

Amyotrophic lateral sclerosis ("ALS") is a severely debilitating and fatal neurodegenerative disease, the pathology of which is characterized by loss of motor neurons. Similar pathology occurs in mouse models of ALS containing mutations in the Superoxide Dismutase ("SOD") gene (SOD (G93A)). Phosphorylation of the EGF receptor is associated with axonal degeneration. EGFR levels are altered in SOD (G93A) mice, and an experiment was performed to determine whether phosphorylated EGFR levels are also altered in SOD (G93A) mice.

Spinal cords from terminal SOD(G93A) and non-transgenic littermates were cryosectioned (20 µm thick) onto slides and stored at −80° C. Slides were thawed to blocked in hydrogen peroxide (0.3% in PBS) for 5 minutes, and then were rinsed twice in PBS for 5 minutes per rinse. Slides were washed twice in PBS-T (PBS containing 0.1% Triton X100) for 10 minutes per wash. Slides were blocked in PBS containing 5% BSA and 0.3% Triton X100 for about 1 hour at room temperature. A rabbit monoclonal anti-phosphorylated EGFR primary antibody (Novus Biologicals) was diluted 1:500 in 1% BSA and 0.3% Triton X100 in PBS and incubated with the slides overnight at 4° C. The slides were washed four times in PBS-T for 10 minutes per wash. A biotinylated goat anti-rabbit secondary antibody (Vector Labs) was diluted 1:300 in 1% BSA and 0.3% Triton X100 in PBS and incubated with the slides for 30 minutes-1 hour. The slides were washed four times in PBS-T for 5 minutes per wash. Washed slides were incubated in Avidin-biotin complex solution (Vector Laboratories) for 30 minutes at room temperature. The slides were washed four times in PBS-T for 5 minutes per wash. The slides were then incubated with a peroxidase substrate (Diaminobenzidinc (DAB); Sigma) until the desired intensity developed. The slides were rinsed in water, coverslipped, and viewed.

Figure 27:
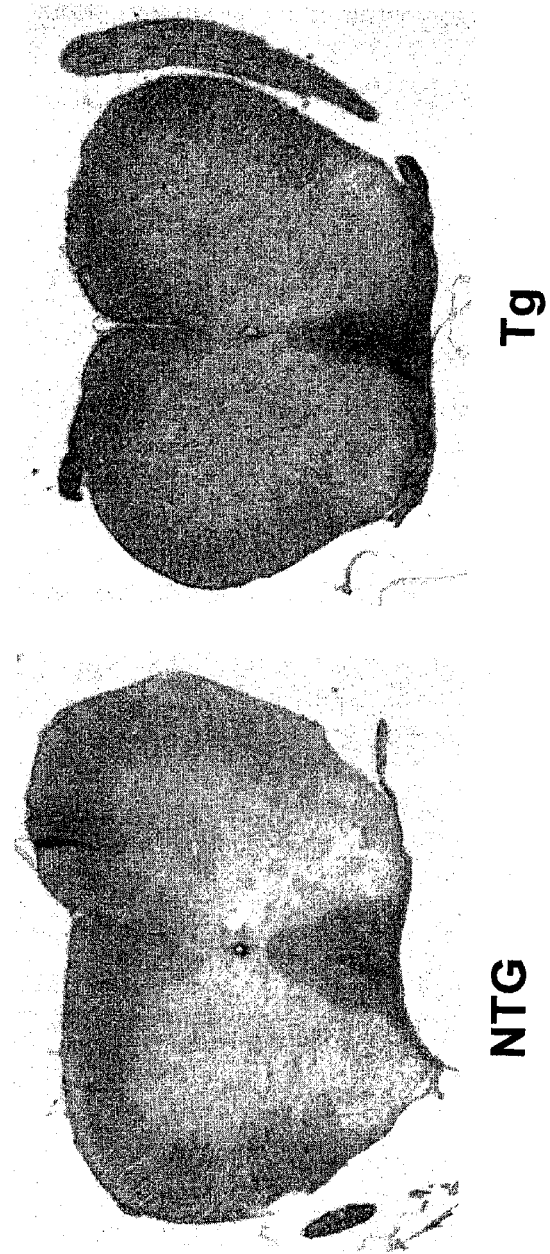
FIG. 27 shows that EGFR expression is increased in a section of SOD1 mouse (Tg) spinal cord stained with anti-EGFR antibodies (right panel), as compared to a non-transgenic control (NTG; left panel).
Figure 28:
FIG. 28 shows that EGFR is normally expressed in neurons (motor neurons) and that the level of phosphorylated EGFR (pEGFR) is increased in ALS SOD1 mouse model (SOD1-Tg) compared to a non-transgenic control (Non-Tg).

As shown in FIGS. 27 and 28, which show sections of spinal cord stained with EGFR antibodies, phosphorylated EGFR levels were increased in the SOD mice, as compared to the control mice. This observation shows that EGFR kinase inhibition may be beneficial in the treatment of ALS in vivo.

Immunohistochemical studies of SOD1 samples were also carried out. Slides were warmed to room temperature, outlined with an ImmEdge pen, hydrated by 2×10 minute washes in PBS at room temperature, and washed for 2×10 minutes in PBSTx at room temperature. Antibody blocking was carried out for 1-2 hours at room temperature (5% BSA, 0.3% Tx in PBS; (25 mg BSA in 500 ml PBS+1.5 ml 10% Tx)). Samples were incubated with primary antibodies overnight at 4° C. in 1% BSA, 0.3% Tx in PBS (NF (mouse, Millipore) 1:200; SM132 (mouse, Covance) 1:300)). Samples were washed after primary antibody incubation 4×10 minutes in PBSTx (0.1%) at room temperature. Secondary antibodies were applied (Molecular Probes, Alexa conjugated; Donkey anti-Mouse Alexa-488; diluted 1:500 in 1% BSA, 0.3% Tx in PBS) and samples were incubated for 2 hours at room temperature. Samples were washed after secondary antibody incubation 2×10 minutes in PBSTx, and 2×10 minutes PBS. Optionally, nuclear counterstaining was carried out during the second wash by application of DAPI at 1:10,000 in PBS. Mounting was carried out with Vectashield mounting medium (Vector Labs).

Figure 29:
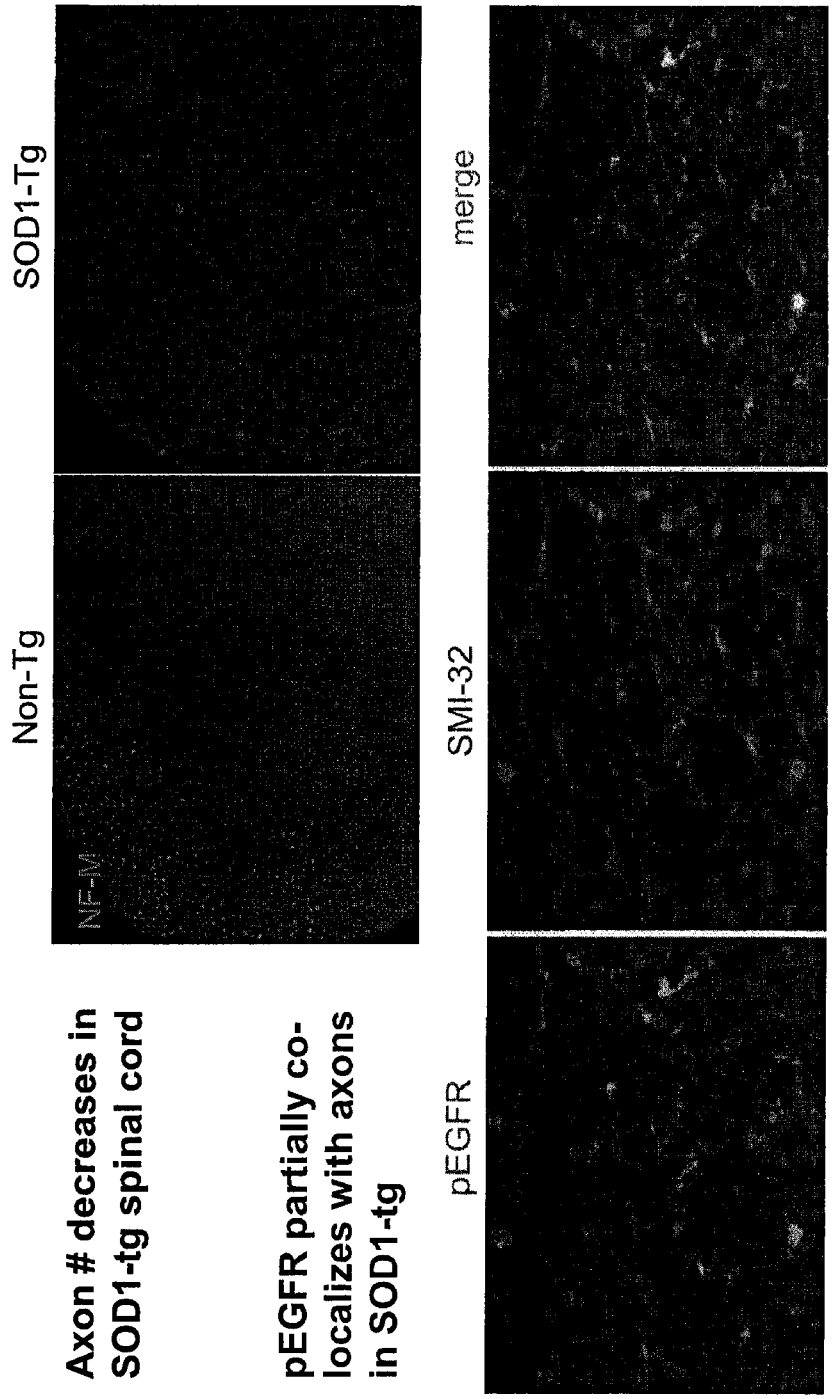
FIG. 29 shows that the number of axons is decreased in the ALS SOD 1 mouse model (SOD1-Tg) as compared to a non-transgenic control (Non-Tg), and that the phosphorylated EGFR (pEGFR) in the ALS SOD1 model partially co-localizes with axons.

FIG. 29 shows pEGFR remaining in axons in the SOD ALS model. As shown in the figure, axon number decreases in SOD1-tg spinal cord, and pEGFR partially co-localizes with axons in SOD1-tg animals. Thus, axons are lost in SOD1 transgenic mice as compared to non-transgenic controls, and many of the remaining exons are immunoreactive for pEGFR.

Example 8

Protection of Cerebellar Granule Neurons from Serum Deprivation/KCl Reduction-Induced Degeneration Kinase inhibitors (inhibitors of GSK3, JNK, EGFR, p38, and CaMKK) were tested for their capacity to protect cultured cerebellar granule neurons (CGNs) following serum deprivation/KCl reduction. Briefly, CGNs isolated from P7 mouse brain were cultured on PDL- and laminin-coated 96-well tissue culture dishes in medium containing serum and potassium (Basal Medium Eagles including 29 mM KCl and 10% FBS) at 37° C. After 24 hours in culture, cells were switched to "deprivation" medium (Basal Medium Eagles including 5 mM KCl), alone or in combination with various small molecule inhibitors as shown in Table 8. After a further 24 hours in culture, the neurons were fixed with 4% paraformaldehyde and stained with a neuronal marker (anti-class III f3-Tubulin, Covance). Image acquisition was performed using the ImageXpress automated imaging system (Molecular Devices). The plate set-up used is summarized in Table 8.

TABLE 8

| | 1-3 | 4-6 | 7-9 | 10-12 |
|---|---|---|---|---|
| A | Positive Control (29KCl + serum) | 5 mM KCl + 1 µM EGFR kinase inhibitor | Positive Control (29 mM KCl + serum) | 5 mM KCl + 1 µM EGFR kinase inhibitor |
| B | Negative Control (5 mM KCl) | 5 mM KCl + 10 µM EGFR kinase inhibitor | Negative Control (5 mM KCl) | 5 mM KCl + 10 µM EGFR kinase inhibitor |
| C | 5 mM KCl + 5 µM JNK inhibitor | 5 mM KCl + 30 µM EGFR kinase inhibitor | 5 mM KCl + 5 µM JNK inhibitor | 5 mM KCl + 30 µM EGFR inhibitor |
| D | 5 mM KCl + 10 µM JNK inhibitor | 5 mM KCl + 5 µM p38 inhibitor | 5 mM KCl + 10 µM JNK inhibitor | 5 mM KCl + 5 µM p38 inhibitor |
| E | 5 mM KCl + 20 µM JNK inhibitor | 5 mM KCl + 10 µM p38 inhibitor | 5 mM KCl + 20 µM JNK inhibitor | 5 mM KCl + 10 µM p38 inhibitor |
| F | 5 mM KCl + 5 µM CAMKK inhibitor | 5 mM KCl + 30 µM p38 inhibitor | 5 mM KCl + 5 µM CAMKK inhibitor | 5 mM KCl + 30 µM p38 inhibitor |
| G | 5 mM KCl + 15 µM CAMKK inhibitor | 5 mM KCl + 10 µM GSK3 inhibitor | 5 mM KCl + 15 µM CAMKK inhibitor | 5 mM KCl + 10 µM GSK3 inhibitor |
| H | 5 mM KCl + 30 µM CAMKK inhibitor | 5 mM KCl + 30 µM GSK3 inhibitor | 5 mM KCl + 30 µM CAMKK inhibitor | 5 mM KCl + 30 µM GSK3 inhibitor |

Figure 30:
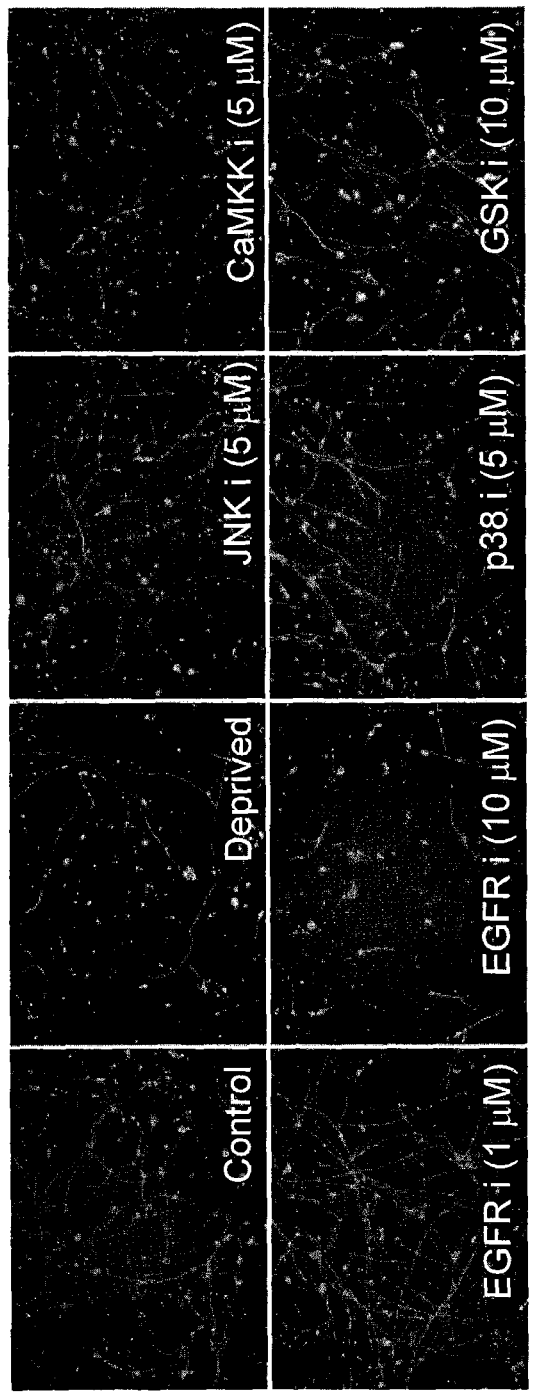
FIG. 30 shows that the small molecule inhibitors of JNK (5 µM SP600125), CaMKK (5 µM STO-609), EGFR (1 µM or 10 µM AG555), p38 (5 µM SB239063), and GSK (10 µM SB415286) protect cerebellar granule neurons from serum deprivation/KCl reduction.

JNK inhibitor = SP600125
CAMKK inhibitor = STO-609
EGFR inhibitor = AG 555
P38 inhibitor = SB 239063
GSK3 inhibitor = SB 415286
Columns 1-6: cell density = $5 \times 10^4$/well
Columns 7-12: cell density = $2.5 \times 10^4$/well As shown in FIG. 30, the kinase inhibitors were found to be effective at protecting the CGNs from degeneration, similar to the findings in Examples 2 and 3 for DRGs.

Example 9

Protection of Hippocampal Neurons from Rotenone-Induced Degeneration

Kinase inhibitors (inhibitors of GSK3, JNK, EGFR, p38, and CaMKK) were tested for their capacity to protect hippocampal neurons from rotenone-dependent degeneration. The assay was performed as follows. First, hippocampal neurons were dissected. Briefly, E18-E19 embryos were removed from anesthetized pregnant rats, placed in Petri dishes containing cold HBSS (see above), and washed in fresh, cold HBSS. Embryos were removed from their sacs and placed in fresh, cold HBSS, and the brains were isolated and placed in fresh, cold HBSS using standard techniques. The hippocampus and cortex were isolated from each embryo, and the brains were cut sagitally in half to separate the hemispheres. Remaining cerebellum/brain stem, olfactory bulbs, non-cortex ventral underlying tissue, and the meninges were removed. The hippocampi were removed from the remaining tissue and transferred to a 1.5 ml tube on ice. The cortical tissues were removed to a separate 1.5 ml tube on ice. As much HBSS as possible was removed, and 1% Trypsin (Hyclone)/0.1% DNase (Sigma) in HBSS was added to the remaining tissue in each tube. The tissues were each broken up using a fire-polished pipette. The tissues were incubated for ten minutes at 37° C., with tapping of the tubes every two minutes. As much solution as possible was removed from the tissues, and the tissues were each washed with 0.05% DNase (Sigma) solution. The samples were triturated in 0.05% DNase (Sigma) about 20× with each of the following (1) fire polished pipette at ⅔ bore, and (2) fire polished pipette at ⅓ bore. The samples were permitted to settle for five minutes, after which the supernatants were collected (the debris settled and the supernatant was removed with a pipette) and the cells were counted on a hemocytometer.

Nucleofection was performed on the isolated hippocampal neurons. Briefly, the desired number of cells ($0.5-1\times10^6$ cells per nucleofection) were isolated by centrifugation. As much of the supernatant solution as possible was removed and the pelleted cells from each tube were re-suspended in 20 µl room temperature nucleofection solution (Amaxa). Each resuspension was added to pre-aliquoted β-actin—GFP "pCAGGS-AFP" DNA (400 ng per run) and tapped gently. The mixtures were transferred to nucleocuvette wells of a 96 well shuttle plate, and the plate was inserted into the nucleofector device. Neurons were nucleofected using a preset Amaxa program, CU 110. Immediately following nucleofection, 100 µl pre-warmed CNBM (10 ml B27 (serum-free supplement; Invitrogen), 5 mis 100× Pen-Strep, 5 mis 100× Glutamax, 480 mis NBM (neurobasal medium; Invitrogen)) was added, and the cells were subsequently plated at a density of 70,000 cells/well in 8-well PDL-coated chamber slides. Neurons were grown for 5-14 days before rotenone addition, with changes of medium every 3-5 days.

Ten µM rotenone (resuspended in DMSO; VWR) was added to neurons in the presence or absence of vehicle or experimental compounds. 17-18 hours after rotenone addition, neurons were fixed in a solution of 4% paraformaldehyde/15% sucrose for 40 minutes at room temperature. Neurons were washed once with PBS and mouse anti-Tuj1 antibody (Covance) was added at a dilution of 1:1000 (in PBS, 0.1% Triton X-100, 2% goat serum) for an overnight incubation at 4° C. Neurons were washed 4× with PBS and goat anti-mouse antibody conjugated to Alexa-568 (Alexa) was added at a dilution of 1:200 (in PBS, 2% goat serum) for 30 minutes. Neurons were again washed 4× with PBS and mounted on slides in Vectashield mounting medium (Vector Labs). All neurons were visualized with Tuj1, and individual neurons were visualized with GFP.

Figure 31:
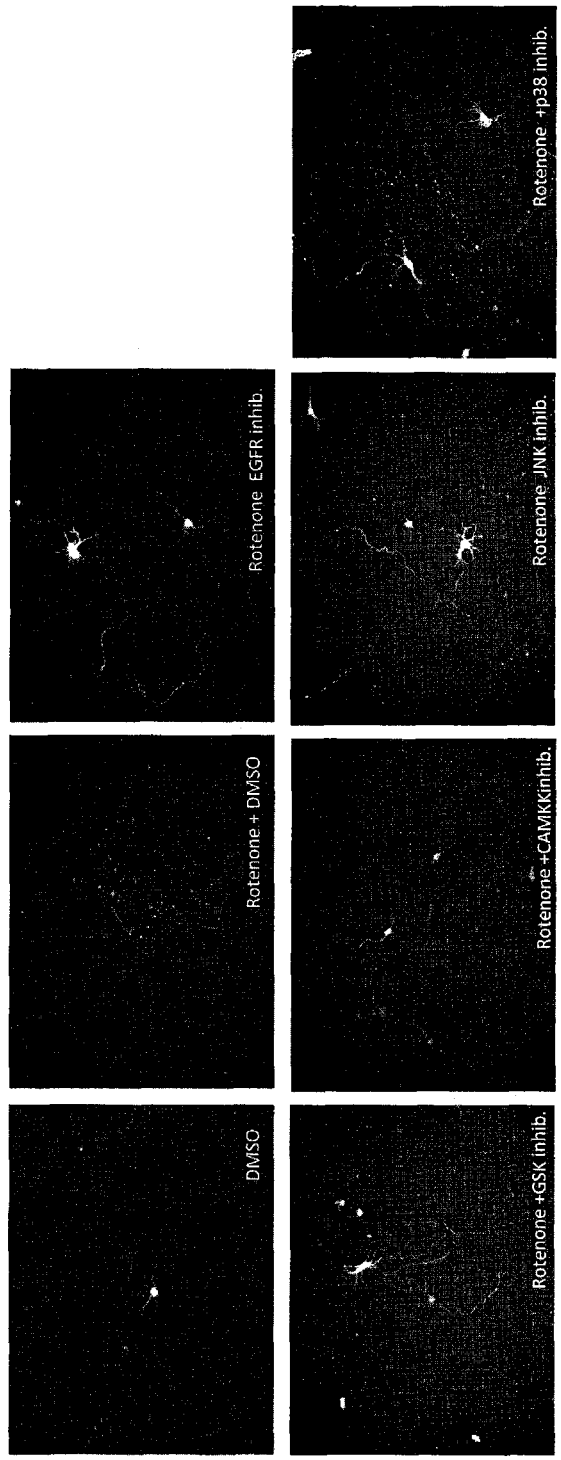
FIG. 31 shows that the small molecule inhibitors of EGFR, GSK, CaMKK, JNK, and p38 protect hippocampal neurons against 10 µM rotenone.
Figure 32:
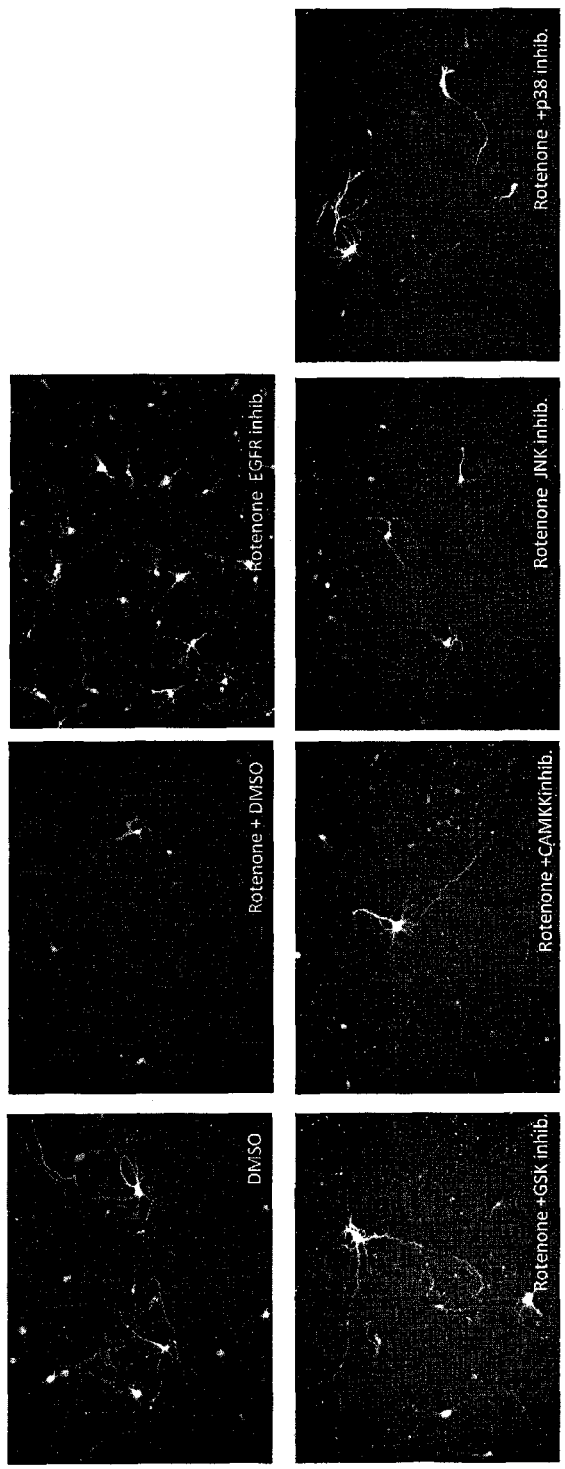
FIG. 32 shows that the small molecule inhibitors of EGFR, GSK, CaMKK, JNK, and p38 protect cortical neurons against 10 µM rotenone.

As shown in FIG. 31, the kinase inhibitors were found to protect hippocampal neurons from rotenone-dependent degeneration. Similar studies were carried out with cortical neurons, and showed that cortical neurons are also protected from rotenone-dependent degeneration by kinase inhibitors (FIG. 32).

Example 10

Visualization of ErbB Receptor on Axons

Figure 33:
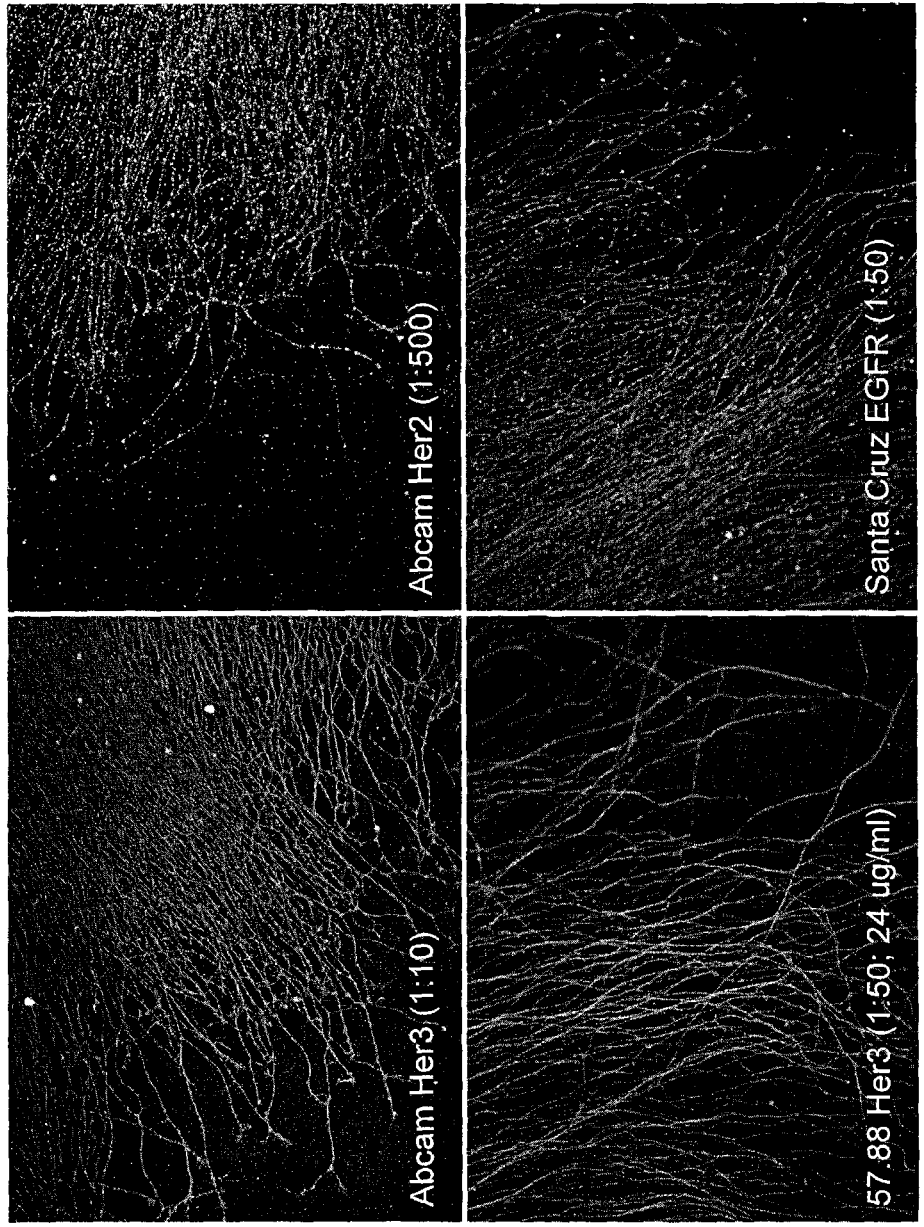
FIG. 33 shows that ErbB receptors are detected on axons in dorsal root ganglion neurons by immunocytochemistry using antibodies specific for EGFR (top left panel), Her2 (top right panel), Her3 (bottom left panel), and Her4 (bottom right panel).

To visualize ErbB receptor expression on axons, DRGs were cultured as described above for the screen. After 24 hours of growth, cells were fixed by adding 8% PFA/30% sucrose to culture medium at a 1:1 ratio for 30 minutes and washed 1× with PBS. Fixed cells were incubated in 5% BSA and 0.2% TritonX100 in PBS for 30 minutes, and then incubated overnight in 2% BSA in PBS at 4° C. with the following antibodies: (1) 50 µg/ml anti-EGFR (D1-5, Genentech), (2) 1:500 anti-ErbB2 (Abeam), (3) 24 µg/ml anti-ErbB3 (57.88, Genentech), and (4) 1:500 ErbB4 (Abeam). Cells were washed 1× with PBS, followed by incubation with a fluorescently conjugated secondary antibody (1:200, Invitrogen) at room temperature for 30 minutes, washed 1× with PBS containing Hoechst 33258 (1 µg/ml, Invitrogen), followed by a final PBS wash, and coverslipped with 250 µl of Fluoromount G (Electron Microscopy Sciences). As shown in FIG. 33, ErbBs are detected on axons by immunocytochemistry.

Example 11

Characterization of EGFR Expressed on Axons by Use of EGFR Ligands

Experiments were carried out to assess the effects of activation of EGFR by ligands, including EGF.

Materials and Methods

Dorsal Root Ganglia (DRG) immunoblots were prepared as follows. Primary cells used in the experiments were Charles River CD-1 E13 Dorsal Root Ganglia (DRG). The cells were maintained in N3/F12 (+25 ng/ml NGF) medium (Ham's F12 (23 ml), N3 supplement (1 ml), glucose (1 ml of 1 M glucose stock), 25 ng/ml Nerve Growth Factor 2.5 S, mouse (Roche 11362348001) in Ham's F12 (stock: 50 µg/ml-80° C.), which was filter-sterilized prior to use). The experiments also employed Triton lysis buffer (20 mM Tris pH 7.5, 150 mM NaCl, 0.1% Triton-X100, 100× Phosphatase inhibitor cocktail I (added fresh), 100× Phosphatase inhibitor cocktail II (added fresh), 1 tablet/10 ml Protease inhibitor tablet (added fresh)).

DRG explants were prepared on Day 0. Embryo dissections were carried out in L15 medium (dissection tools were soaked in 70% isopropanol, and dishes were set up on ice: 10 cm dishes (4 embryos per dish) and one 6 cm dish for spinal cords). E13.5 spinal cords were extracted into DMEM+10% FBS. 5×20 DRGs were detached from the spinal cord. 8 well slides were filled with 250 µl N3/F12 (25 ng/ml NGF)+7 µM cytosine arabinoside. Approximately 20 DRGs were placed in each well (five total), and attachment was allowed for about 10 minutes at room temperature. On day 2, media was changed to N3/F12±25 ng/ml NGF. On day 3, ErbB ligands were added (1000×; 100 µg/ml; dilute in SQ water 1:10) for 30 minutes to 1 hour (SQ water (control); EGF (ErbB1); Neuregulin-1 (ErbB3); Beta-cellulin (ErbB1/4); Epiregulin (ErbB1/4); Anti-NGF (25 µg/ml)) and slides were shaken slightly.

Immunobloting was carried out by aspiration of media with a pipette tip, washing twice with ice-cold sterile PBS, and removal of all PBS using an aspirator with a pipette tip or kimwipes. Cells were lysed with 40 µl Triton lysis buffer on ice. Lysate was collected, rotated for 30 minutes at 4° C., spun for 5 minutes at top speed, and supernatant was kept (stop: −80° C.). About 20 µl of sample was loaded. The sample was prepared by adding 1×SDS sample buffer and NuPAGE reducing agent (10×), and the lysate was boiled. Samples were fractionated by 10% SDS-PAGE (at 120 Volts) (run for two membranes) with standards (1 µl MWM; 1 µl and 2 µl spinal cord lysate). The gels were blotted using the iBlot program 3 (Nitrocellulose), and the blot was cut at 98 kDa. The top membrane was blocked in 5% BSA in TBST for 1 hour. Primary antibody was placed into 2 ml 5% BSA in TBST for 1 hour (Calbiochem anti-P-tyrosine HRP conjugate (PY20) 1:10,000). The blot was washed with TBST for 3×5 minutes and developed with ECL. The bottom membrane was blocked in 5% milk for one hour in PBS. Primary antibodies were placed in 2 ml 5% BSA in TBST 4° C. for two days in vacuum bag. The antibodies used were CS anti-P-membrane), and SC anti-Erk1 rabbit (42/44 kDa) 1:1000 (on a separate membrane). The blot was washed in TBST for 3×5 minutes. Secondary antibody was added into 10 ml 5% milk in TBST 1:5000 and incubated for 1 hour at room temperature (Red (680) anti-rabbit). The blots were washed with TBST for 3×5 minutes, and scanned in PBS with Odyssey. Quantification was carried out by choosing a background method and standard bands that minimize negative/counter-intuitive values: i.e., top/bottom, right/left, user-defined (user-defined). The lower the intensity of the concentration standard, the fewer negative values.

Results

Figure 34:
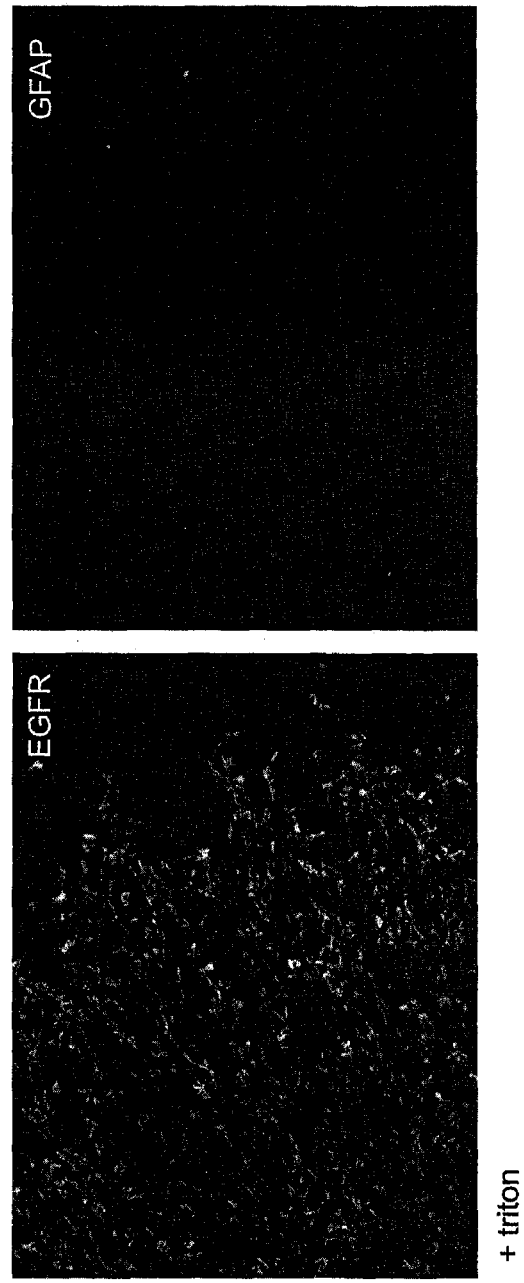
FIG. 34 shows that EGFR is expressed in axons of dorsal root ganglion neurons using immunocytochemistry.
Figure 35:
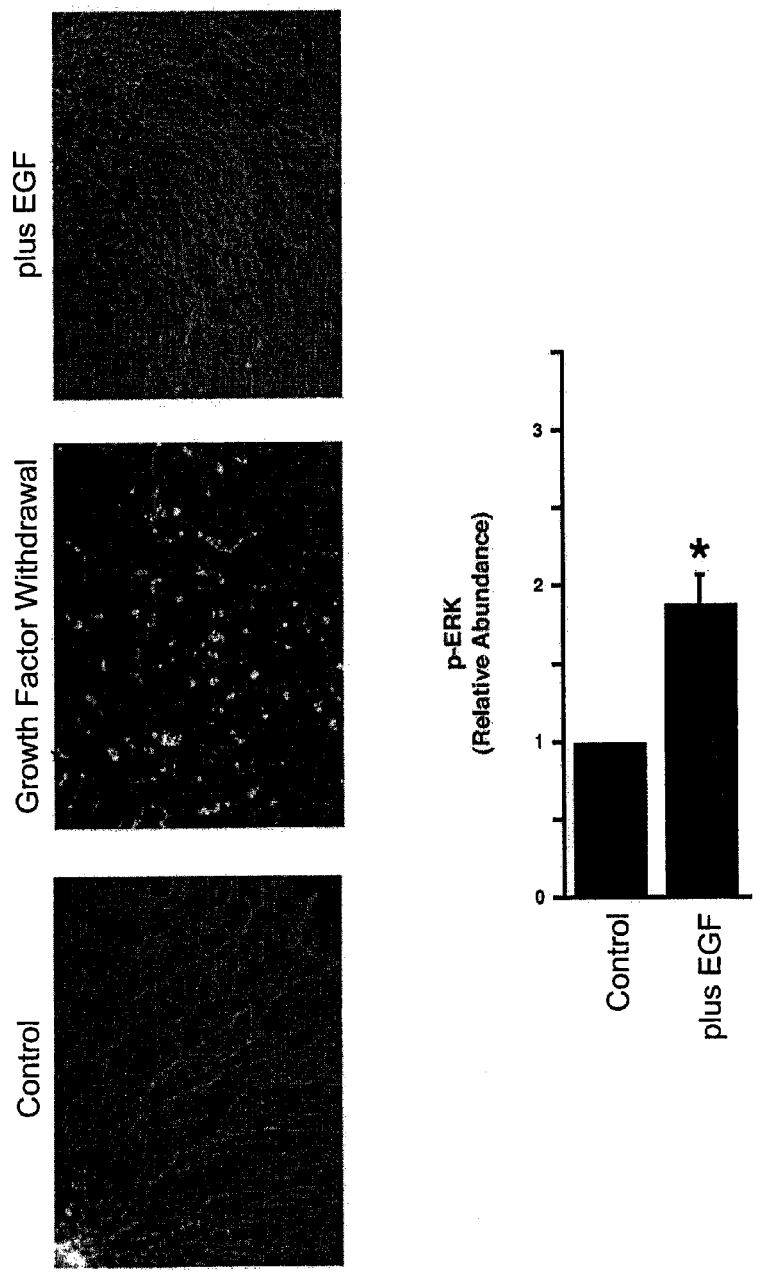
FIG. 35 shows that 100 µg/mL EGF does not induce axon degeneration when added to dorsal root ganglion neurons and that addition of 100 µg/mL EGF induces phosphorylation of ERK in the treated neurons.
Figure 36:
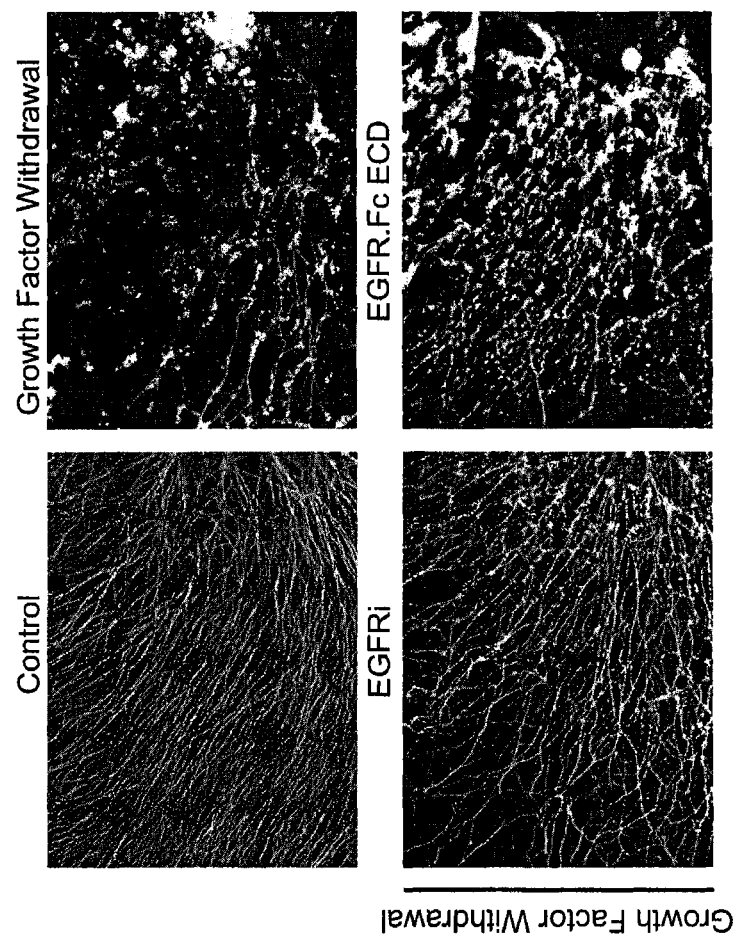
FIG. 36 shows that the EGFR ectodomain (50 µg/mL) does not block axon degeneration induced by NGF withdrawal in dorsal root ganglion neurons.

The goal of these experiments was to see if activation of EGFR by EGF would be sufficient to drive degeneration. As shown in FIG. 34, EGFR is expressed on axons. FIG. 35 shows that EGF added to neurons maintained in NGF does not cause degeneration. To ensure that EGF is capable of activating EGFR/ErbBs in the neuronal cultures used in these assays, ERK activation was assessed (ERK is a downstream target of EGFR). As shown in the graph in FIG. 35, adding EGF increased ERK activity, as determined by Western blot. These data show that activating EGFR is not sufficient to drive degeneration.

Example 12

Characterization of EGFR Expressed on Axons by Use of EGFR Ectodomains

Experiments were carried out to assess the effects of EGFR ectodomains on activation of EGFR.

Materials and Methods

Materials used in these studies include BD Biocoat PDL/Laminin coated glass 8 well chamber slides (BD 354688); L15 medium (Invitrogen 11415114); albumin from bovine serum (BSA) (Sigma A7906-500 g); fetal bovine serum (Sigma F2442-100 ml); N3 supplement (see above); Fluoromount G (Electron Microscopy Sciences 17984-25); 24×60 mm No. 1 coverslips (VWR 48393 106); monoclonal anti-neuronal class III beta-tubulin (Covance MMS-435P); Nerve Growth Factor 2.5 S, mouse (Roche 11362348001) in Ham's F12; and Triton X-100 (Sigma T8787-100 ml). Solutions used in these experiments include 25 ml N3/F12 medium (23 ml of Ham's Sucrose/8% PFA (see above).

Ectodomains (R&D Systems) were resuspended in sterile filtered 0.1% BSA in PBS to 1 mg/ml. Mouse E13.5 embryos were dissected out and place into L15 medium. Using forceps, the ventral region of the embryo was opened, organs removed, ribs cut away, and spinal cord dissected out with DRGs attached. The spinal cords with DRGs attached were placed into L15 medium+5% goat serum on ice. DRGs were removed with a tungsten needle and the remaining spinal cord was disposed of 8 well slides were filled with N3-F12 plus 25 ng/ml NGF. DRGs were sectioned into halves. Sectioned DRGs were placed in the centers of each well of an 8-chamber slide and DRGs were allowed to attach at room temperature for 5-10 minutes. Ectodomain was added to a final concentration of 50 µg/ml in the top row. Slides were placed in a 37° C. incubator overnight. Ectodomain was added to the bottom row to a final concentration of 50 µg/ml. Anti-NGF antibody was added to the wells at a concentration of 25 µg/ml. EGFR inhibitor AG555 was added at a concentration of 10 µM as a positive control.

After 24 hours of anti-NGF antibody treatment, 8% PFA/30% sucrose was added directly to the culture medium at a 1:1 dilution for 30 minutes. The Teflon divider was removed after the first 15 minutes, and slides were washed once with PBS.

Slides were blocked in 5% BSA/0.2% Triton for 30 minutes, and incubated with primary antibodies (Tuj1 (1:1,000)) overnight in 2% BSA. Slides were washed with PBS once and secondary antibody (Goat anti-mouse 488; 1:200) was added. Slides were incubated for 1 hour at room temperature, washed 2× with PBS, coverslipped with 250 µl of fluoromount G, and stored at 4° C.

Results

In addition to EGF, there are many ligands that can activate EGFR. To test whether EGFR activation during degeneration is ligand dependent, EGFR ectodomain from R&D Systems was added at a concentration of 50 µg/ml, which should be sufficient to bind any free ligands that may activate EGFR. The EGFR ectodomain, added either 24 hours prior to, or at the same time as adding anti-NGF, does not block independent.

Example 13

Figure 37:
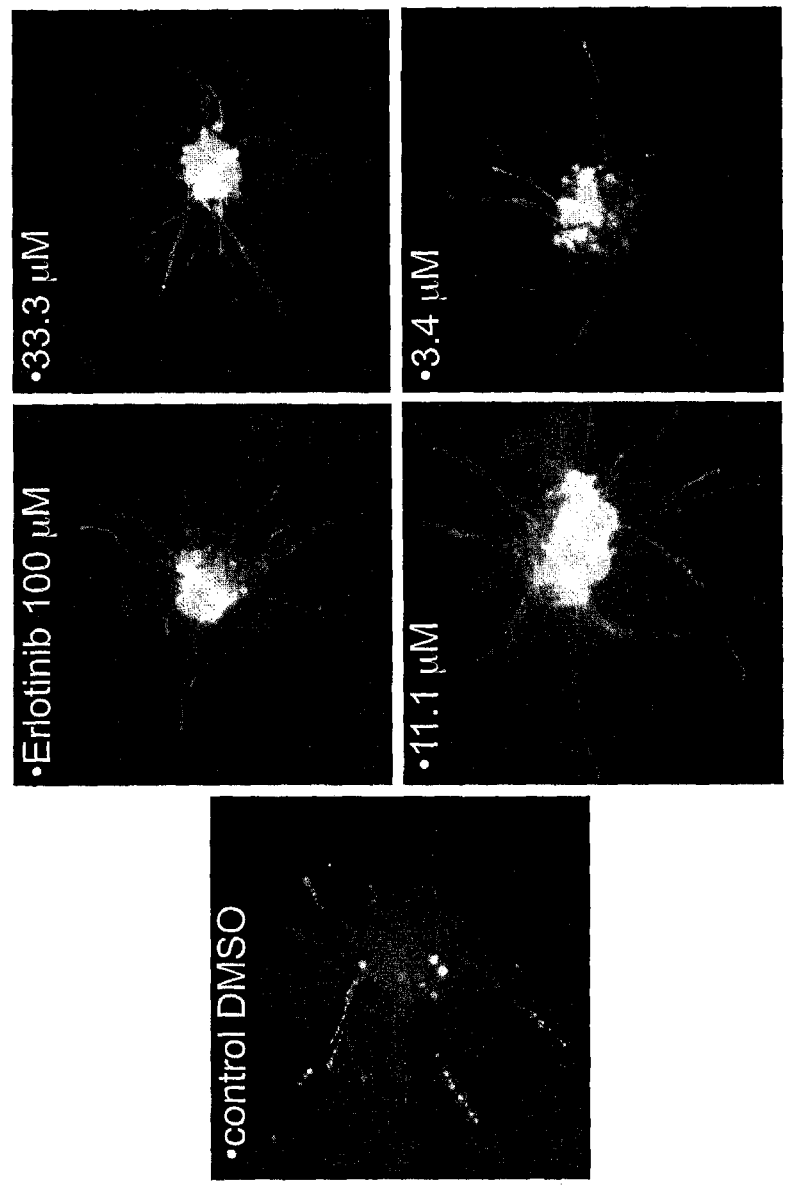
FIG. 37 shows that 3.4 µM, 11.1 µM, 33.3 µM, and 100 µM Tarceva® (erlotinib) blocks degeneration in dorsal spinal cord explants.

The dorsal spinal cord (DSC) explant is another model of neurodegeneration. DSCs grow out axons over a period of days, but if they are not rescued with the addition of a survival factor, they will eventually degenerate. As shown in FIG. 37, Tarceva® (Erlotinib) can delay this degeneration program.

Example 14

A. Inhibition of Dual Leucine Zipper-bearing Kinase

Materials and Methods

DLK Transfection in 293 Cell Line 293 cells were plated at 30% confluence into 3 wells of a 6-well plate. Cells were transfected with either control plasmid DNA, a DNA construct expressing wild type DLK, or two plasmids, with one expressing wild type DLK and the other expressing a DLK in which threonine 277 has been mutated to alanine (T278A), creating a form of the protein without activity (Fugene 6, Roche). Twenty-four hours after transfection, cells were washed with PBS, scraped off each plate, and transferred to an eppendorf tube. Cells were then spun down and excess media was removed. Pelleted cells were lysed in 20 mM Tris, 150 mM NaCl, 0.1% Triton X-100, and placed at 4° C. for 30 minutes. Samples were then spun to remove insoluble particles and tested for protein concentration in a bicinchoninic acid (BCA) assay (Promega).

Samples were run on a 10% polyacrylamide gel (Invitrogen) and transferred using an iBlot device (Invitrogen) according to the manufacturer's specifications. Blots were blocked for 1 hour in TBST (Tris-buffered saline+1% Tween 20) with 5% bovine serum albumin (BSA). After blocking, blots were incubated overnight in primary antibodies directed against JNK (Cell Signaling Technologies) or the phosphorylated form of JNK (Cell Signaling Technologies) in TBST+1% BSA. After incubation, blots were washed 3 times in TBST and then incubated with HRP-conjugated anti-rabbit secondary antibodies for 1 hour at room temperature. Blots were once again washed three times and then incubated with ECL (Promega) for 1 minute. Blots were then exposed on film and analyzed.

Degeneration in DRGs after DLK siRNA

Mouse E13.5 embryos were dissected and placed into L15 medium (Invitrogen). The spinal cord was dissected out from the embryos with DRGs attached. The spinal cords with DRGs attached were placed into L15 medium+5% goat serum (Gibco) on ice. The DRGs were removed using a tungsten needle and the remaining spinal cord was disposed. Eight-well slides were filled with N3-F12 solution (23 ml of Ham's F12, 1 ml of N3 supplement, and 1 ml of 1 M glucose) to which was added 25 ng/ml NGF (Roche). (N3 supplement was made by dilution of N3 100× concentrate, which was made by mixing the following ingredients, in the following order: 5.0 ml Hank's buffered saline solution (HBSS; Ca, Mg free; Invitrogen), 1.0 ml bovine serum albumin (10 mg/ml in HBSS=150 µm), 2.0 ml Transferrin (T1147-1G, human, 100 mg/ml in HBSS=1.1 mM), 1.0 ml sodium selenite (S9133-1MG, 0.01 mg/ml in HBSS=58 µM), 0.4 ml putrescine dihydrochloride (P5780-5G, 80 mg/ml in HBSS=500 mM), 0.2 ml progesterone (P8783-5G, 0.125 mg/ml in absolute ethanol=400 µM), 0.02 ml corticosterone (C2505-500MG, 2 mg/ml in absolute ethanol=5.8 mM), 0.1 ml triiodothyonine, sodium salt (T6397-100MG, 0.2 mg/ml in 0.01 N NaOH=300 µM), 0.4 ml insulin (16634-250MG, bovine pancreas, 241 U/mg, 25 mg/ml in 20 mM HCl=4.4 mM), for a total volume of 10.02 ml (can be stored at −20° C.)). An N3 supplement stock was made by combining the following: 10 ml Pen/Strep (100×, Gibco), 10 ml glutamine (200 mM, Gibco), 10 ml MEM vitamins (100×, Gibco), 10 ml N3 concentrate (100×, see above), for a total volume of 40 ml. The mixture was filter sterilized using a 0.22 µm filter, and 1-2 ml aliquots were stored at −20° C.

Neurons were trypsinized using 0.05% trypsin-EDTA (Gibco) at 37° C. for 30 minutes, spun down and counted. Two hundred thousand cells were electroporated using an Amaxa 96-well nucleofector with 400 ng control of DLK siRNA (program DC 100), then split equally onto two wells of an 8-chamber slide (BD Biocoat PDL/Laminin coated glass, Becton Dickinson). Neurons were permitted to attach to the slide at room temperature for 5-10 minutes, followed by incubation for 3 days at 37° C. The anti-NGF antibodies were then added to the right half of the slide (4 wells) at a concentration of 25 µg/ml. After incubation for 20 hours at 37° C., the slides were fixed with 30% sucrose/8% paraformaldehyde (PFA) by adding 250 µl of the fix solution directly to the 250 µl of culture medium. (To make the 30% sucrose/8% PFA solution, the following ingredients were added to a 600 ml beaker including a stir bar: 250 ml 16% PFA (cat #15710-S, Electron Microscopy Sciences), 50 ml 10×PBS pH 7.4, and 150 g sucrose. The solution was mixed under low heat until dissolved. Then 6-8 drops of 1 M NaOH were added to bring the pH to 7.4. The volume was then brought to 500 ml with water in graduated cylinder. The solution was mixed well, placed in aliquots, and frozen).

The slides were fixed for 30 minutes, followed by washing three times with PBS. All cells were labeled with a neuron specific β-tubulin antibody (Tuj1 (1:1000) in 2% BSA, 0.1% Triton) at 4° C. overnight. The primary antibody was removed and the slides were washed three times with PBS. Slides were incubated with goat Alexa 488 anti-rabbit secondary antibody (1:500) for one hour followed by three washes in PBS, and then coverslipped with 130 µl of mounting medium (Fluoromount G; Electron Microscopy Sciences) and 24×60 mm No. 1 coverslips (VWR).

Quantitative PCR (qPCR) for DLK

E13.5 DRGs were dissected, electroporated with control siRNAs or siRNAs directed against DLK, and cultured as described above for a period of five days. RNA from neurons was then isolated using Purify Total RNA by Qiagen RNeasy Mini kit, according to the manufacturer's protocols. 10 ng of total RNA from cells treated with control and DLK siRNAs were run in triplicate in quantitative PCR experiments (Qiagen Quantifect SYBR Green RT-PCR) using DNA primers specific for DLK and GAPDH (control) (CATCATCTGGGTGTGGGAAG (forward primer) and AGTTGCAGCATGAGGGCATTC (reverse primer); SEQ ID NOs: 16 and 17). Amplification curves were analyzed and relative RNA concentrations of each sample were calculated relative to controls.

Results

Figure 38:
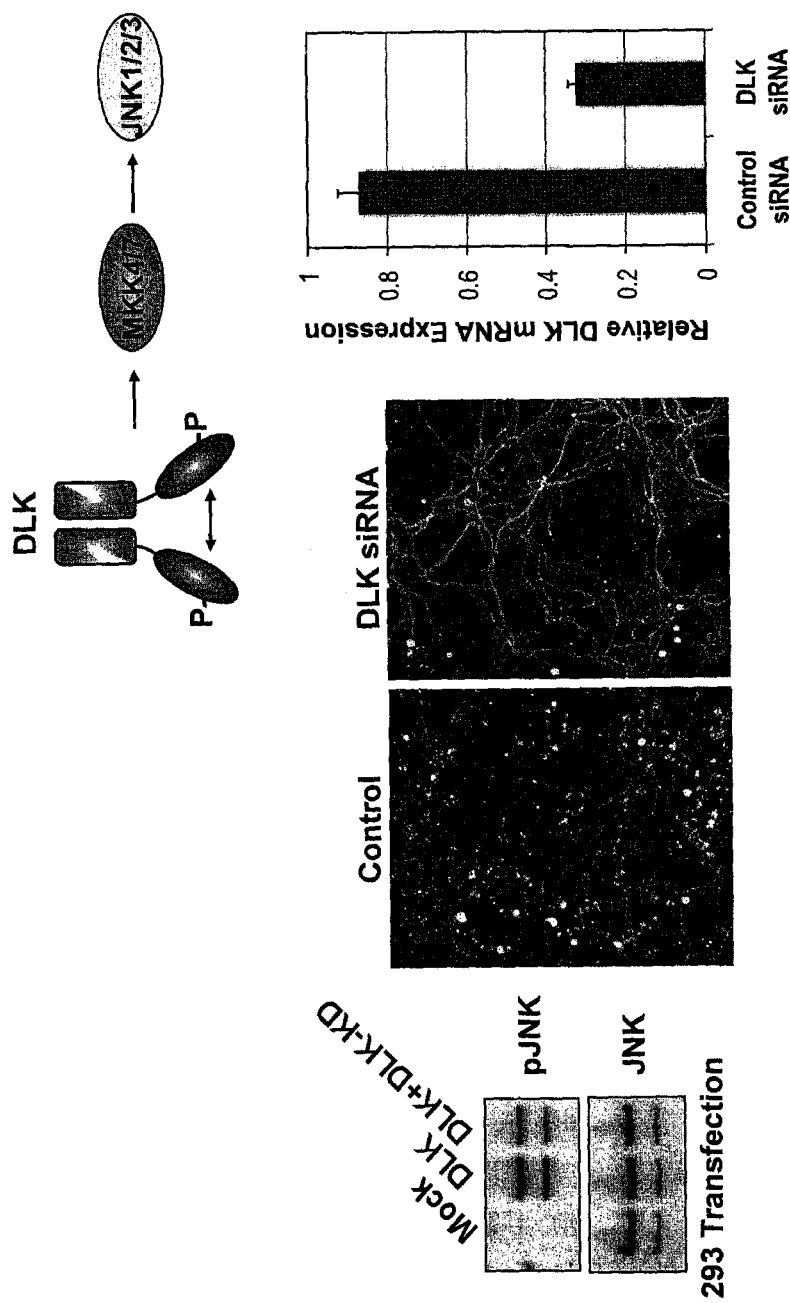
FIG. 38 shows that dual leucine zipper-bearing kinase (DLK) acts upstream from JNK in axon degeneration. Transfection of a plasmid encoding wild type DLK in 293 cells results in JNK activation (as measured by increased levels of phosphorylated JNK) compared to cells mock-transfected with a control plasmid or a plasmid encoding kinase-dead DLK (DLK-KD). Knockdown of DLK expression by siRNA in dorsal root ganglion neurons protects axons from degeneration induced by NGF withdrawal. The knockdown of DLK expression using DLK siRNA was confirmed using quantitative PCR as compared to a control siRNA (bottom right panel).

The results of these experiments are shown in FIG. 38. Transient transfection of 293 cells with a plasmid encoding wild type DLK resulted in the phosphorylation and activation of JNK, showing that DLK is a kinase upstream of JNK in a signaling cascade. Co-transfection of a plasmid encoding a kinase-dead DLK reduced the levels of JNK phosphorylation. Knockdown of DLK expression via siRNA resulted in protection of neurons against degeneration as did inhibition of the downstream kinase JNK. In experiments using cultured neurons transfected with siRNAs directed against DLK (Dharmicon), neurons transfected with control siRNAs (as visualized by actin staining) underwent significant degeneration upon NGF withdrawal as visualized by TuJI staining (FIGS. 38 and 39). In contrast, in neurons transfected with siRNAs targeted against DLK, axon integrity was maintained upon NGF withdrawal. Knockdown of DLK expression in these experiments was confirmed using quantitative PCR with primers specific to DLK.

B. DLK Knockdown Protects Against Toxin-Induced Neuronal Cell Death

Experiments were performed to assess whether the above-observed protective effect of DLK inhibition is more generally protective against axon degeneration/neuronal apoptosis caused by other insults, such as toxin exposure. Isolated neurons were exposed to vincristine, a mitotic inhibitor, in the presence or absence of siRNA specific for DLK.

Cortical neurons were isolated using the following procedure. Rat E18 cortices devoid of meninges were dissected into ice-cold neurobasal media (Invitrogen). Cortices were dissociated in a final concentration of 0.1% trypsin/PBS (Worthington) for 30 minutes at 37° C. A final concentration of 0.1% DNase (Roche) was added to the tube and tissue was incubated at room temperature for 1 minute. Tissue was washed once with warm neurobasal media and the tissue was allowed to settle in the tube before 1 mL of neurobasal media containing 2% B27 supplement (Invitrogen) was added. Tissue was dissociated by trituration with a P1000 pipet (Rainin). The cells were counted and, for some experiments, transfected with siRNAs using a Biosystem 96-well nucleofector (Amaxa).

Cells were plated in 6- or 8-well chambers or 96-well poly-D-lysine coated dishes (BD Biosciences) at plated cell densitites of $2\times10^6$ cells/well, $1.25-2\times10^5$ cells/well, or $1\times10^4$ cells/well, respectively, for siRNA experiments (densities that allow for some cell death normally associated with the electroporation process). Neurons were mixed with 20 μL of nucleofection solution (Amaxa) and 600 ng of siRNA (Qiagen or Dharmacon). Gene silencing was assayed 3-4 days after plating by quantitative reverse transcriptase polymerase chain reaction (qRT-PCR). Briefly, RNA was isolated from transfected neurons using an RNeasy mini kit (Qiagen). Each reaction containing 10 ng of RNA was run in triplicate using the Quantifect SYBR Green RT-PCR kit (Qiagen) with DLK-, JNK1-, JNK2-, or JNK3-specific primers. Primers for the housekeeping gene, GAPDH, were used as controls. (All primers were purchased from Qiagen.) Amplification curves were analyzed for relative RNA concentrations in each sample using ΔCT.

Cortical neurons plated for 3-4 days were treated with 300 nM vincristine, a microtubule destabilizer, for 6-72 hours. NGF withdrawal-induced apoptosis and degeneration were assayed between 4-36 hours after the final treatment. Apoptosis and degeneration were assayed using both the MTT assay and the lactate dehydrogenase assay. The MTT (3-(4, 5-dimethylthiazol-2-yl)-2,5-diphenyltetrazolium bromide) assay measures cell viability based on mitochondrial function. MTT was added to a total of one tenth of the culture volume to each well and incubated at 37° C. with 5% $CO_2$ for 90-120 minutes. The MTT-containing culture media was aspirated and the cells were resuspended in an equal volume of solubilization solution (10% triton X-100, 1 drop HCl, 50 mL isopropanol). Absorbance (570 and 690 nm) was read using a spectrophotometer. Lactate dehydrogenase (LDH) levels were assayed using a CytoTox non-radioactive LDH assay kit (Promega) to assess the amount of cell death in assays. Fifty μt of media from different treatment conditions were used according to the manufacturer's instructions. For both the MTT and the LDH assays, cell survival/cell death was normalized to positive controls.

The results are shown in Table 9. As previously observed in the above-described DLK knockdown, NGF withdrawal experiments, knockdown of DLK expression was also protective against vincristine-induced cortical neuron death in two different assay systems. This finding indicates that DLK knockdown may be generally protective against stress-induced neuronal cell death in a number of different neuron types.

TABLE 9

Effect of DLK Knockdown on Cortical Neuron Survival upon Vincristine Challenge as Measured by LDH Assay

| Condition | % cell death (normalized) |
|---|---|
| Control (no treatment) | 0 |
| 20 hour vincristine treatment | 100 |
| DLK siRNA (no treatment) | 0 |
| DLK siRNA (20 hour vincristine) | 11 |
| | % Viability (normalized) |
| Control (no treatment) | 100 |
| 12 hour vincristine treatment | 77 |
| DLK siRNA (12 hr vincristine) | 95 |

C. Effect of DLK Modulation in Sympathetic Neurons

The foregoing analyses demonstrate that DLK inhibition is protective against toxin-induced or growth factor starvation-induced axon degeneration/apoptosis in cortical neurons and dorsal root ganglion neurons. Further experiments were performed to assess the ability of DLK inhibition to protect sympathetic neurons from the apoptosis normally induced by these challenges.

Sympathetic cervical ganglia were dissected from postnatal day 1 Sprague-Dawley rats (Charles River Labs) and collected in a dish containing Ultraculture media (Lonza) with 5% fetal bovine serum (Invitrogen). Ganglia were washed twice with serum-free Ultraculture media, and a final concentration of 0.1% trypsin (Worthington) was added and incubated with the tissue at 37° C. for 30 minutes. One percent DNase (Roche) solution in PBS was added to the ganglia and incubated at room temperature for 1-2 minutes. Ganglia were washed with Ultraculture and allowed to settle to the bottom of the tube. All wash media were removed and 1 mL plating media containing Ultraculture, 5% rat serum, 1% penicillin-streptomycin, 1% glutamax, 7 μM cytosine arabinoside (Sigma), and 50 ng/mL nerve growth factor (2.5S, Cedarlane Laboratory) was added to the tube. Ganglia were dissociated by trituration using a pipet (Rainin). The cell slurry was filtered over a 0.45 μm cell strainer (Falcon) and cell number was counted. Sympathetic neurons were plated at a density of 5000-7500 cells/well (96-well dish), 200,000 cells/well (6-well plate), or 100,000 cells/well (8-well chamber slide) and grown for 4-5 days in 5% $CO_2$ at 37° C. Every other day neurons were fed with fresh plating media containing 5-10 ng/mL NGF.

NGF withdrawal assays were performed as described in Example 14A. Vincristine treatments, MTT assays, and LDH assays were performed as described in Example 14B.

Lentivirus experiments were performed using two lentivirus vectors: GCMV-MCS-IRES-eGFP and GCMV-MCS-IRES-dsRed. Both vectors are HIV1 strains that lack the structural viral genes gag, pol, env, rev, tat, vpr, vif, vpu, and nef. In addition, there is a partial deletion of the promoter/enhancer sequences within the 3' LTR that renders the 5' LTR/promoter self-inactivating following integration. The genes provided in trans for both vectors are the structural viral proteins Gag, Pol, Rev, and Tat (via plasmid Delta8.9) and the envelope protein VSV-G. These plasmids are introduced into HEK293-T cells by co-transfection, and transiently express the different viral proteins required to generate viral particles. The potential for generating wild type or pathogenic lentivirus is extremely low, because it would require multiple recombination events amongst three plasmids. In addition, the virulence factors (vpr, vif, vpu, and nef) have been completely deleted from both vectors.

Neurons were infected either immediately at the time of plating or 3-5 days after plating by adding virus into cell culture media containing 5 μg/mL polybrene. The next day the virus-containing media is removed and replaced with fresh media. Cells are allowed to express the virus for 48 hours before experimentation.

Figure 40:
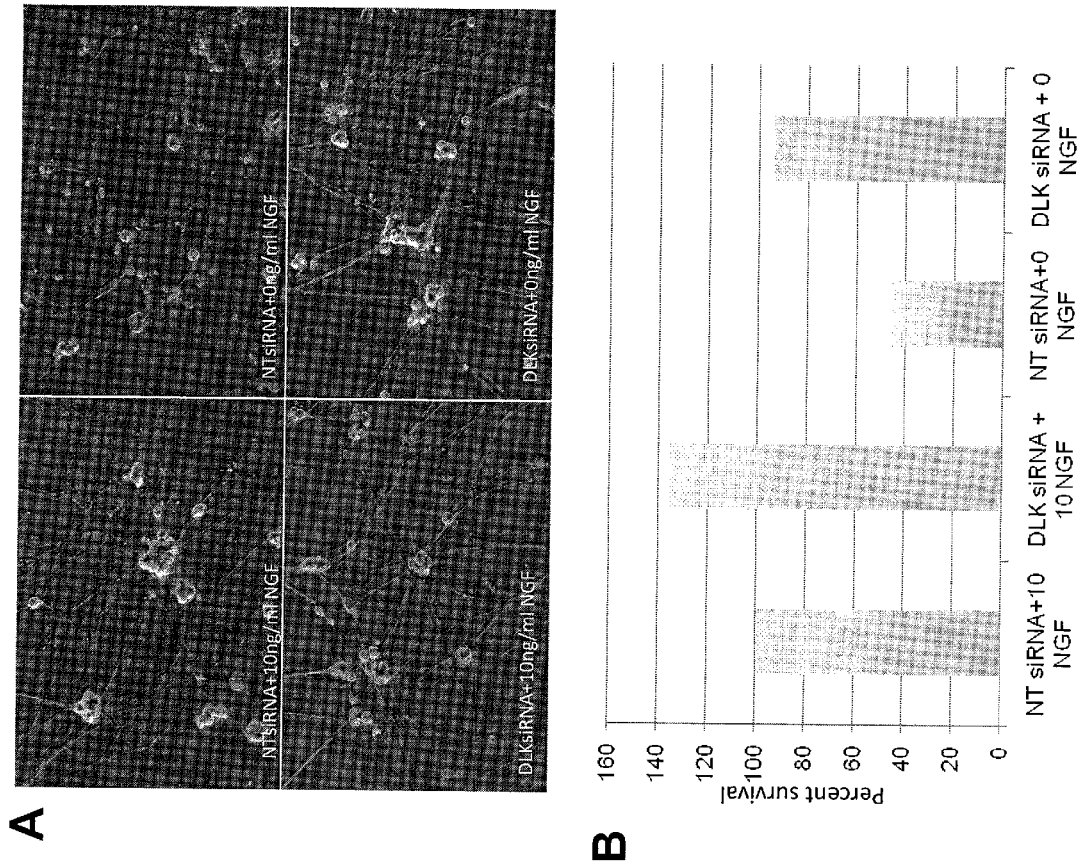
FIGS. 40A and 40B depict the results of experiments assessing the impact of DLK knockdown on NGF withdrawal-induced sympathetic neuron degeneration using phase contrast microscopy to visualize neurons.
Figure 41:
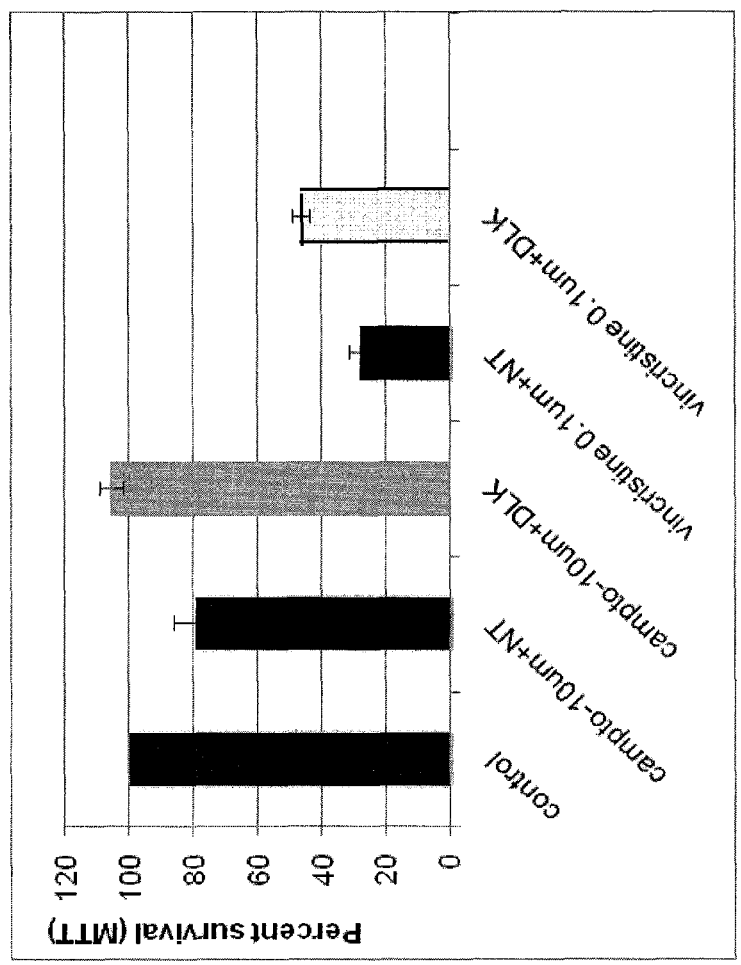
FIG. 41 shows that knockdown of DLK expression using DLK siRNA (DLK) protects sympathetic neurons from camptothecin- and vincristine-induced apoptosis compared to neurons treated with a control siRNA (NT).

Similar to the protective effect of DLK knockdown on cortical neurons and DRG, knockdown of DLK protected sympathetic neurons from NGF withdrawal-induced apoptosis (FIGS. 40A-40B and Table 10) and toxin-induced apoptosis (FIG. 41 and Table 11).

TABLE 10

DLK Knockdown Protects Sympathetic Neurons from NGF Withdrawal Stress (MTT assay)

| Condition | % viability (normalized) |
|---|---|
| Control (with NGF) | 100 |
| NGF removed 24 hours | 46 |
| DLK siRNA control | 133 |
| DLK siRNA NGF removed | 93 |

TABLE 11

DLK Knockdown Protects Sympathetic Neurons from Toxin-Induced Degeneration (MTT assay)

| Condition | % viability (normalized) |
| --- | --- |
| Control (no treatment) | 100 |
| 24 hour vincristine treatment | 28 |
| 24 hour camptothecin treatment | 79 |
| DLK siRNA (24 hour vincristine) | 47 |
| DLK siRNA (24 hour camptothecin) | 106 |

Figure 42:
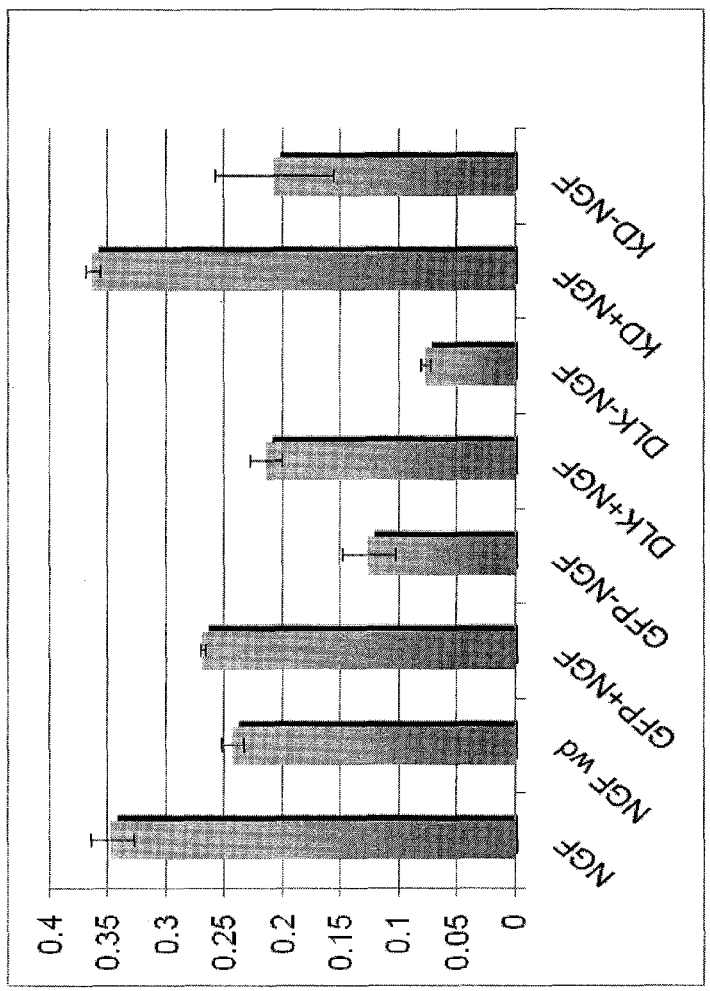
FIG. 42 shows that transfection of sympathetic neurons with a plasmid encoding kinase-dead DLK (KD) protects the neurons from NGF withdrawal-induced apoptosis compared to neurons transfected with a plasmid encoding wild type DLK (DLK).

Notably, introduction of an excess of kinase-dead DLK was similarly protective against NGF withdrawal-induced apoptosis in sympathetic neurons (FIG. 42 and Table 12).

TABLE 12

Dominant Negative DLK was Protective Against NGF Withdrawal-Induced Degeneration in Sympathetic Neurons (MTT assay)

| Condition | % viability (normalized) |
| --- | --- |
| GFP virus control (with NGF) | 77 |
| GFP virus -- NGF removed | 36 |
| DLK virus control (with NGF) | 62 |
| DLK virus - NGF removed | 22 |
| DLK DN virus control (with NGF) | 104 |
| DLK DN virus - NGF removed | 60 |

This finding was consistent with the finding in Example 15 that kinase-dead DLK introduced into 293 cells inhibited JNK phosphorylation in those cells. One non-limiting possibility is that kinase-dead DLK may prevent normal DLK dimerization and self-phosphorylation. This finding suggests that inhibition of DLK's JNK-phosphorylating capabilities, either through reduction of DLK expression or through introduction of a DLK variant lacking kinase activity, protects many types of growth factor withdrawal.

Example 15

Having determined that RNA silencing of DLK and introduction of kinase-dead DLK were each protective against NGF withdrawal-triggered or toxin-induced degeneration of cultured neurons, further experiments were performed to identify the role of DLK in neuronal degeneration pathways. DLK is a MAP kinase in the multiple lineage kinase (MLK) family. In contrast to other members of the MLK family, the expression of DLK is restricted to the nervous system (Gallo et al., *Nat. Rev. Mol. Cell. Biol.* 3(9):663-672, 2002; Bisson et al., *Cell Cycle* 7(7):909-916, 2008; Holzman et al., *J. Bio. Chem.* 269(49):30808-30817, 1994). DLK is a member of a signal transduction pathway activating JNK1-3 and cJun that results in apoptosis/inflammation under certain conditions. Increased JNK/cJun activity has been linked to a variety of neural disorders, including Parkinson's disease, glaucoma, Alzheimer's disease, ALS, stroke, and Huntington's disease through examination of patient samples or experiments in animal models of disease (Oo et al., *J. Neurochem.* 72(2):557-564, 1999; Ries et al., *J. Neurochem.* 107(6):1578-1588, 2008; Vlug et al., *Eur. J. Neurosci.* 22(8):1881-1894, 2005; Morfini et al., *Nat. Neurosci.* 12(7):864-781, 2009; Perrin et al., *Exp. Neurol.* 215(1):191-200, 2009; Levkovitch-Verbin et al., *Eye Res.* 80(5):663-670, 2005; Tezel et al., *Brain Res.* 996(2):202-212, 2004; Kuan et al., *Proc. Natl. Acad. Sci. U.S.A.* 100(25):15184-15189, 2003; Yang et al., *Nature* 389 (6653):865-870, 1997; Hunot et al., *Proc. Natl. Acad. Sci. U.S.A.* 101(2):665-670, 2004; Thakur et al., *J. Neurosci. Res.* 85(8):1668-1673, 2007). Potential correlation of DLK to neural disorders and the involvement of one or more JNK/cJun activation pathways was investigated.

A. Antibodies Specific for Phosphorylated DLK

Figure 43:
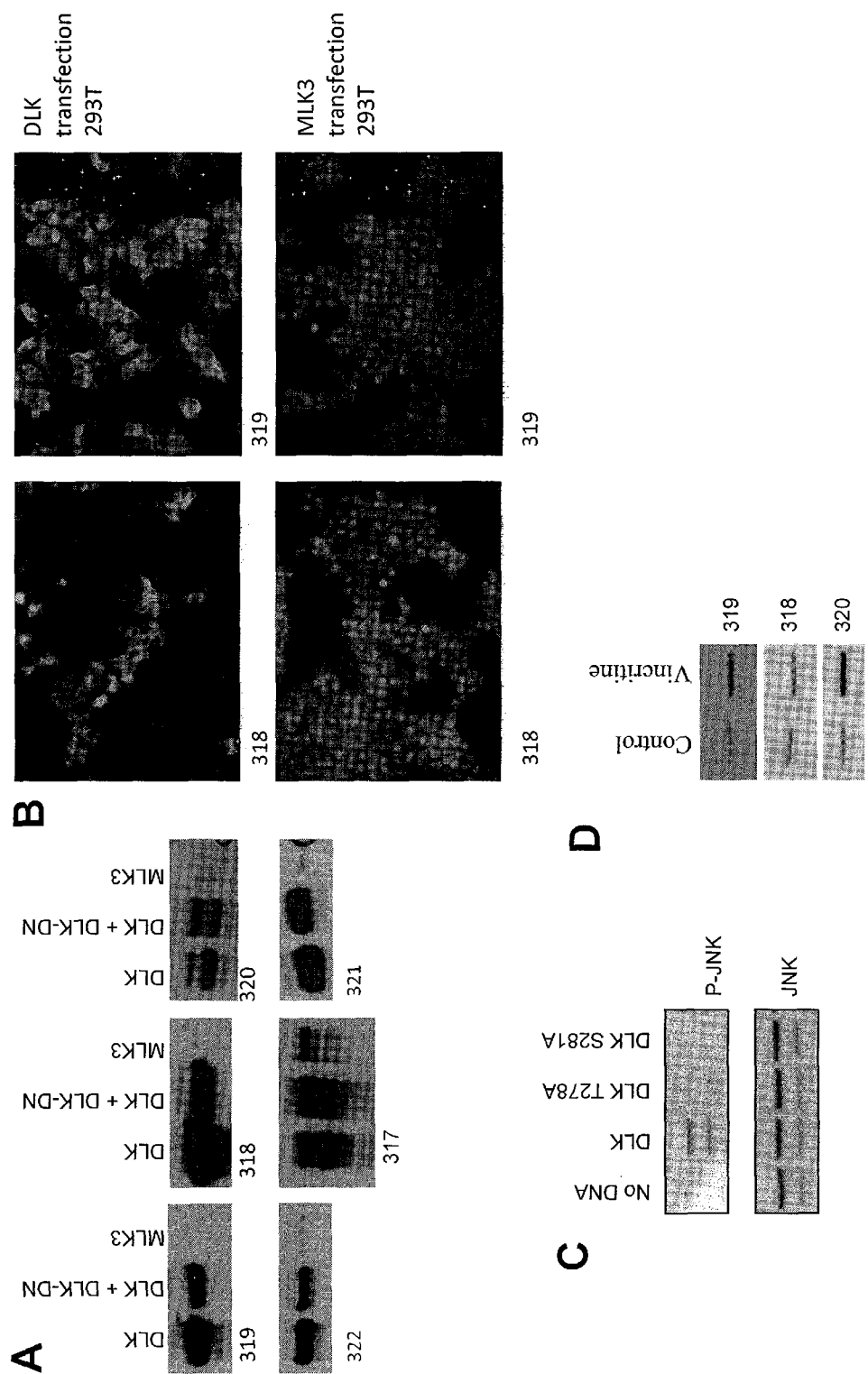
FIGS. 43A-43D show the results of experiments assessing the binding specificities of the anti-pDLK antibodies described in Example 15A.

DLK is a MAP kinase and, like other MAP kinases, it is phosphorylated within the activation loop in its activated state. In order to be able to distinguish readily between activated and resting (non-activated) DLK, antibodies were generated that are specific for the phosphorylated form of DLK ("p-DLK"). To do this, specific residues in the active site were mutated to alanine, which cannot be phosphorylated. These constructs were then transfected into 293 cells using the same protocol as described in Example 14, part A (above), and tested for their abilities to phosphorylate the downstream kinase JNK (FIG. 43C). This analysis confirmed that threonine 278 (T278) and serine 281 (S281) were required for activity. Antibodies were generated against peptides in the activation loop of the DLK protein that contained these residues using standard in vivo immunization techniques in rabbits. The peptide sequences used for immunization were CKELSDKSpTKMpSFAG (SEQ ID NO: 13) for antibodies 317 and 318, and KMpSFAGTVAWMAKKC (SEQ ID NO: 14) for antibodies 319 and 320, and CGTSKELSDKSpTKM (SEQ ID NO: 15) for antibodies 321 and 322. The procedure was performed at Yenzym, using the "p-site" protocol, which includes purification on columns of phosphorylated and unphosphorylated peptide to generate selectivity. Polyclonal antibodies from six immunized rabbits were isolated and screened for binding to DLK and p-DLK.

Six of the obtained polyclonal antibodies were subjected to Western blot and immunohistochemistry analyses to determine their abilities to detect p-DLK, and to distinguish it from non-phosphorylated DLK or other phosphorylated kinases and phosphorylated MLK3. For cultured cells, the media was removed and the cells were washed once with ice-cold PBS. Cells were scraped in cold PBS and were transferred to an eppendorf tube on ice. Cells were quickly pelleted and excess buffer was removed. The pellets were either snap-frozen on dry ice and stored at −80° C., or were immediately lysed in fresh lysis buffer (20 mM Tris, 150 mM NaCl, 0.1% Triton X-100) containing phosphatase (Sigma P5726 and P2850) and protease inhibitors (Roche 11836153001). Cells were lysed on a rotator at 4° C. for 30 minutes and then pelleted at 4° C. Protein concentrations were determined using a BCA assay (Pierce).

Protein lysates were mixed with sample buffer (Invitrogen), boiled for 5 minutes, and then loaded onto a denaturing 4-12% gradient gel (Invitrogen). Samples were transferred onto nitrocellulose (Invitrogen) and blocked in 5% milk/TBST blocking solution (Tris-buffered saline+0.05% Triton X-100) for 1 hour. The blot was incubated with a phospho-DLK antibody at a dilution of 1:1000 in TBST with 5% BSA on a shaking platform overnight at 4° C. Blots were washed three times for 5 minutes with TBST, and incubated with a rabbit secondary horseradish peroxidase (HRP)-conjugated antibody (Jackson Labs, 1:5000) for 1-2 hours at room temperature. Membranes were washed three times in TBST and developed with Westdura chemiluminescent substrate (Pierce).

293T cells were plated onto coverslips contained in a 12-well culture dish for immunostaining. The cells were then transfected with either mDLK or mMLK3 as previously described and then fixed with 4% PFA, 30% sucrose 24 hours after transfection. Cells were blocked and permeabilized with 5% BSA, 0.3% Triton X-100 for an hour, and then incubated with the primary antibody at 1:500 concentration in 1% BSA overnight. Next the cells were gently rinsed with PBS three times and conjugated with Alexa488 anti-rabbit secondary antibody for 1 hour. This step was followed by three PBS washes, with the final wash containing DAPI (1:5000) to stain nuclei. The coverslip was then carefully lifted out of the culture and mounted onto a slide with the surface with cells facing down on the slide, and the slides were visualized using fluorescence microscopy.

Antibodies 318, 319, 320, 321, and 322 each detected p-DLK and p-DLK/DN-DLK with no (antibodies 318 and 319) or very limited (antibodies 320, 321, and 322) binding to phosphorylated MLK3 (FIG. 43A). In contrast, antibody 317 recognized all three proteins. Antibodies 318 and 319 showed the strongest binding to p-DLK, coupled with minimal p-MLK3 binding, and thus were used for further analysis.

The antibodies were also able to specifically bind to p-DLK in the context of a cell, as measured by immunohistochemistry. Both antibodies 318 and 319 stained DLK-transfected 293T cells, with significantly reduced binding observed in MLK3-transfected 293T cells (FIG. 43B). This binding is significantly reduced in 293 cells that have been transfected with DLK mutants having a mutation that results in a near complete lack of kinase activity (FIG. 43C). As DLK, like other mixed lineage kinases, is thought to dimerize and autophosphorylate when transfected in heterologous systems, these data further confirm that these antibodies indeed recognize the phosphorylated form of DLK.

B. Activation of DLK During Vincristine-Induced Degeneration of Cortical Neurons The antibodies generated as described above were then tested to assess whether DLK phosphorylation and activity were increased in cortical neurons that had been stressed with vincristine. This would be expected, as knockdown of DLK activity promoted survival. When grown as described above and treated with vincristine for 1 hour, levels of phosphorylated-DLK were elevated as compared to control cultures when analyzed by Western blot (same protocol as described above) using antibodies 318, 319, and 320 (FIG. 43D). This provided further validation that levels of phosphorylated DLK correlate with activity and are increased under conditions of neuronal stress.

C. Expression and Activity of DLK in Neuronal Disease Models

Immunohistochemistry assays were performed as follows. SOD1 transgenic animals were perfused with 4% paraformaldehyde and the spinal cords were carefully removed from the vertebral column and post-fixed overnight at 4° C. The cords were then equilibrated in 30% sucrose/PBS before embedding in OCT for cryosectioning. Coronal sections (20 μm thick) were cut and mounted on cold slides and kept at −80° C. Sections were hydrated in PBS and blocked for endogenous peroxidase activity with $H_2O_2$ (0.3% in PBS) for 10 minutes, followed by rinsing twice with PBST (0.1% Triton X-100). The sections were blocked in 5% BSA, 0.3% Triton X-100 in PBS for 1 hour, and then incubated with primary antibody in p-DLK in 1% BSA, 0.3% Triton X-100 in PBS at 4° C. overnight. Slides were washed three times in PBST and then labeled with biotinylated secondary antibody (1:300) in PBS containing 1% BSA, 0.3% Triton X-100 for 1 hour. The slides were rinsed with PBST followed by a 30-minute incubation with avidin DH containing ABS reagent (Vector labs), and finally incubated in peroxidase substrate (0.05% di-amino bendizine in 10 mM Tris, 150 mM NaCl, pH 7.6 to which 30% $H_2O_2$ was added just before use) in the dark for 10-15 minutes. The reaction was stopped by rinsing with water, and the sections were mounted on glass slides and coverslipped. Alzheimer's patient tissue was purchased from US Biological. Tissue lysate from hippocampi of Alzheimer's patients and age-matched controls were used for this analysis. Analysis was conducted by Western blot using the same protocols as described above.

Figure 44:
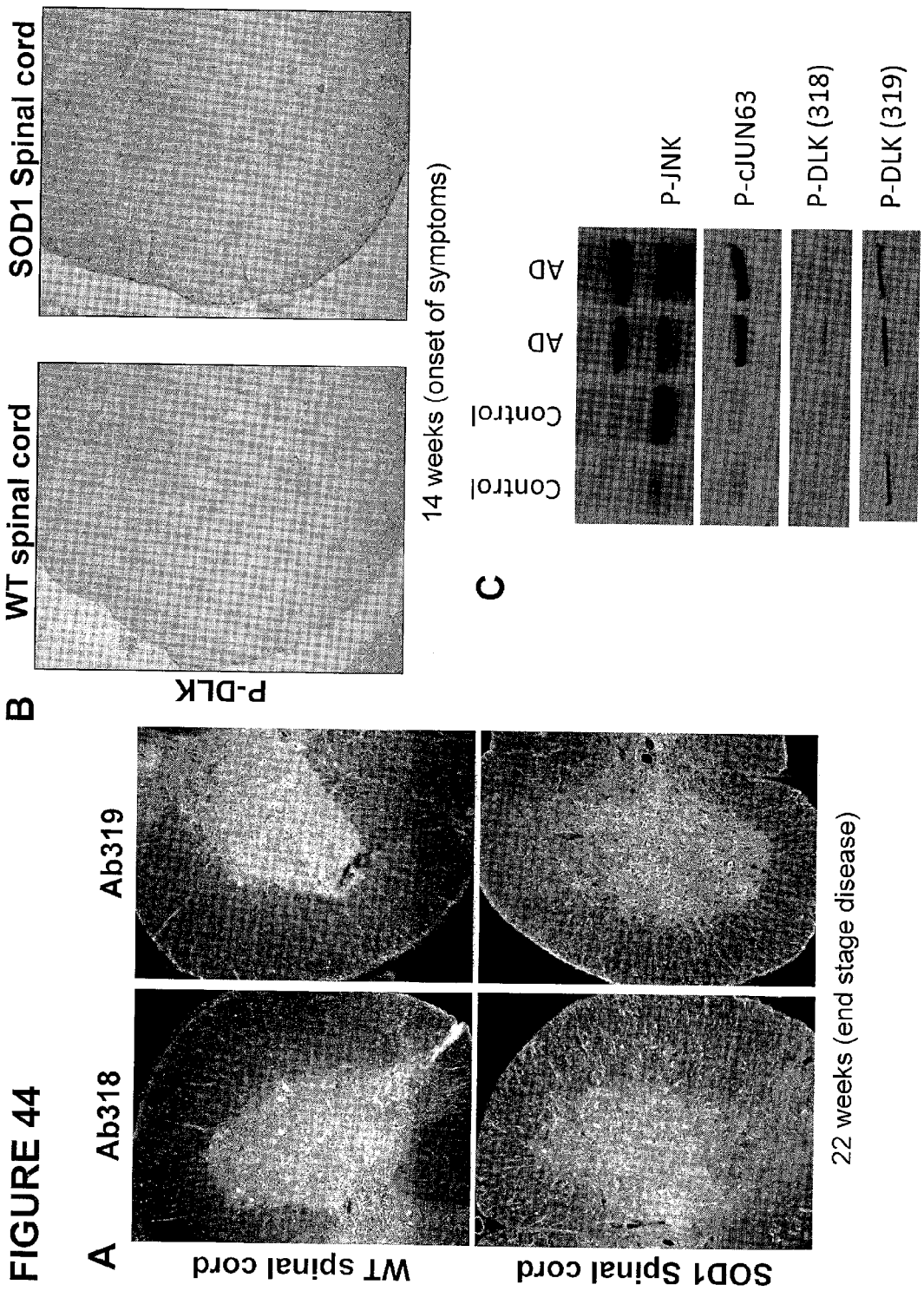
FIGS. 44A and 44B show binding of anti-pDLK antibodies (antibody 318) to spinal cord sections in wild type and SOD 1 mutant mice at end stage of disease (FIG. 43A) and at the onset of symptoms (FIG. 44B).
FIG. 44C depicts Western blot analyses of pDLK, pJNK, and pcJUN levels in human Alzheimer's disease patient cortical samples.

The results in FIG. 44A demonstrate that the levels of phosphorylated-DLK (p-DLK) were highly elevated in the SOD1 mouse of ALS relative to wild type mice late in the course of disease. Evidence of p-DLK was evident in tissue samples as early as 14 weeks (FIG. 44B), which is prior to the onset of ALS-like symptoms in these animals.

Similar results were observed in human Alzheimer's patient samples. The levels of p-DLK in cortex samples in Alzheimer's disease patients were increased relative to control samples (FIG. 44C). The levels of phosphorylated JNK and phosphorylated cJun63 levels were also increased in Alzheimer's disease patients relative to control samples (FIG. 44C). Thus, DLK is activated in a recognized mouse model of ALS, both prior to the onset of symptoms and at the end stage of disease, and also in cortical samples from human Alzheimer's patients.

D. Signaling Contributing to Observed DLK Inhibition Effect

1. Molecular Effect of DLK Silencing

As evidenced above in Example 14, DLK silencing protects neurons from degradation in response to toxin exposure or growth factor withdrawal, and DLK kinase activity is involved directly or indirectly in JNK phosphorylation. Experiments were performed to assess JNK and cJun expression and activity under NGF withdrawal stress and toxin-dependent stress conditions. The experimental protocols used to decrease the expression of DLK (siRNA) and for immunoblotting were the same as those described above.

Figure 45:
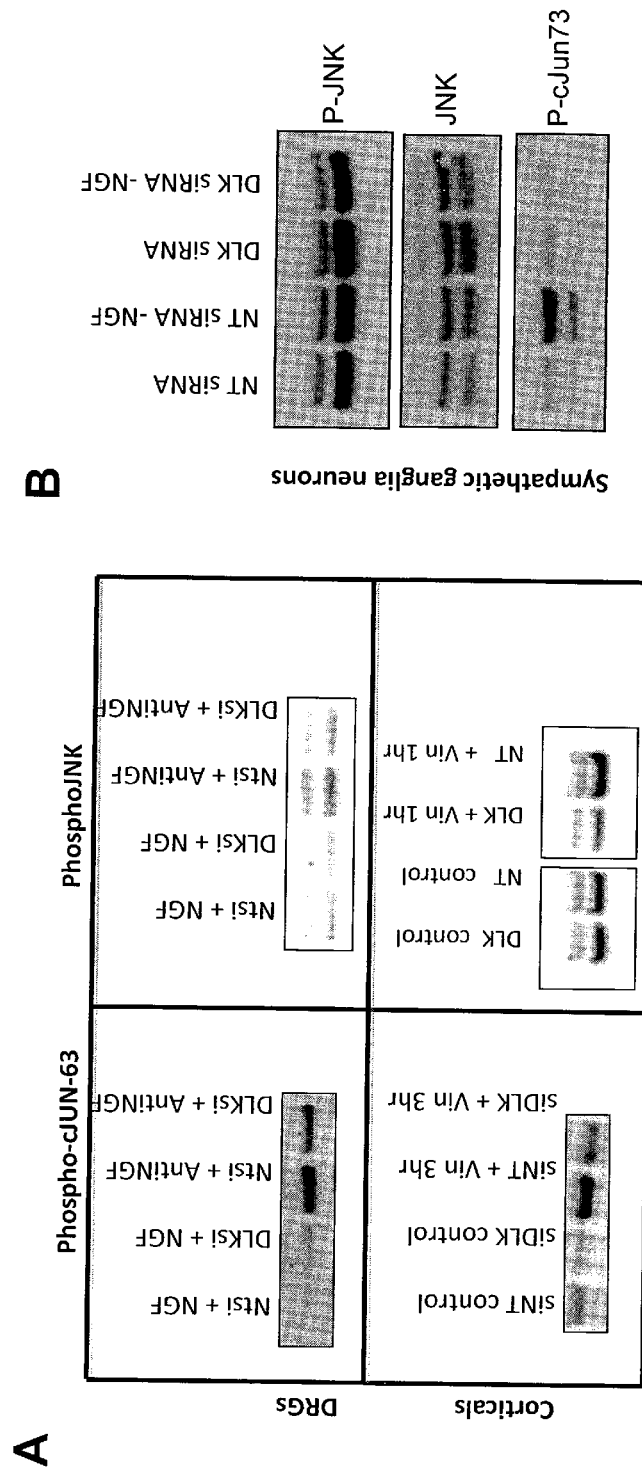
FIGS. 45A and 45B depict the results of experiments assessing the impact of DLK silencing on phosphorylation of JNK in response to NGF withdrawal stress in sympathetic neurons and dorsal root ganglion neurons; and vincristine-induced stress in cortical neurons, as described in Example 15C and Example 14B.

Silencing of DLK did not change baseline JNK protein levels or JNK activity in DRGs or cortical neurons (FIG. 45). DLK knockdown however decreased p-cJun levels after either NGF withdrawal or vincristine-dependent stress in cortical neurons, DRGS, and sympathetic ganglia neurons (FIG. 45). DLK knockdown also decreased p-JNK levels after either NGF withdrawal or vincristine-dependent stress in cortical neurons and DRG (FIG. 45). It should be noted that the p-JNK antibody recognizes the phosphorylated forms of each of JNK1, JNK2, and JNK3. JNK1 phosphorylation does not correlate with stress induction or phosphorylation of cJun. DLK knockdown silences stress-induced phosphorylation of JNK2 and JNK3. The background signal observed in the control samples in these data is likely due to baseline phosphorylated JNK1. The results show that DLK silencing or other inhibition does not cause degradation of JNK or cJun, but does result in a lesser degree of stress-induced phosphorylation (and thus lack of activation) of those molecules.

Figure 46:
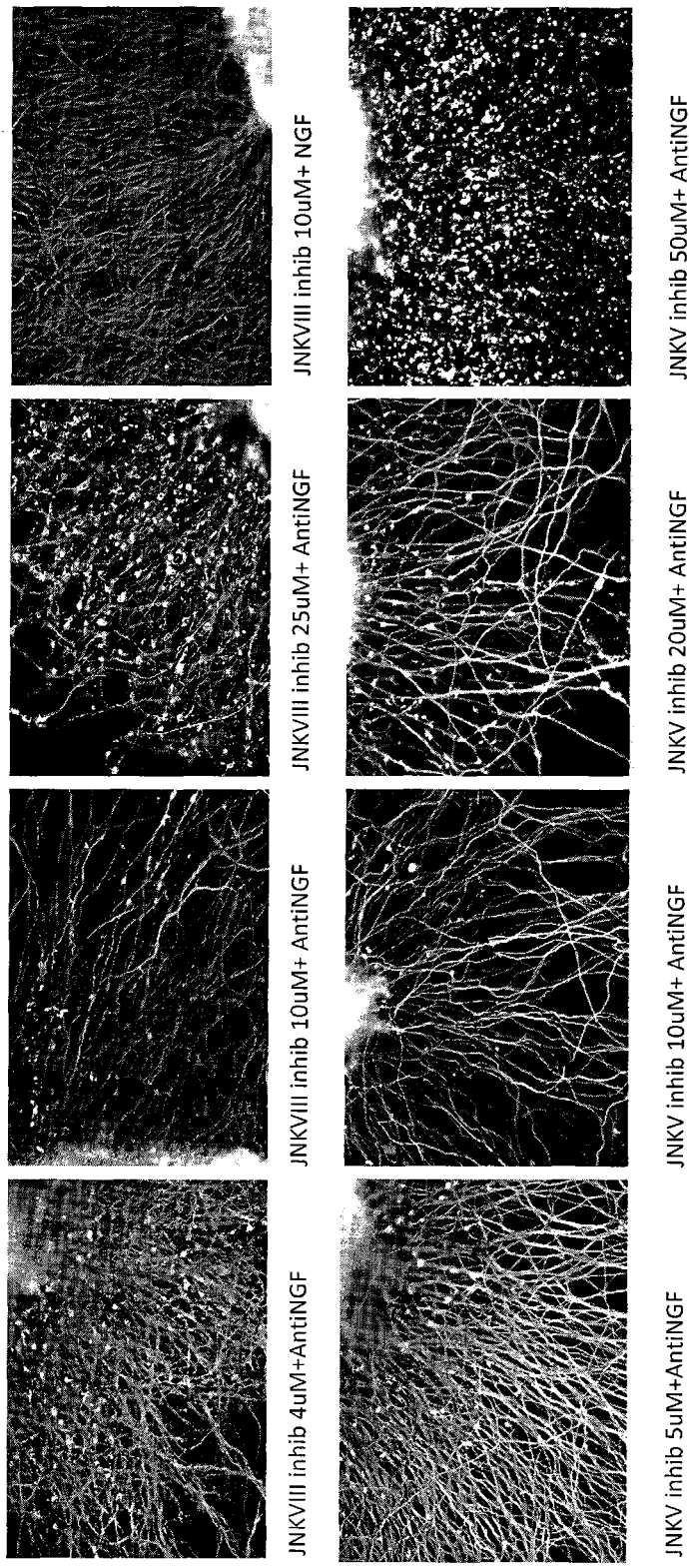
FIG. 46 shows the protective effect of JNK inhibitors on DRG explants subjected to NGF withdrawal stress, as described in Example 15C.

If DLK inhibition protects neurons from degeneration through limiting the phosphorylation of JNK2 and JNK3, then inhibitors of JNK2 or JNK3 should also protect neurons from cell death and axon degeneration. The ability of direct JNK inhibition to protect neurons against NGF withdrawal-dependent degeneration was also assessed. DRG explants were treated with anti-NGF and either pan-JNK inhibitor JNKV or JNKVIII, prior to assessment in the NGF withdrawal assay described above. Both inhibitors were able to protect DRG explants from NGF-dependent degeneration (FIG. 46): JNKV (Calbiochem) was most protective at a concentration of 5 μM, and JNKVIII (Calbiochem) at a concentration of 4

Figure 47:
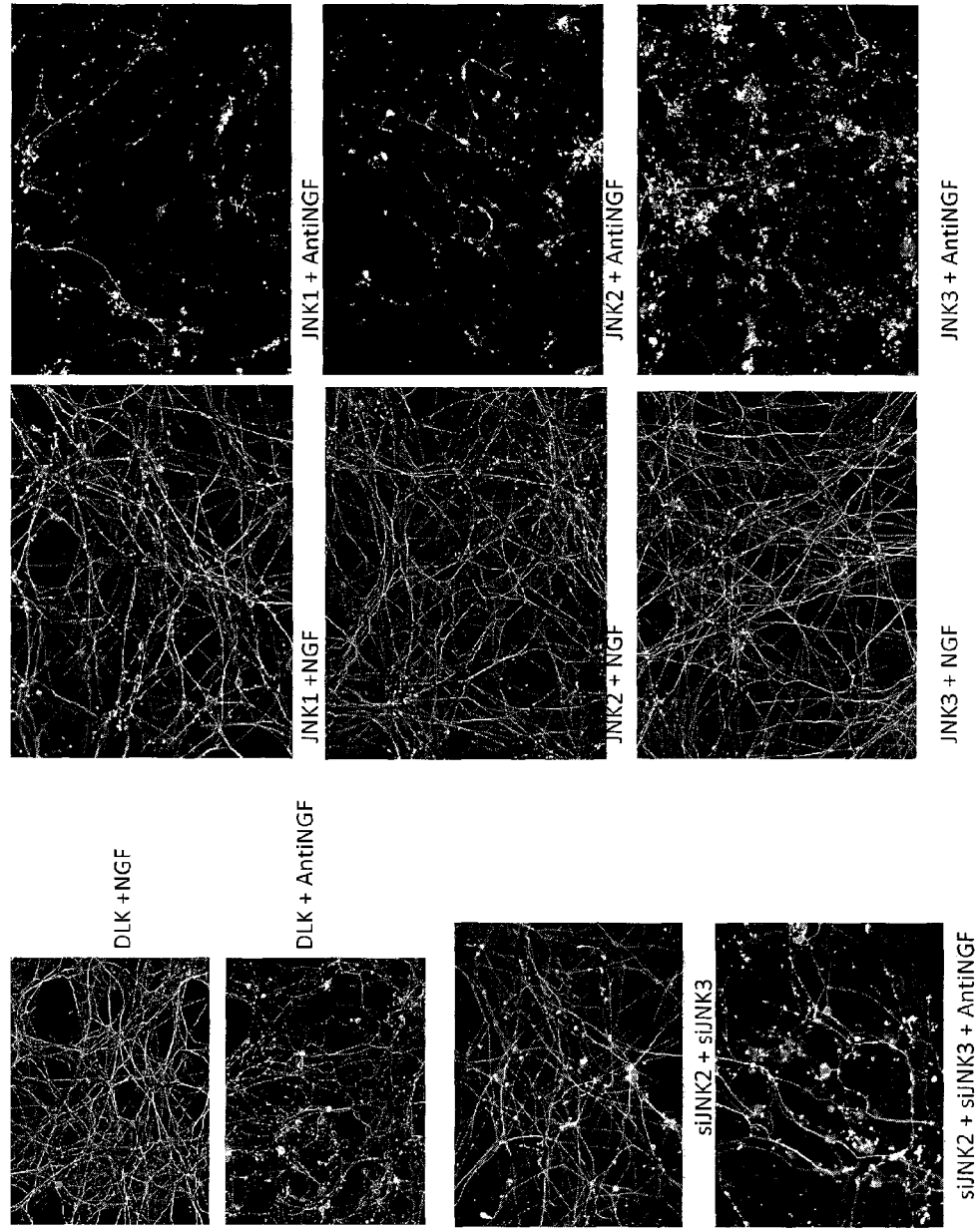
FIG. 47 depicts the results of experiments assessing the impact of silencing JNK1, JNK2, JNK3, individually, and JNK2 and JNK3 together in DRG neurons on axon degeneration observed upon NGF withdrawal stress, as described in Example 15C.

To identify which JNK(s) were involved in the observed protective effect, further knockdown experiments were performed using the same methodology as described above. Silencing RNAs specific for JNK1 alone were not able to replicate the effects observed with the pan-INK inhibitors (FIG. 47). Inhibitory RNAs (siRNAs) for JNK2 or JNK3 alone were not able to protect DRG against axon degeneration upon NGF withdrawal (FIG. 47). The most effective protection was observed in the presence of silencing of both JNK2 and JNK3, though even this protection was not the same extent as siDLK alone (FIG. 47).

JNK1 is a constitutively active molecule, known to be responsible for axon maintenance and synapse maturation, whereas JNK2 and JNK3 are known to be stress-induced and involved in cJun activation and apoptosis/axon degeneration (Coffey et al., *J. Neurosci.* 22(11):4335-4345, 2002; Coffey et al., *J. Neurosci.* 20(20):7602-7613, 2000). The fact that DLK inhibition results in a larger neuroprotective effect than JNK1/2/3 inhibition strongly suggests that DLK is inhibitory to one or more mechanisms of neuron growth and/or survival in addition to its role in the JNK/cJUN pathway.

E. Trophic Effects of DLK

A previous study has suggested that a dominant negative kinase-dead mutant form of DLK (K152A) causes trophic effects in dopaminergic neurons of the substantia nigra pars compacta, whereas a dominant negative form of DLK containing only the leucine zipper domain does not cause such effects (Chen et al., *J. Neurosci.* 28(3):672-680, 2008). Notably, however, trophism in this study was defined by an increased number of DLK (K152A) infected neurons expressing a particular marker rather than any functional or morphological differences between infected and non-infected neurons. The impact of DLK silencing was accordingly investigated in cortical neurons and DRGs. The protocols used for these studies were the same as those described above.

Figure 48:
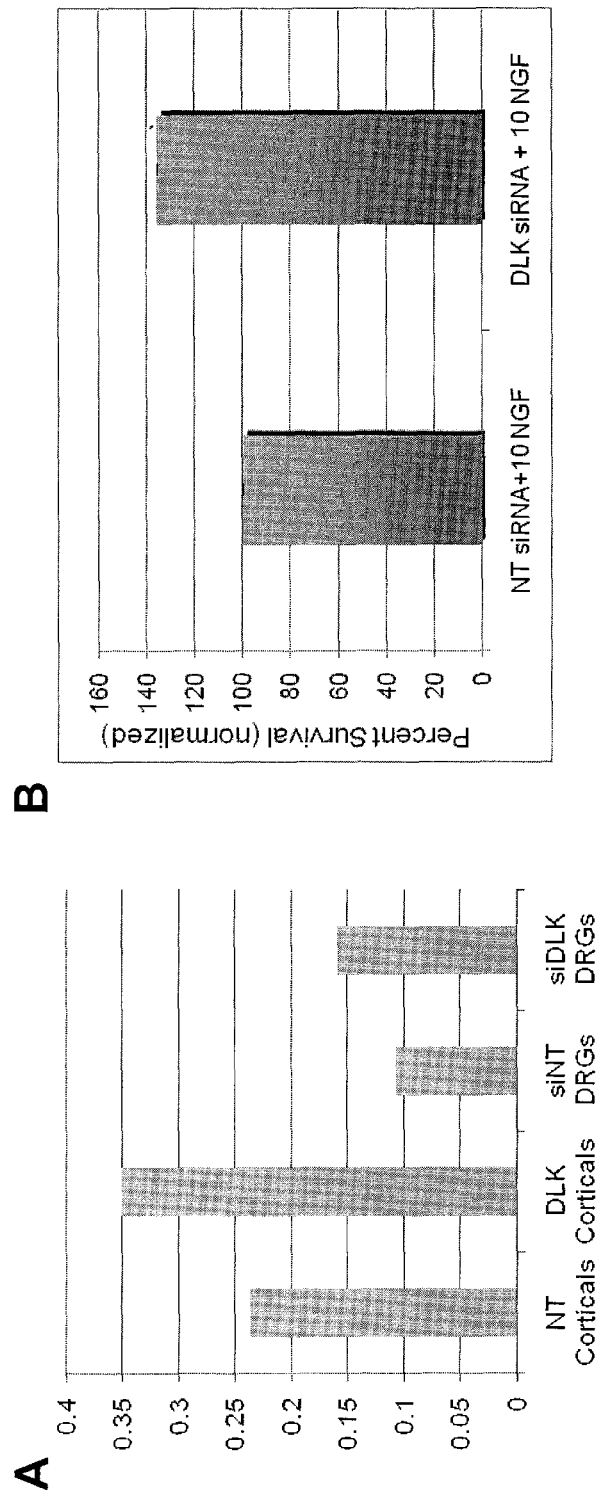
FIG. 48A shows the affect of DLK siRNA and control siRNA on the survival of cortical neurons.
FIG. 48B shows the affect of DLK siRNA and control siRNA on the survival of sympathetic neurons.

DLK knockdown was shown to have pronounced trophic effects in both cortical neurons and sympathetic neurons (observed increase in number of cells) (FIGS. 48A and 48B). Specifically, DRG, cortical, and sympathetic neurons showed increased growth/survival in culture when treated with siRNA directed against DLK (observed increase in growth) (Table 13).

TABLE 13

Increased Growth of Multiple Types of Neurons in Culture after DLK Knockdown (MTT assay)

| Condition | % viability (normalized) |
|---|---|
| Cortical neurons control | 100 |
| Cortical neurons + DLK siRNA | 137 |
| Sympathetic neurons control | 100 |
| Sympathetic neurons + DLK siRNA | 139 |
| DRG neurons | 100 |
| DRG neurons + DLK siRNA | 147 |

To further examine the role of DLK in neuronal growth, the levels of MAP2, were measured, a microtubule associated protein that is specifically localized to dendrites. MAP2 expression in cultured neurons is reflective of neuronal maturation and expression, and is often increased under pro-growth conditions. Inhibition of DLK activity using either a dominant-negative leucine zipper form of DLK or a dominant negative kinase-dead form of DLK in neurons resulted in induction of MAP2 protein production. The induction of MAP2 expression indicates that neuronal growth and maturation are taking place, and further confirms that DLK knockdown indeed has a functional trophic effect on neurons.

Example 16

The assays described herein identified several inhibitors of G-proteins and G-protein coupled receptors (GPCRs) that decrease degeneration in neurons. Experiments were performed in DRGs to verify the role of G-proteins and GPCRs in degeneration pathways. The experimental protocols used in these experiments are the same as those described in Example 14. Pertussis toxin and SCH 202676 were purchased from Tocris Bioscience.

Figure 49:
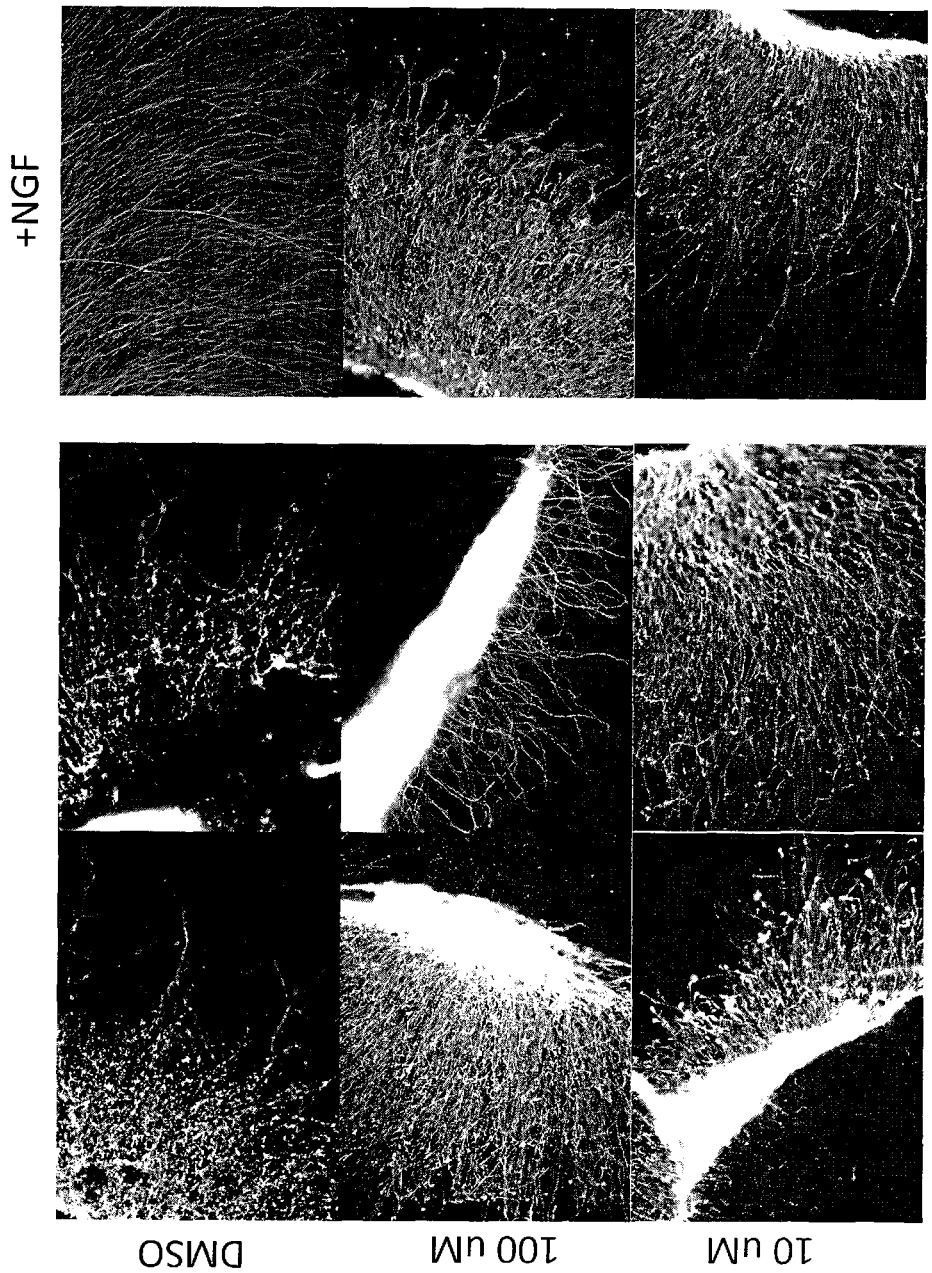
FIG. 49 is a set of immunomicrographs showing the ability of an inhibitor of G-coupled protein receptors (SCH 202676; 10 µM or 100 µM) to prevent NGF withdrawal-induced degeneration in DRGs.
Figure 50:
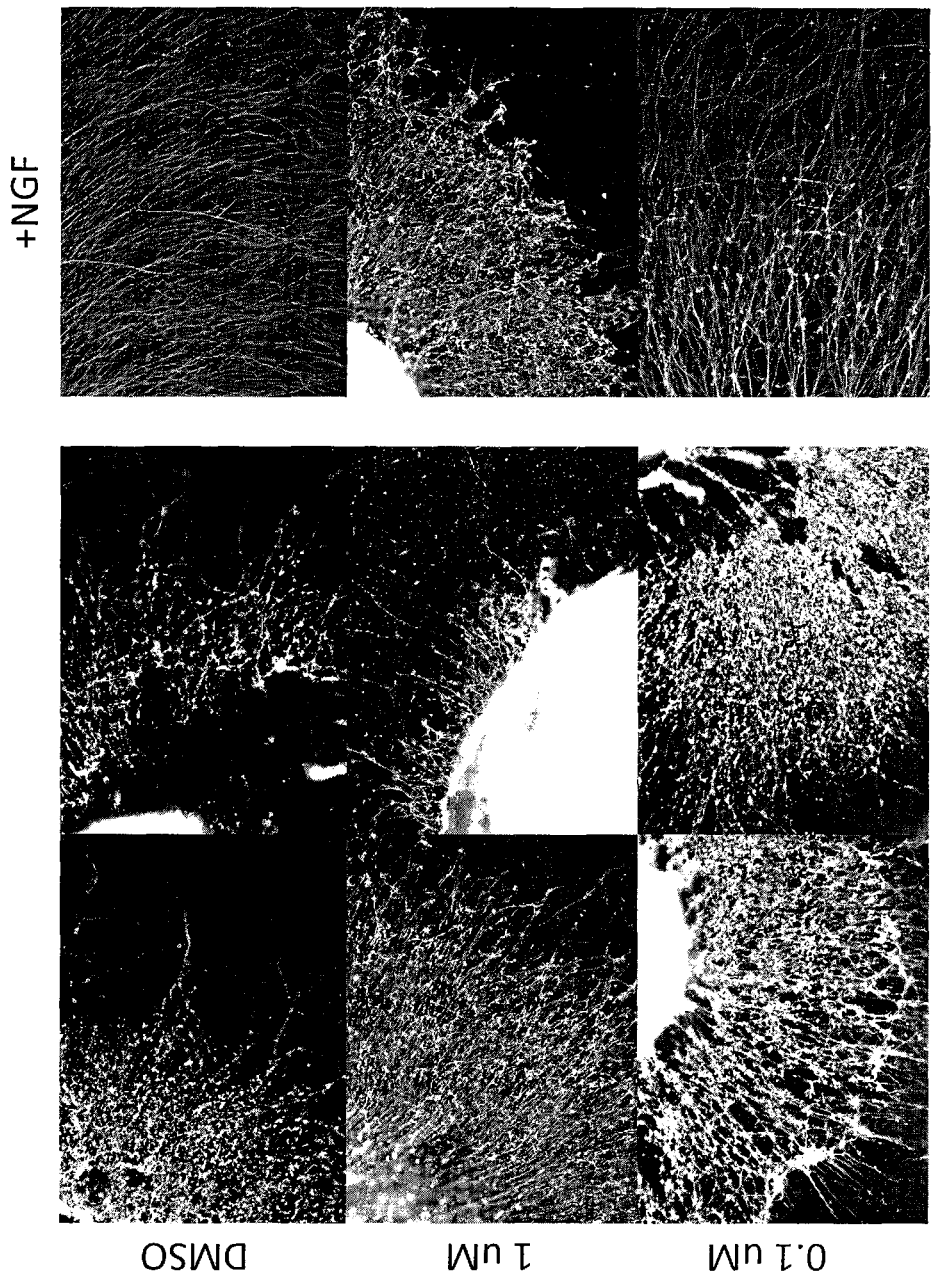
FIG. 50 is a set of immunomicrographs showing the ability of SCH 202676 (0.1 µM or 1 µM) to prevent NGF withdrawal-induced degeneration in DRGs.
Figure 51:
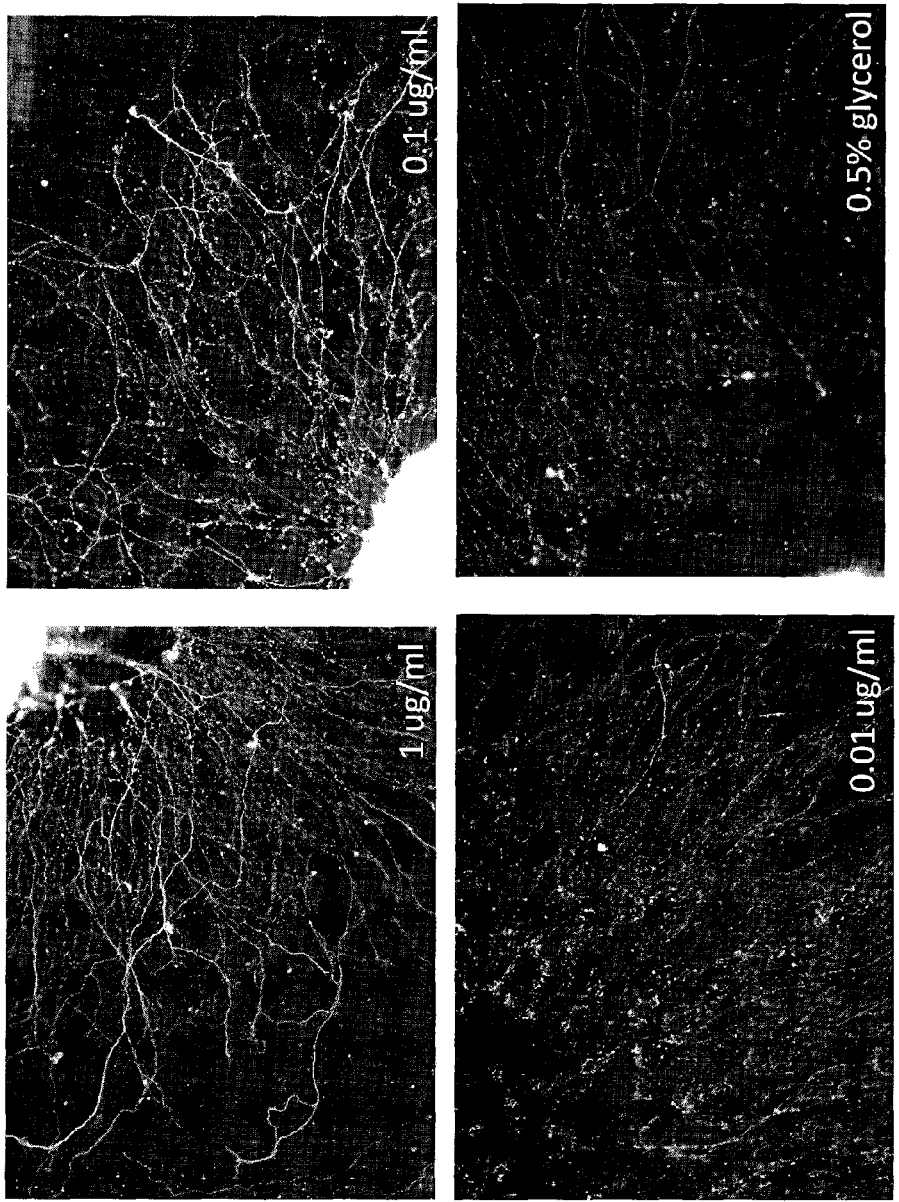
FIG. 51 is a set of immunomicrographs showing the ability of 0.01 µg/mL, 0.1 µg/mL, or 1 µg/mL pertussis toxin (an inhibitor of G-protein signaling) to prevent NGF withdrawal-induced degeneration in DRGs.

The data demonstrate that SCH 202676, a sulphydryl-reactive compound that inhibits agonist and antagonist binding to G protein-coupled receptors, decreases NGF withdrawal-induced degeneration in DRGs (FIGS. 49 and 50). Pertussis toxin, another inhibitor of G-protein signaling, also decreases degeneration in neurons following NGF withdrawal (FIG. 51). These data indicate that G-proteins and G-protein coupled receptors play a role in neuron degeneration.

Example 17

Additional cellular targets, identified in the assays described herein, and which play a role in degeneration pathways, are members of the beta-catenin signaling pathway and its downstream targets (e.g., transcription factor 4, TCF4). Experiments were performed in hippocampal neurons to verify the role of beta-catenin and TCF4 in neuron degeneration. The experimental protocols used in these experiments are the same as those described in Example 14.

Figure 52:
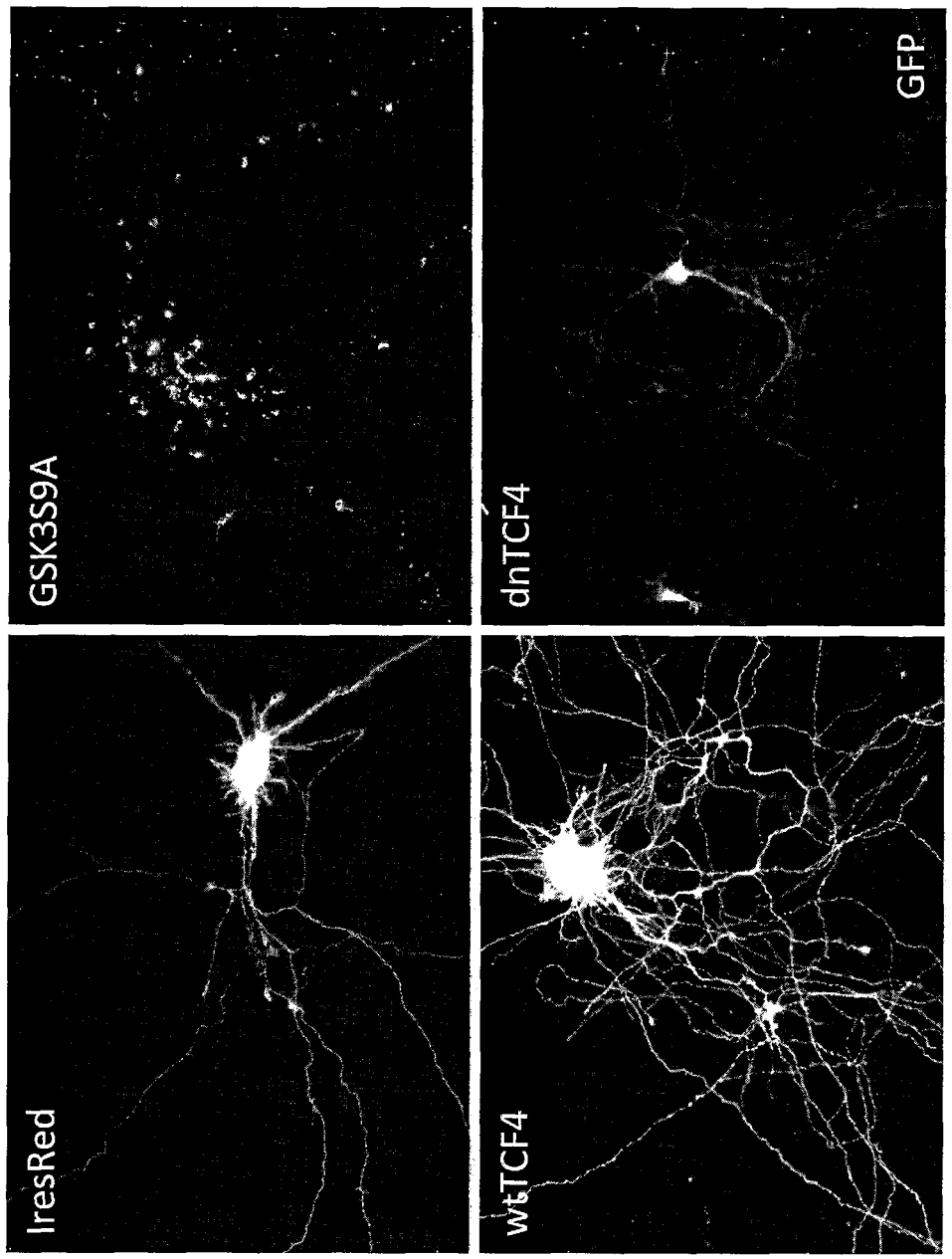
FIG. 52 is a set of immunomicrographs of rat hippocampal neurons showing the effect of expression of active mutant GSK (GSK3S9A), wild type TCF1, and mutant inactive TCF4 on degeneration.

The data show that expression of a constitutively active GSK3, which can result in loss of beta-catenin, mediates a decrease in neuron viability (FIG. 52; top right panel). The expression of a dominant negative form of TCF4 also mediates a decrease in neuron viability (FIG. 52, bottom right panel). These data indicate that the beta-catenin signaling pathway is important for the maintenance of neuron viability. Inhibitors that target the beta-catenin signaling pathway can be used to promote neuron degeneration (e.g., inhibitors of beta-catenin expression and inhibitors of TCF4 activity.) Conversely, activators or beta-catenin and TCF4 signaling may prevent axon degeneration and neuronal cell death.

Other Embodiments

All publications and patents cited in this specification are herein incorporated by reference as if each individual publication or patent were specifically and individually indicated to be incorporated by reference. Use of singular forms herein, such as "a" and "the," does not exclude indication of the corresponding plural form, unless the context indicates to the contrary. Although the invention has been described in some detail by way of illustration and example for purposes of clarity of understanding, it will be readily apparent to those of ordinary skill in the art in light of the teachings of the invention that certain changes and modifications may be made thereto without departing from the spirit or scope of the appended claims.

What is claimed is:

1. A method for inhibiting degeneration of an axon of a central nervous system neuron, wherein the method comprises administering to the neuron, or a portion thereof, a short interfering RNA (siRNA) that is specific for dual leucine zipper-bearing kinase (DLK) and comprises a nucleic acid sequence selected from the group consisting of GCACTGAATTGGACAACTCTT (SEQ ID NO: 1), GAGTTGTCCAATTCAGTGCTT (SEQ ID NO: 2), GGACATCGCCTCCGCTGATTT (SEQ ID NO: 3), ATCAGCGGAGGCGATGTCCTT (SEQ ID NO: 4), GCAAGACCCGTCACCGAAATT (SEQ ID NO: 5), TTTCGGTGACGGGTCTTGCTT (SEQ ID NO: 6), GCGGTGTCCTGGTCTACTATT (SEQ ID NO: 7), and TAGTAGACCAGGACACCGCTT (SEQ ID NO: 8), wherein the siRNA inhibits or decreases the activity or expression of said DLK and inhibits degeneration of the axon.

2. The method of claim 1, wherein the neuron is selected from the group consisting of a cerebellar granule neuron, a cortical neuron, and a hippocampal neuron.

3. The method of claim 1, wherein said administering results in at least a 10% decrease in the degeneration of a population of neurons or at least a 10% decrease in the degeneration of axons in a population of neurons as compared to a control population of neurons.

4. The method of claim 1, wherein the neuron or portion thereof is present in a human subject.

5. The method of claim 4, wherein said human subject has a disorder of the central nervous system.

6. The method of claim 5, wherein the disorder of the central nervous system selected from the group consisting of amyotrophic lateral sclerosis (ALS), trigeminal neuralgia, glossopharyngeal neuralgia, Bell's Palsy, myasthenia gravis, muscular dystrophy, progressive muscular atrophy, primary lateral sclerosis (PLS), pseudobulbar palsy, progressive bulbar palsy, spinal muscular atrophy, inherited muscular atrophy, invertebrate disk syndromes, cervical spondylosis, Alzheimer's disease, Huntington's disease, Parkinson's disease, Parkinson's-plus diseases, multiple system atrophy, progressive supranuclear palsy, corticobasal degeneration, dementia with Lewy bodies, frontotemporal dementia, demyelinating diseases, multiple sclerosis, prion disease, Creutzfeldt-Jakob disease, Gerstmann-Sträussler-Scheinker syndrome (GSS), fatal familial insomnia (FFI), bovine spongiform encephalopathy, Pick's disease, epilepsy, and AIDS dementinal complex.

7. The method of claim 5, wherein the contacting of the neuron or portion thereof with the siRNA comprises administering to the subject a pharmaceutical composition comprising the siRNA.

8. The method of claim 7, wherein the administering is carried out by intravenous infusion or injection by intravenous, intraperitoneal, intracerebral, intramuscular, intraocular, intraarterial or intralesional routes.

9. The method of claim 7 or 8, further comprising administering to the subject one or more additional pharmaceutical agents.

* * * * *

SEQUENCE LISTING

<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: Inhibitory nucleic acid sequence

<400> SEQUENCE: 1
gcactgaatt ggacaactct t                                              21

<210> SEQ ID NO 2
<211> LENGTH: 21
<212> TYPE: DNA
<213> ORGANISM: Artificial Sequence
<220> FEATURE:
<223> OTHER INFORMATION: Inhibitory nucleic acid sequence

<400> SEQUENCE: 2
gagttgtcca attcagtgct t                                              21

<210> SEQ ID NO 3
<211> LENGTH: 21
<212> TYPE: DNA
<213> ORGANISM: Artificial Sequence
<220> FEATURE:
<223> OTHER INFORMATION: Inhibitory nucleic acid sequence

<400> SEQUENCE: 3
ggacatcgcc tccgctgatt t                                              21

<210> SEQ ID NO 4
<211> LENGTH: 21
<212> TYPE: DNA
<213> ORGANISM: Artificial Sequence
<220> FEATURE:
<223> OTHER INFORMATION: Inhibitory nucleic acid sequence

<400> SEQUENCE: 4
atcagcggag gcgatgtcct t                                              21

<210> SEQ ID NO 5
<211> LENGTH: 21
<212> TYPE: DNA
<213> ORGANISM: Artificial Sequence
<220> FEATURE:
<223> OTHER INFORMATION: Inhibitory nucleic acid sequence

<400> SEQUENCE: 5
gcaagacccg tcaccgaaat t                                              21

<210> SEQ ID NO 6
<211> LENGTH: 21
<212> TYPE: DNA
<213> ORGANISM: Artificial Sequence
<220> FEATURE:
<223> OTHER INFORMATION: Inhibitory nucleic acid sequence

<400> SEQUENCE: 6
tttcggtgac gggtcttgct t                                              21

<210> SEQ ID NO 7
<211> LENGTH: 21
<212> TYPE: DNA
<213> ORGANISM: Artificial Sequence
<220> FEATURE:
<223> OTHER INFORMATION: Inhibitory nucleic acid sequence

<400> SEQUENCE: 7
gcggtgtcct ggtctactat t                                              21

```
<210> SEQ ID NO 8
<211> LENGTH: 21
<212> TYPE: DNA
<213> ORGANISM: Artificial Sequence
<220> FEATURE:
<223> OTHER INFORMATION: Inhibitory nucleic acid sequence

<400> SEQUENCE: 8
tagtagacca ggacaccgct t                                              21

<210> SEQ ID NO 9
<211> LENGTH: 21
<212> TYPE: DNA
<213> ORGANISM: Artificial Sequence
<220> FEATURE:
<223> OTHER INFORMATION: JNK1 target nucleic acid sequence

<400> SEQUENCE: 9
ttggatgaag ccattagact a                                              21

<210> SEQ ID NO 10
<211> LENGTH: 21
<212> TYPE: DNA
<213> ORGANISM: Artificial Sequence
<220> FEATURE:
<223> OTHER INFORMATION: JNK2 target nucleic acid sequence

<400> SEQUENCE: 10
acctttaatg gacaacatta a                                              21

<210> SEQ ID NO 11
<211> LENGTH: 21
<212> TYPE: DNA
<213> ORGANISM: Artificial Sequence
<220> FEATURE:
<223> OTHER INFORMATION: JNK2 target nucleic acid sequence

<400> SEQUENCE: 11
aaggattagc tttgtatcat a                                              21

<210> SEQ ID NO 12
<211> LENGTH: 21
<212> TYPE: DNA
<213> ORGANISM: Artificial Sequence
<220> FEATURE:
<223> OTHER INFORMATION: JNK3 target nucleic acid sequence

<400> SEQUENCE: 12
cccgcatgtg tctgtattca a                                              21

<210> SEQ ID NO 13
<211> LENGTH: 15
<212> TYPE: PRT
<213> ORGANISM: Artificial Sequence
<220> FEATURE:
<223> OTHER INFORMATION: DLK1 peptide sequence
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: MOD_RES
<222> LOCATION: (9)..(9)
<223> OTHER INFORMATION: phosphorylated threonine
<220> FEATURE:
<221> NAME/KEY: MOD_RES
<222> LOCATION: (12)..(12)
<223> OTHER INFORMATION: phosphorylated serine
```

```
<400> SEQUENCE: 13

Cys Lys Glu Leu Ser Asp Lys Xaa Thr Lys Met Xaa Phe Ala Gly
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: DLK1 peptide sequence
<220> FEATURE:
<221> NAME/KEY: MOD_RES
<222> LOCATION: (3)..(3)
<223> OTHER INFORMATION: phosphorylated serine

<400> SEQUENCE: 14

Lys Met Xaa Phe Ala Gly Thr Val Ala Trp Met Ala Lys Lys Cys
1               5                   10                  15

<210> SEQ ID NO 15
<211> LENGTH: 14
<212> TYPE: PRT
<213> ORGANISM: Artificial Sequence
<220> FEATURE:
<223> OTHER INFORMATION: DLK1 peptide sequence
<220> FEATURE:
<221> NAME/KEY: MOD_RES
<222> LOCATION: (12)..(12)
<223> OTHER INFORMATION: phosphorylated threonine

<400> SEQUENCE: 15

Cys Gly Thr Ser Lys Glu Leu Ser Asp Lys Ser Xaa Lys Met
1               5                   10

<210> SEQ ID NO 16
<211> LENGTH: 20
<212> TYPE: DNA
<213> ORGANISM: Artificial Sequence
<220> FEATURE:
<223> OTHER INFORMATION: DLK1 forward primer

<400> SEQUENCE: 16
catcatctgg gtgtgggaag                                              20

<210> SEQ ID NO 17
<211> LENGTH: 21
<212> TYPE: DNA
<213> ORGANISM: Artificial Sequence
<220> FEATURE:
<223> OTHER INFORMATION: DLK1 reverse primer

<400> SEQUENCE: 17
agttgcagca tgagggcatt c                                            21
```